(12) United States Patent
Zahajska et al.

(10) Patent No.: US 10,093,675 B2
(45) Date of Patent: Oct. 9, 2018

(54) 6,8-DISUBSTITUTED-9-(HETEROCYCLYL) PURINES, COMPOSITIONS CONTAINING THESE DERIVATIVES AND THEIR USE IN COSMETIC AND MEDICINAL APPLICATIONS

(71) Applicants: USTAV EXPERIMENTALNI BOTANIKY AV CR, V.V.I., Prague, Lysolaje (CZ); UNIVERZITA PALACKEHO V OLOMOUCI, Olomouc (CZ)

(72) Inventors: Lenka Zahajska, Olomouc (CZ); Jaroslav Nisler, Olomouc (CZ); Alena Kadlecova, Tvrdonice (CZ); Marek Zatloukal, Sumperk (CZ); Jiri Gruz, Bohunovice (CZ); Jiri Voller, Brno-Bystrc (CZ); Karel Dolezal, Hlubocky (CZ); Miroslav Strnad, Olomouc (CZ)

(73) Assignees: USTAV EXPERIMENTALNI BOTANIKY AV CR, V.V.I., Lysolaje (CZ); UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 15/536,041

(22) PCT Filed: Oct. 21, 2015

(86) PCT No.: PCT/CZ2015/050009
§ 371 (c)(1),
(2) Date: Jun. 14, 2017

(87) PCT Pub. No.: WO2016/095880
PCT Pub. Date: Jun. 23, 2016

(65) Prior Publication Data
US 2017/0362236 A1 Dec. 21, 2017

(30) Foreign Application Priority Data
Dec. 15, 2014 (CZ) .............................. PV2014-908

(51) Int. Cl.
| | | |
|---|---|---|
| C07D 473/40 | (2006.01) |
| C07D 473/34 | (2006.01) |
| A61K 8/49 | (2006.01) |
| A61Q 19/08 | (2006.01) |
| C12N 5/00 | (2006.01) |
| C12N 5/04 | (2006.01) |
| C12N 5/07 | (2010.01) |
| C12N 5/077 | (2010.01) |

(52) U.S. Cl.
CPC .............. *C07D 473/40* (2013.01); *A61K 8/49* (2013.01); *A61Q 19/08* (2013.01); *C07D 473/34* (2013.01); *C12N 5/00* (2013.01); *C12N 5/04* (2013.01); *C12N 5/0601* (2013.01); *C12N 5/0656* (2013.01); *C12N 2501/999* (2013.01)

(58) Field of Classification Search
CPC .................................................. C07D 473/40
See application file for complete search history.

(56) References Cited

U.S. PATENT DOCUMENTS

| | | |
|---|---|---|
| 4,369,181 A | 1/1983 | Miller |
| 5,602,139 A | 2/1997 | Rattan |
| 5,968,912 A | 10/1999 | Ojo-Amaize |

FOREIGN PATENT DOCUMENTS

| | | | |
|---|---|---|---|
| WO | 00/433394 A1 | 7/2000 | |
| WO | 01/49688 A1 | 7/2001 | |
| WO | 03/040144 A2 | 5/2003 | |
| WO | 2008/008770 A2 | 1/2008 | |
| WO | 2009/086457 A2 | 7/2009 | |
| WO | WO2009/086457 | * 9/2009 | ........... C07D 473/16 |

OTHER PUBLICATIONS

Suarez et al., European J'nal of Medicinal Chem. 61 (2013) 2-25.*
Search Report for PV 2014-908 filed Dec. 15, 2014.
Suarez Rosa M et al: Inhibitors of the TAM subfamily of tyrosine kinases: Synthesis and biological evaluation, European Journal of Medicinal Chemistry, Editions Scientifique Elsevier, Paris, FR, vol. 61, Jun. 2012 p. 2-25.
International Search Report for PCT/CZ2015/050009 filed Oct. 21, 2015.
International Written Opinion for PCT/CZ2015/050009 filed Oct. 21, 2015.

* cited by examiner

*Primary Examiner* — Paul V Ward
(74) *Attorney, Agent, or Firm* — Notaro, Michalos & Zaccaria P.C.

(57) ABSTRACT

6,8-Disubstituted-9-(heterocyclyl)purines for use in pharmaceutical and cosmetic compositions and applications are provided. These 6,8-disubstituted-9-(heterocyclyl)purines have a wide range of biological activities, including for example antioxidant, anti-inflammatory, anti-senescent, anti-aging, as well as well as other activities which are especially useful in pharmaceutical and cosmetic applications. Compositions may include additional excipients and auxiliary substances. Methods of treatment of animals, mammals, plants, cells, yeast, and cells in tissue culture are also disclosed.

11 Claims, 1 Drawing Sheet

6,8-DISUBSTITUTED-9-(HETEROCYCLYL) PURINES, COMPOSITIONS CONTAINING THESE DERIVATIVES AND THEIR USE IN COSMETIC AND MEDICINAL APPLICATIONS

FIELD OF ART

The invention relates to 6,8-disubstituted-9-(heterocyclyl) purine derivatives, their use in cosmetic and medicinal applications and compositions containing these derivatives.

BACKGROUND ART

Various adenine derivatives are known in the art to be versatile compounds with many interesting properties in medicine, cosmetics and agriculture (WO 03/040144). Some of them occur naturally as plant hormones, e.g., kinetin, isopentenyladenine, trans-zeatin, dihydrozeatin, 6-benzylaminopurine, 6-(3-hydroxybenzylamino)purine (Strnad, M. *Physiol. Plant.* 1997, 101, 674; Wojtania and Gabryszewska, *Biotechnologia* 2004, 2, 162; Baroja-Fernández et al., *Plant. Physiol. Biochem.* 2002, 40, 217; Peixe et al., *Scientia Horticulturae* 2007, 113, 1). The application of these plant hormones to plants, however, brings significants undesired side effects, including problems with heterogeneity of growth and root growth inhibition (Werbrouck et al., *Physiol. Plant.* 1996, 98, 291).

WO 2008/008770 and WO 2009/086457 relate to 6,9-disubstituted purine derivatives, bearing 2-tetrahydropyranyl or 2-tetrahydrofuranyl moiety in position 9, and to their use in cosmetics as anti-inflammatory and antiaging components of skin care products.

The present invention provides for use of 6,8-disubstituted purine derivatives bearing 2-tetrahydropyranyl or 2-tetrahydrofuranyl moiety in cosmetic applications. Use of these compounds does not result in the undesired side effects such as cell proliferation and apoptosis, which are the problem of many adenine-based compounds known heretofore. The compounds exhibit very strong antioxidant properties.

The compounds of this invention have improved selectivities and efficiencies and lower toxicities than the known 6-(substituted amino)purines and 6,9-disubstituted purines.

DISCLOSURE OF THE INVENTION

The present invention provides 6,8-disubstituted-9-(heterocyclyl)purines of the general formula I

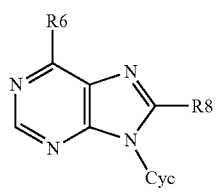

(I)

wherein

Cyc is heterocyclyl selected from the group consisting of 2-tetrahydropyranyl and 2-tetrahydrofuranyl;

R6 is —NH—$R_y$, $R_y$ is selected from the group consisting of:
$C_1$ to $C_8$ linear or branched alkyl, optionally substituted by at least one substituent selected from the group consisting of hydroxy, halogen, $C_1$ to $C_4$ alkoxy,
$C_2$ to $C_8$ linear or branched alkenyl, optionally substituted by at least one substituent selected from the group consisting of hydroxy, halogen, $C_1$ to $C_4$ alkoxy,
$C_3$ to $C_8$ cycloalkyl, optionally substituted by at least one substituent selected from the group consisting of hydroxy, halogen, $C_1$ to $C_4$ alkyl, $C_1$ to $C_4$ alkoxy,
benzyl, optionally substituted by at least one substituent selected from the group consisting of hydroxy, halogen, $C_1$ to $C_4$ alkyl, $C_1$ to $C_4$ alkoxy,
phenyl, optionally substituted by at least one substituent selected from the group consisting of hydroxy, halogen, $C_1$ to $C_4$ alkyl, $C_1$ to $C_4$ alkoxy,
furfuryl, optionally substituted by at least one substituent selected from the group consisting of hydroxy, halogen, $C_1$ to $C_4$ alkyl, $C_1$ to $C_4$ alkoxy, and R8 is selected from the group comprising amino, hydroxy, halogen, acyl, acyloxy, amido, alkoxy, benzyloxy, alkylamino, dialkylamino, alkenylamino, carbamoyl, carboxyl, cyano, hydrazino, —NHOH, —NHCONH$_2$, —NH—C(NH)NH$_2$, nitro, sulphanyl, alkylsulphanyl, sulpho, and alkyloxycarbonyl.

It is to be understood that the general formula encompasses the compounds as such, the compounds in the form of pharmaceutically acceptable salts with alkali metals, ammonium or amines, in the form of racemates or optically active isomers (when optically active atoms are present), as well as in the form of addition salts with acids.

Throughout this specification, unless specifically indicated otherwise, the generic substituents have the following meanings:
halogen denotes fluorine, bromine, chlorine, or iodine atom,
hydroxy denotes the group —OH;
sulphanyl denotes the group —SH;
amino denotes the group —NH$_2$;
hydrazino denotes the group —NHNH$_2$;
carbamoyl denotes the group —CONH$_2$;
cyano denotes the group —CN;
carboxyl denotes the group —COOH;
nitro denotes the group —NO$_2$;
sulpho denotes the group —SO$_2$R$_a$, wherein R$_a$ is hydrogen, alkyl, or alkenyl;
acyl denotes —C(O)R$_b$, wherein R$_b$ is alkyl, or alkenyl;
acyloxy denotes —O—C(O)R$_c$, wherein R$_c$ is hydrogen, alkyl or alkenyl;
alkoxy denotes the group —OR$_d$, wherein R$_d$ is alkyl;
alkylamino denotes the group —N(R$_e$)$_2$, wherein each R$_e$ is independently selected from hydrogen, alkyl, and alkenyl, each of which can be substituted by amino or hydroxyl substituent;
alkylsulphanyl denotes the group —SR$_f$, wherein R$_f$ is alkyl;
alkyloxycarbonyl denotes the group —C(O)OR$_g$, wherein R$_g$ is alkyl or alkenyl;
amido refers to group —C(O)N(R$_h$)$_2$, wherein each R$_h$ is independently hydrogen, alkyl, or alkenyl;
alkyl denotes a linear or branched alkyl chain containing 1 to 8 carbon atoms, which may be optionally substituted with one or more substituents selected from the group consisting of hydroxy, halogen, amino, sulphanyl, carboxyl, cyano, nitro, carbamoyl;
alkenyl denotes a linear or branched alkenyl chain containing 2 to 8 carbon atoms (preferably vinyl, allyl, 1-propenyl, 1-methylethenyl, but-1 to 3-enyl, pent-1 to 4-enyl, hex-1 to 5-enyl, hept-1 to 6-enyl, 3-methylbut-2-en-1-yl) which may be optionally substituted with one or more substituents selected from the group consisting of hydroxy, halogen, amino, sulphanyl, carboxyl, cyano, nitro, carbamoyl;

cycloalkyl denotes a monocyclic or polycyclic alkyl group containing 3 to 8 carbon atoms (preferably cyclopropyl, cyclobutyl, cyclopentyl, cyclohexyl, cycloheptyl or adamantyl), which may be optionally substituted with one or more substituents selected from the group consisting of hydroxy, halogen, amino, sulphanyl, carboxyl, cyano, nitro, carbamoyl.

$R_y$ is preferably selected from the group containing furfuryl, phenyl, benzyl, n-alkyl and n-alkenyl containing 4, 5 and 6 carbon atoms, (cyclohexyl)methyl and 3,3-dimethylallyl, which may be optionally substituted with one or more substituents selected from the group consisting of hydroxy, methoxy, methyl or amino group. In a preferred embodiment, $R_y$ is selected from the group consisting of furfuryl, phenyl, benzyl, 3-methylbut-2-en-1-yl, 4-hydroxy-3-methylbut-2-en-1-yl, cyclohexylmethyl, allyl or 3,3-dimethylallyl, which may be optionally substituted with one or more substituents selected from the group consisting of halogen, hydroxy, methoxy, methyl, amino, nitro or their combinations.

In another preferred embodiment, R8 is selected from the group consisting of amino, hydroxy, chloro, fluoro, bromo, amino($C_1$-$C_5$ alkyl)amino, hydroxy($C_1$-$C_5$ alkyl)amino, NHOH, $NHNH_2$, carboxy, nitro, sulfanyl, methylsulfanyl, and methoxy. R8 is more preferably amino or alkylamino.

The preferred 6,8-disubstituted-9-(heterocyclyl)purines of this invention of the general formula I are selected from the group consisting of: 6-furfurylamino-8-(amino, hydroxy, chloro, fluoro, bromo, amino($C_1$-$C_5$ alkyl)amino, hydroxy ($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-benzylamino-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-fluorobenzylamino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl) purine, 6-(3-fluorobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-fluorobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-bromobenzylamino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl) purine, 6-(3-iodobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-chlorobenzylamino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(3-chlorobenzylamino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl) purine, 6-(4-chlorobenzylamino)-8-(amino, hydroxy, chloro, fluoro, bromo, amino($C_1$-$C_5$ alkyl)amino, hydroxy ($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-methylbenzylamino)-8-(amino, hydroxy, chloro, fluoro, bromo, amino($C_1$-$C_5$ alkyl) amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-methoxybenzylamino)-8-(amino, hydroxy, chloro, fluoro, bromo, amino($C_1$-$C_5$ alkyl)amino, hydroxy($C_1$-$C_5$ alkyl) amino, NHOH, $NHNH_2$, carboxyl, nitro, sulphanyl, methylsulphanyl, methoxy)-9-(2-tetrahydropyranyl or 2-tetrahydrofuranyl)purine, 6-(3-methoxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-hydroxybenzylamino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl) purine, 6-(3-hydroxybenzylamino)-8-(amino, hydroxy, chloro, fluoro, bromo, amino($C_1$-$C_5$ alkyl)amino, hydroxy ($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-hydroxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-ethoxybenzylamino)-8-(amino, hydroxy, chloro, fluoro, bromo, amino($C_1$-$C_5$ alkyl)amino, hydroxy($C_1$-$C_5$ alkyl) amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-dichlorobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(5-chloro-2-fluorobenzylamino)-8-(amino, hydroxy, chloro, fluoro, bromo, amino($C_1$-$C_5$ alkyl)amino, hydroxy($C_1$-$C_5$ alkyl) amino, NHOH, $NHNH_2$, carboxyl, nitro, sulphanyl, methylsulphanyl, methoxy)-9-(2-tetrahydropyranyl or 2-tetrahydrofuranyl)purine, 6-(2,3,5-trifluorobenzylamino)-8-(amino, hydroxy, chloro, fluoro, bromo, amino($C_1$-$C_5$ alkyl) amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-chloro-2,6-difluorobenzylamino)-8-(amino, hydroxy, chloro, fluoro, bromo, amino($C_1$-$C_5$ alkyl)amino, hydroxy ($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-difluorobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-(trifluoromethyl)benzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,4-dihydroxybenzylamino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(3,5-dihydroxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-dimethoxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2,5-dimethoxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-hydroxy-4-methoxybenzylamino)-8-(amino, hydroxy, chloro, fluoro, bromo, amino($C_1$-$C_5$ alkyl)amino, hydroxy(C1-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-hydroxy-3-methoxybenzylamino)-8-(amino, hydroxy, chloro, fluoro, bromo, amino($C_1$-$C_5$ alkyl)amino, hydroxy(C1-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-hydroxy-3-methoxybenzylamino)-8-(amino, hydroxy, chloro, fluoro, bromo, amino ($C_1$-$C_5$ alkyl)amino, hydroxy(C1-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-hydroxy-5-methoxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2-aminobenzylamino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-aminobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-aminobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,4,5-trimethoxybenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2,4,5-trichlorobenzylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-cyclohexylamino-8-(amino, hydroxy, chloro, fluoro, bromo, amino($C_1$-$C_5$ alkyl)amino, hydroxy($C_1$-$C_5$ alkyl)amino, NHOH, NHNH2, carboxyl, nitro, sulphanyl, methylsulphanyl, methoxy)-9-(2-tetrahydropyranyl or 2-tetrahydrofuranyl)purine, 6-cyclopentylamino-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-cyclobutylamino-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-allylamino-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-diallylamino-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-isopentylamino-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,3-dimethylallylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-hydroxymethyl-3-methylallyl)amino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(Z)-(4-hydroxy-3-methylbut-2-en-1-ylamino)-8-(amino, hydroxy, chloro, fluoro, bromo, amino($C_1$-$C_5$ alkyl)amino, hydroxy(C1-C5 alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(E)-(4-hydroxy-3-methylbut-2-en-1-ylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-hydroxy-3-methylbutylamino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-propargylamino-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-anilino-8-(amino, hydroxy, chloro, fluoro, bromo, amino($C_1$-$C_5$ alkyl) amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-bromoanilino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-dichloroanilino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-difluoroanilino)-8-(amino, hydroxy, chloro, fluoro, bromo, amino($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3,5-dimethylanilino)-8-(amino, hydroxy, chloro, fluoro, bromo, amino ($C_1$-$C_5$ alkyl)amino, hydroxy($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(2,3-dimethoxyanilino)-8-(amino, hydroxy, chloro, fluoro, bromo, amino($C_1$-$C_5$ alkyl)amino, hydroxy ($C_1$-$C_5$ alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(3-chloroanilino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(2-chloro-5-fluoroanilino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(2-fluoroanilino)-8-(amino, hydroxy, chloro, fluoro, bromo, amino(C1-C5 alkyl)amino, hydroxy (C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(3-fluoroanilino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(2-methoxyanilino)-8-(amino, hydroxy, chloro, fluoro, bromo, amino (C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl) purine, 6-(3-methoxyanilino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(3-methylanilino)-8-(amino, hydroxy, chloro, fluoro, bromo, amino(C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl)purine, 6-(2,3,5-trifluoroanilino)-8-(amino, hydroxy, chloro, fluoro, bromo, amino (C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl) purine.

More preferred 6,8-disubstituted-9-(heterocyclyl)purines are: 6-furfurylamino-8-(amino, hydroxy, chloro, fluoro, bromo, amino(C1-C5 alkyl)amino, hydroxy(C1-C5 alkyl) amino, NHOH, $NHNH_2$, carboxyl, nitro, sulphanyl, methylsulphanyl, methoxy)-9-(2-tetrahydropyranyl or 2-tetrahydrofuranyl)purine, 6-(3-hydroxybenzylamino)-8-(amino, hydroxy, chloro, fluoro, bromo, amino(C1-C5 alkyl)amino, hydroxy(C1-C5 alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-hydroxybenzylamino)-8-(amino, hydroxy, chloro, fluoro, bromo, amino (C1-C5 alkyl)amino, hydroxy(C1-C5 alkyl)amino, NHOH, NHNH2, carboxyl, nitro, sulphanyl, methylsulphanyl, methoxy)-9-(2-tetrahydropyranyl or 2-tetrahydrofuranyl) purine, 6-(Z)-(4-hydroxy-3-methylbut-2-en-1-ylamino)-8-(amino, hydroxy, chloro, fluoro, bromo, amino(C1-C5 alkyl) amino, hydroxy(C1-C5 alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(E)-(4-hydroxy-3-methylbut-2-en-1-ylamino)-8-(amino, hydroxy, chloro, fluoro, bromo, amino(C1-C5 alkyl)amino, hydroxy (C1-C5 alkyl)amino, NHOH, $NHNH_2$, carboxyl, nitro, sulphanyl, methylsulphanyl, methoxy)-9-(2-tetrahydropyranyl or 2-tetrahydrofuranyl)purine, 6-(4-hydroxy-3-methylbutylamino)-8-(amino, hydroxy, chloro, fluoro, bromo, amino (C1-C5 alkyl)amino, hydroxy(C1-C5 alkyl)amino, NHOH, $NHNH_2$, carboxyl, nitro, sulphanyl, methylsulphanyl, methoxy)-9-(2-tetrahydropyranyl or 2-tetrahydrofuranyl) purine.

Generally, the most preferred 6,8-disubstituted-9-(heterocyclyl)purines are 8-hydroxymethylamino-6-furfurylamino-9-(2-tetrahydropyranyl)purine, 8-hydroxyethylamino-6-furfurylamino-9-(2-tetrahydropyranyl)purine and 8-hydroxypropylamino-6-furfurylamino-9-(2-tetrahydropyranyl)purine and their salts, wherein furfuryl group can optionally be substituted by one or more substituents selected from halogen, hydroxy, methoxy, methyl and their combinations.

Salts of 6,8-disubstituted-9-(heterocyclyl)purines of the present invention include salts with alkali metals, ammonium or amines, as well as in the form of addition salts with acids. When the compounds of this invention contain a chiral centre, then all enantiomers, mixtures of enantiomers and racemates fall within the framework of the present invention.

The 6,8-disubstituted-9-(heterocyclyl)purines have a wide range of biological activities, including antioxidant, anti-inflammatory, anti-senescent, pro-differentiation as well as other activities which are especially useful in pharmaceutical and cosmetic applications. Compositions containing the compounds of the invention possess growth-regulatory, differentiating, antisenescent and antiaging properties with improved selectivities and efficiencies and lower toxicities than analogues known heretofore.

This invention also provides 6,8-disubstituted-9-(heterocyclyl)purines of the general formula I for use as antioxidants for inhibiting improper and unsatisfactory metabolic processes in mammals or plants using either in vivo or in vitro techniques.

This invention also provides compounds 6,8-disubstituted-9-(heterocyclyl)purines of the general formula I for use as antioxidants for inhibiting lipid pre-oxidation in mammals or plants either in vivo or in vitro.

The compounds of the present invention thus can be used as medicaments. They can be used in methods of treatment of a variety of conditions in mammals, especially in humans. In particular, such conditions include skin conditions, such as acne, erythema, redness. The compounds may also be used as antineurodegenerative drugs, or in methods of suppression of immunostimulation (e.g., treatment of arthritis or suppression of transplant rejection). The compounds show in particular antioxidant, anti-inflammatory, anti-senescent properties.

This invention further provides 6,8-disubstituted-9-(heterocyclyl)purines of the general formula I or alkali metal salts, ammonium salts, amine salts thereof, and addition salts thereof with acids, in the form of racemates or optically active isomers, for preparation of pharmaceutical compositions.

The compounds of the present invention can be used in cosmetics. Cosmetic uses of these compounds and their salts include inhibition, delaying, or reducing the adverse effects of aging and senescence of cells, especially human epidermal cells such as keratinocytes or fibroblasts; the cosmetic uses also include improving the overall appearance and condition of the skin, including age-related changes and changes that may not be closely related to aging (e.g., acne, erythema, redness, and the like).

This invention further provides cosmetic compositions comprising one or more 6,8-disubstituted-9-(heterocyclyl) purines of formula I in a cosmetically acceptable carrier system.

This invention also provides use of the compounds of formula I for inhibiting cell senescence and aging in mammals or plants comprising application of an effective amount of the 6,8-disubstituted-9-(heterocyclyl)purines using either in vivo or in vitro techniques.

This invention also provides use for inhibiting or delaying the adverse effects of aging and/or improving the cosmetic appearance of mammalian cells, especially human skin cells, by applying an effective of the 6,8-disubstituted-9-(heterocyclyl)purines to the mammalian cells.

This invention further provides methods for rejuvenation of cell, stimulation of cell proliferation and/or differentiation in an organism by application of an effective amount of the 6,8-disubstituted-9-(heterocyclyl)purines of this invention.

As used herein, ameliorating the adverse effect of aging of mammalian cells means that the development of the morphological changes that normally occur with aging in normal mammalian cells in vitro or in vivo is slowed, reversed, and/or delayed. The adverse effects of aging also include age-related changes in gene expression and protein biosynthesis. The ameliorative effect referred to herein is achieved without substantially increasing the growth rate or total proliferative capacity of the cells that are treated. Ameliorating the adverse effects of aging on cells may be detected as a delay or reversal of the onset of age-related morphological and phenotypical changes that normally occur with aging of the cells. Age-related changes in vivo include changes in mammalian tissues, such as the development of, or increase in number or depth of, wrinkles, lines, sagging skin, discolorations, blotchiness, leathery, and/or yellowed appearance associated with the cosmetic appearance of the skin as well as the associated changes in the structural and functional integrity of the tissue. The 6,8-disubstituted-9-(heterocyclyl)purines of this invention are effective in improving the overall appearance and condition of the skin, including age-related changes and changes that may not be closely related to aging (e.g., acne, erythema, redness, and the like).

Compositions containing one or more of the 6,8-disubstituted-9-(heterocyclyl)purines of the present invention are useful for treating senescing and aging cells in mammals and plants.

The 6,8-disubstituted-9-(heterocyclyl)purines of the present invention can also be used as growth regulators in tissue cultures for stimulation of proliferation, morphogenesis, and senescence.

The 6,8-disubstituted-9-(heterocyclyl)purines of the present invention can also be used as cell division and differentiation factors of plant, mammal, microorganisms, yeast, and fungal cells.

The 6,8-disubstituted-9-(heterocyclyl)purines of the present invention can also be used for preparation of affinity absorption matrices, immobilised enzymes for process control, immunoassay reagents, diagnostic samples, as well as compounds and oligonucleotides, labelled by $^{14}C$, $^3H$, avidin, biotin, or the like.

The compounds of this invention, can also be used for preparation of compositions suitable for use with plant and mammalian embryonic stem cells and embryo (especially oocytes) cloning.

Suitable routes for administration include oral, rectal, topical (including dermal, ocular, buccal and sublingual), vaginal and parenteral (including subcutaneous, intramuscular, intravitreous, intravenous, intradermal, intrathecal and epidural).

The therapeutic and/or cosmetic compositions generally comprise about 1% to about 95% of the active ingredient.

Single-dose forms of administration preferably comprise about 20% to about 90% of the active ingredient and administration forms which are not single-dose preferably comprise about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical and cosmetic compositions of the present invention are prepared in a manner known per se, for example by means of conventional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The compositions can be sterilized and/or comprise excipients, for example, preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, carboxymethylcellulose, dextran, polyvinylpyrrolidone or gelatine.

Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms (e., lauric acid, tridecylic acid, myristic acid, pentadecylic acid, palmitic acid, margaric acid, stearic acid, acid, arachidonic acid, behenic acid, and the like) or corresponding unsaturated acids (e.g., oleic acid, elaidic acid, euric acid, brasidic acid or linoleic acid). Other additional ingredients known in the art can be included if desired (e.g., antioxidants such as vitamin E, β-carotene, or 3,5-di-tert-butyl-4-hydroxytoluene, and the like). The alcohol component of these fatty acid esters generally contains no more than about 6 carbon atoms and can be mono- or polyhydric. Mono-, di-, or trihydric alcohols such as methanol, ethanol, propanol, butanol, or pentanol, or isomers thereof, can be used; glycols and glycerols are generally preferred. Fatty acid esters can therefore include, for example, ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris), and/or "Miglyol 812" (triglyceride of saturated fatty acids of chain length C8 to C12 from Hüls AG, Germany), and in particular vegetable oils, such as cottonseed oil, almond oil, olive oil, castor oil, sesame oil, soybean oil and, in particular, groundnut oil as well as mixtures thereof.

The preparation of the compositions intended for human use should, of course, be carried out in the customary and approved manner under sterile conditions, and maintained under appropriate conditions up to and including the time of use.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidone, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidone, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, can also be in the form hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol's or fatty acid esters of ethylene glycol or propylene glycol, it being likewise possible to add stabilisers and detergents such as, for example, the polyethylene sorbitan fatty acid ester type.

Other oral forms of administration include, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms include pulverulent or liquid concentrates for preparing shakes, beverages, and the like. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate, stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example, glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example, hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also can contain emulsifiers and/or additives mentioned in connection with the ointments which increase uptake of water.

Creams are oil-in-water emulsions, which comprise more than 50% of water. Oily bases used are, in particular, fatty alcohols, for example, lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example, sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example, titanium oxide or zinc oxide, and furthermore talc and/or aluminium silicates, which have the task of binding the moisture or secretions present.

Foams (i.e., liquid oil-in-water emulsions packaged in aerosol form) can be administered from pressurised containers. Propellant gases include halogenated hydrocarbons, such as polyhalogenated alkanes such as dichlorofluoromethane and dichlorotetrafluoroethane, or, preferably, non-halogenated gaseous hydrocarbons, air, $N_2O$, or carbon dioxide. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols (e.g., glycerol, glycols, polyethylene glycol) and re-oiling substances, such as fatty acid esters with lower polyethylene glycols (e.g., lipophilic substances soluble in the aqueous mixture) to substitute the fatty substances removed from the skin with the ethanol, and, if necessary or desired, other excipients and additives, are admixed.

The present invention further provides veterinary compositions comprising at least one active ingredient as above defined together with a veterinary carrier therefor. Veterinary carriers are materials for administering the composition and may be solid, liquid, or gaseous materials, which are inert or acceptable in the veterinary art and are compatible with the active ingredient. These veterinary compositions may be administered orally, parenterally, or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example, a human requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
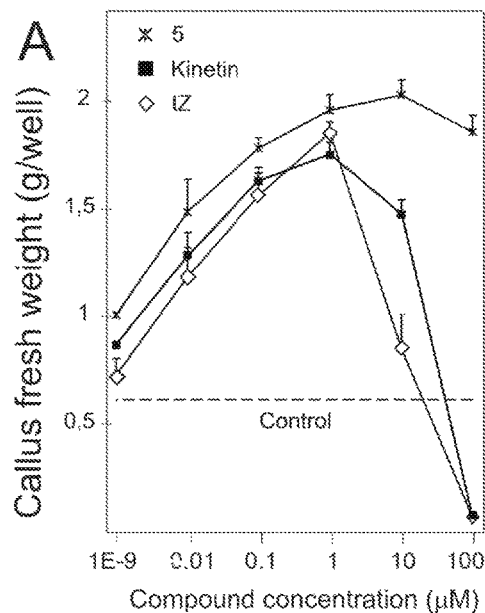
FIG. 1. Effect of compound 5 on callus growth. Kinetin and trans-zeatin (tZ) are used as standards. Error bars show standard deviation of the mean for 5 replicate determination. Control is the value for the treatment without any cytokinin.

The following examples serve to illustrate the invention without limiting the scope thereof. Unless otherwise stated, all percentages and the like amounts are based on weight.

The starting materials may be obtained from commercial sources (Sigma, Aldrich, Fluka, etc.) or can be prepared as described below.

Evaporations were carried out on a rotary evaporator under vacuum at temperatures below 80° C. Melting points were determined on a Koffler block and are uncorrected. Purity of prepared compounds was confirmed by high performance liquid chromatography (HPLC) (Beckman Gold system). The samples were dissolved in methanol, applied to LiChroCARD 250×4 mm column filled with Purospher RP-18e, 5 μm (Merck) and the separated constituents were eluted by isocratic elution using a mixture of methanol (HPLC grade) and $AcOH/AcONH_4$ buffer (pH=3,4; 40 mM; with addition of 5% MeOH) at a flow rate of 0.5 ml/min. Eluting compounds were detected by scanning the UV absorbance of the eluate between 200 and 300 nm. The $^1$H-NMR spectra (σ ppm; J, Hz) were measured on Varian Unity 300 (300 MHz) instruments. All spectra were obtained at 25° C. using tetramethylsilane as internal standard. Electron impact mass spectra m/z (rel. %, composition, deviation) were measured on a VG 7070E spectrometer (70 eV, 200° C., direct inlet). Quadrupole mass spectra were measured on a Micromass ZMD detector with electrospray ionization. Samples for MS were dissolved in methanol+5% HCOOH. Merck silica gel PharmPrep 60 CC (40-63 μm) was used for column chromatography. 6-Alkylamino-8-substituted-9-(tetrahydropyran-2-yl)-9H-purines were prepared using four-step reaction scheme, which included: tetrahydropyranylation of 6-chloropurine, reaction of 6-chloro-9-(tetrahydropyran-2-yl)-9H-purine with appropriate alkenyl- or arylalkylamine in alcohole and a base, introduction of a halogen atom into the position 8 and substitution of the halogen with a nucleophile (amine or alcoholate) to afford the 6,8-disubstituted-9-(heterocyclyl)purine.

Example 1

Synthesis of 6-chloro-9-(tetrahydropyran-2-yl)-9H-purine

The compound was prepared from 6-chloropurine according to the literature (Taddei et al., Org. Biomol. Chem. 2004, 2, 665). A mixture of 6-chloropurine (20.0 g, 129 mmol), p-toluenesulfonic acid (0.23 g, 1.85 mmol), 3,4-dihydro-2H-pyran (14.5 ml, 159 mmol) in tetrahydrofuran (175 ml) was refluxed under argon at 84° C. for 22 h. After cooling, concentrated ammonia (5 ml) was added, undissolved particles were filtered off and the filtrate evaporated to dryness. The yellowish oil was dissolved in ethyl acetate (250 ml) and extracted with brine (75 ml), water (2×75 ml) and then dried over sodium sulfate. The organic extracts were concentrated in vacuo into an yellow oil that was extracted with boiling cyclohexane (cca 250 ml). Light yellow cyclohexane extract was separated from the undissolved orange rest by decantation. The extraction procedure was repeated twice with 150 ml cyclohexane. The cyclohexane extracts were cooled in a fridge overnight to precipitate colourless crystals. Yield: 19.1 g, 62%. M.p.: 68° C. $^1$H NMR (300 MHz, DMSO-$d_6$): δ 1.61 (2H, m, THP), 1.76 (1H, m, THP), 2.00 (2H, m, THP), 2.34 (1H, m, THP), 3.73 (1H, m, THP H4'), 4.03 (1H, dm, J=11 Hz, THP H3'), 5.80 (1H, dd, J=2.3, 11 Hz, THP H2'), 8.81 (1H, s, H8), 8.92 (1H, s, H2).

Examples 2

Syntheses of 6-alkylamino/aralkylamino-9-(tetrahydropyran-2-yl)-9H-purines

6-Furfurylamino-9-(tetrahydropyran-2-yl)-9H-purine

6-Chloro-9-(tetrahydropyran-2-yl)-9H-purine (Ex 1.) (3.89 g, 16 mmol) was dissolved in 1-propanol (30 ml). Furfurylamine (2.9 ml, 33 mmol) and triethylamine (4.3 ml, 31 mmol) were added. The solution was stirred at room temperature over night. Crystals (the first portion) were filtered off, washed with cold 1-propanol and then thoroughly with water. The filtrate was heated at 70° C. for 3 h, cooled and left in a refrigerator over night. Crystals (the second portion) were filtered off, washed with cold 1-propanol and then thoroughly with water. Filtrate was partly evaporated and after crystallization in a refrigerator was obtained the third portion of product. The off white crystalline product was dried in dessiccator with $P_2O_5$. Yield: 3.46 g, 71%. M. p.: 141-143° C. HPLC $R_t$=9.1 min (70% $CH_3OH$+30% buffer); UV (70% $CH_3OH$+30% buffer) $\lambda_{max}$ 267 nm, $\lambda_{min}$ 235 nm. MS ESI+(CV 18) m/z (rel. %): 300 $[M+H]^+$ (100), 322 $[M+Na]^+$ (36), 621 $[2M+Na]^+$ (38); (CV 38) m/z (rel. %): 216 $[C_{10}H_9N_5O+H]^+$ (100), 322 $[M+Na]^+$ (56), 238 $[C_{10}H_9N_5O+Na]^+$ (22), 300 $[M+H]^+$ (21).

6-(3-methylbut-2-en-1-ylamino)-9-(tetrahydropyran-2-yl)-9H-purine

6-Chloro-9-(tetrahydropyran-2-yl)-9H-purine (Ex 1.) (4.02 g, 17 mmol) was dissolved in 2-propanol (47 ml). 3-Methylbut-2-en-1-amine hydrochloride (3.08 g, 25 mmol) and triethylamine (5.9 ml, 42 mmol) were added. The solution was stirred and heated at 65° C. for 14 h. The mixture was evaporated to dryness, dissolved in 50 ml of chloroform and extracted with 30 ml of water three times. Chloroform layer was dried with $MgSO_4$ and evaporated. The crude product crystallizes after drying in desiccator with $P_2O_5$ (4.56 g, 94%). The solid was crystallized from ethyl acetate (8 ml) to give white crystals. Yield: 2.86 g, 73%. M. p.: 95-98° C. MS ESI+(CV 18) m/z (rel. %): 288 $[M+H]^+$ (100), 310 $[M+Na]^+$ (37), 597 $[2M+Na]^+$ (28); (CV 38) m/z (rel. %): 204 $[C_{10}H_{13}N_5+H]^+$ (100), 310 $[M+Na]^+$ (37), 288 $[M+H]^+$ (19), 226 $[C_{10}H_{13}N_5+Na]^+$ (17).

(E)-6-(4-Hydroxy-3-methylbut-2-en-1-ylamino)-9-(tetrahydropyran-2-yl)-9H-purine Prepared in the same way like 6-furfurylamino-9-(tetrahydropyran-2-yl)-9H-purine (Ex 2.1). White crystals. Yield: 76%. M. p.: 111-116° C. (ethyl acetate). HPLC $R_t$=10.4 min (55% $CH_3OH$+45% buffer); $R_t$=8.6 min (60% $CH_3OH$+40% buffer); UV (55% $CH_3OH$+45% buffer) $\lambda_{max}$ 268 nm, $\lambda_{min}$ 231 nm. MS ESI+(CV 20) m/z (rel. %): 304 $[M+H]^+$ (100), 326 $[M+Na]^+$ (17), 220 $[C_{10}H_{13}N_5O+H]^+$ (16).

(Z)-6-(4-Hydroxy-3-methylbut-2-en-1-ylamino)-9-(tetrahydropyran-2-yl)-9H-purine (Z)-4-Amino-1-methylbut-2-en-1-ol (0.87 g, 8.6 mmol) was dissolved in 1-propanol (14 ml). Triethylamine (0.95 ml, 6.9 mmol) and 6-chloro-9-(tetrahydropyran-2-yl)purine (Ex 1.) (1.64 g, 6.9 mmol) were added and the mixture heated at 45° C. for 6 h. After cooling, the mixture was filtered, filtrate partly evaporated and purified by column chromatography (60.3 g of silica gel, mobile phase chloroform:acetone 4:1, flow rate 7.5 ml/min. The product was a light yellow viscous substance which starts to crystallize after two weeks of drying over $P_2O_5$ in a vacuum desiccator. M. p.: 127-131° C. Yield 1.50 g (72%). MS ESI+(CV 18) m/z (rel. %): 304 $[M+H]^+$ (100), 326 $[M+Na]^+$ (17); (CV 38) m/z (rel. %): 220 $[C_{10}H_{13}N_5O+H]^+$ (100), 326 $[M+Na]^+$ (32), 242 $[C_{10}H_{13}N_5O+Na]^+$ (29).

6-Benzylamino-9-(tetrahydropyran-2-yl)-9H-purine

6-Chloro-9-(tetrahydropyran-2-yl)-9H-purine (Ex 1.) (2.52 g, 10.6 mmol) was dissolved in 2-propanol (13.5 ml). Benzylamine (1.4 ml, 12.8 mmol) and triethylamine (1.5 ml, 10.5 mmol) were added. The solution was stirred and heated at 40° C. for 8 h. The mixture was evaporated to dryness, dissolved in 20 ml of ethyl acetate and extracted with 15 ml of water twice. Ethyl acetate layer was dried with $Na_2SO_4$ and evaporated. The crude product crystallizes after drying in desiccator with $P_2O_5$ to give (2.14 g, 66%). white crystals, m. p.: 124-127° C. MS ESI+(CV 10) m/z (rel. %): 310 $[M+H]^+$ (100); (CV 40) m/z (rel. %): 226 $[C_{12}H_{11}N_5+H]^+$ (100), 310 $[M+H]^+$ (13).

Examples 3

Syntheses of 8-halogen-6-alkylamino/aralkylamino-9-(tetrahydropyran-2-yl)-9H-purines

8-Chloro-6-furfurylamino-9-(tetrahydropyran-2-yl)-9H-purine

The compound was prepared from 6-furfurylamino-9-(tetrahydropyran-2-yl)-9H-purine (Ex 2.1) applying the procedure described in literature (Nolsøe et al., Synth. Commun. 1998, 28, 4303; Gunji, Helv. Chim. Acta 2000, 83, 1331). 20 mL (36 mmol) of commercially available 1.8 M lithium diisopropylamide solution was under argon dissolved in 30 mL dry tetrahydrofuran cooled to −78° C. The mixture was treated dropwise over 20 min with solution of 3.64 g (12.2 mmol) 6-furfurylamino-9-(tetrahydropyran-2-yl)-9H-purine in 35 mL dry tetrahydrofurane, then the reaction mixture was stirred at −78° C. for 2 h. After this time, 4.7 mL (36.6 mmol) benzensulfonylchloride was added dropwise over 20 min, and the mixture farther stirred for 3 h. Without loading the bottle with argon, 30 mL 20% $NH_4Cl$ solution was added dropwise. The cooling bath was removed and the mixture left to get room temperature. The layers were separated. The aqueous layer was extracted with diethyl ether (2×27 mL). The combined organic layers were washed with 65 mL brine and water (2×50 mL), dried with $Na_2SO_4$, and evaporated. The crude product was voided of benzensulfonamide by crystallization from ethyl acetate and ethanol. The rest after crystallization was evaporated and purified by column chromatography (silica gel; mobile phase chloroform:acetone 95:5). The product was recrystallized from methanol/diethyl ether. Light beige crystals.

Yield: 2.80 g, 69%. M.p.: 110-114° C. HPLC $R_t$=17.3 min (60% $CH_3OH$+40% buffer) (flow rate 0.6 ml/min). MS ESI+(CV 10) m/z (rel. %): 334 $[M+H]^+$ (100), 336 $[M+H]^+$ (51); (CV 20) m/z (rel. %): 334 $[M+H]^+$ (100), 336 $[M+H]^+$ (34), 250 $[C_{10}H_5ClN_5O+H]^+$ (53), 252 $[C_{10}H_5ClN_5O+H]^+$ (19). $^1H$ NMR (300 MHz, DMSO-$d_6$): δ 1.62 (3H, mm, THP, H4', 5'), 1.85 (1H, dd, J=12.6, 2.4 Hz, THP H5'), 1.97 (1H, d, J=11.2 Hz, THP H4'), 2.89 (1H, qq, J=11.8, 4.1 Hz, THP H3'), 3.66 (1H, tt, J=11.3, 3.6 Hz THP H6'), 4.02 (1H, d, J=11.3 Hz, THP H6'), 4.66 (2H, s, —NH—$CH_2$-Fur, 5.63 (1H, d, J=10.6 Hz, THP H2'), 6.22 (1H, d, J=2.6 Hz, Fur H3'), 6.35 (1H, m, Fur H4'), 7.53 (1H, m, Fur H5'), 8.26 (1H, s, H2), 8.42 (1H, bs, $N^6H$). $^{13}C$ NMR (300 MHz, DMSO-$d_6$): δ 22.58 (THP C4'), 24.46 (THP C5'), 28.09 (THP C3'), 36.51 (—NH—$CH_2$-Fur, 68.10 (THP C6'), 83.11 (THP C2'), 106.71 (Fur C3'), 110.43 (Fur C4'), 117.87 (C5), 136.32 (C8), 141.87 (Fur C5'), 150.16 (C4), 152.62 (Fur C2'), 152.73 (C2), 153.11 (C6).

8-Bromo-6-furfurylamino-9-(tetrahydropyran-2-yl)-9H-purine

The compound was prepared from 6-furfurylamino-9-(tetrahydropyran-2-yl)-9H-purine (Ex 2.1) applying the procedure described in literature (Nolsøe et al., Synth. Commun. 1998, 28, 4303; Gunji, Helv. Chim. Acta 2000, 83, 1331). 0.93 g (3.1 mmol) of (2.1) was under argon dissolved in 10 ml dry tetrahydrofuran and cooled to −78° C. The solution was treated dropwise over 10 min with 3.7 ml (7.5 mmol) of lithium diisopropylamide solution. The reaction mixture was then stirred at −78° C. for 1 h. After this time, a solution of 2.7 g (8.2 mmol) tetrabromomethane in 3.5 ml of dry tetrahydrofuran was added dropwise over 10 min, and the mixture further stirred for 1 h. Without loading the bottle with argon, 9 ml of 20% NH$_4$Cl solution was added dropwise. The cooling bath was removed and the mixture left to get room temperature. The layers were separated. The organic layer was washed with 15 ml brine and water (2×15 ml), dried with MgSO$_4$, and evaporated. The crude product was purified by column chromatography (mobile phase hexanes:ethyl acetate 3:2. After column chromatography, the collected fractions were concentrated in vacuo and dried in desiccator with P$_2$O$_5$ for 4 days to give light beige-brown powder. Yield: 0.44 g, 37%. M. p.: 108-112° C. (cryst. from ethyl acetate). HPLC R$_t$=11.5 min (75% CH$_3$OH+25% buffer). UV (75% CH$_3$OH+25% buffer) $\lambda_{max}$ 272 nm, $\lambda_{min}$ 238 nm. MS ESI+(CV 10) m/z (rel. %): 380 [M+H]$^+$ (100), 378 [M+H]$^+$ (86), 294 [C$_{10}$H$_8$BrN$_5$O+H]$^+$ (9); 296 [C10H8BrN5O+H]$^+$ (8); (CV 30) m/z (rel. %): 296 [C10H8BrN5O+H]$^+$ (100), 294 [C10H8BrN5O+H]$^+$ (93), 228 [C6H5BrN5]$^+$ (28), 226 [C6H5BrN5]$^+$ (27), 380 [M+H]$^+$ (10), 378 [M+H]$^+$ (9). $^1$H NMR (300 MHz, DMSO-d$_6$): δ 1.56 (1H, m, THP H5'), 1.65 (2H, mm, THP H4', 5'), 1.85 (1H, dd, J=12.9, 2.4, THP H3'), 1.99 (1H, d, J=11.8, THP H4'), 3.00 (1H, qq, J=11.8, 4.2, THP H3'), 3.65 (1H, tt, J=11.3, 3.6, THP H6'), 4.04 (1H, d, J=11.3, THP H6'), 4.67 (2H, bs, NH—CH$_2$-Fur, 5.61 (1H, dd, J=11.2, 2.0, THP H2'), 6.23 (1H, d, J=3.2, Fur H3'), 6.35 (1H, m, Fur H4'), 7.53 (1H, m, Fur H5'), 8.24 (1H, s, H2), 8.42 (1H, bs, N$^6$H). $^{13}$C-NMR (300 MHz, DMSO-d$_6$): δ 22.56 (THP C4'), 24.37 (THP C5'), 27.98 (THP C3'), 36.44 (NH—CH$_2$-Fur, 68.04 (THP C6'), 84.10 (THP C2'), 106.62 (Fur C3'), 110.34 (Fur C4'), 119.46 (C5), 125.88 (C8), 141.76 (Fur C5'), 150.13 (C4), 152.45 (C2), 152.56 (Fur C2'), 152.95 (C6).

8-Iodo-6-furfurylamino-9-(tetrahydropyran-2-yl)-9H-purine

The compound was prepared from 6-furfurylamino-9-(tetrahydropyran-2-yl)-9H-purine (Ex 2.1) applying the procedure described in literature (Nolsøe et al., *Synth. Commun.* 1998, 28, 4303; Gunji, *Helv. Chim. Acta* 2000, 83, 1331). 2.12 g (7.1 mmol) of (2.1) was under argon dissolved in 35 ml dry tetrahydrofuran and cooled to −78° C. The solution was treated dropwise over 16 min with 21 ml (42 mmol) of lithium diisopropylamide solution. The reaction mixture was then stirred at −78° C. for 70 min. After this time, a solution of 12.5 g (49 mmol) iodine in 8.0 ml of dry tetrahydrofuran was added dropwise, and the mixture further stirred for 1 h. The reaction was quenched, without loading the bottle with argon, with a solution of Na$_2$S$_2$O$_3$.5.H$_2$O (24 g) added dropwise. The cooling bath was removed and the mixture left to get room temperature. The layers were separated. The organic layer was washed with 15 ml brine and water (2×40 ml). Water layers were reextracted with ethyl acetate (2×40 ml). Combined organic layers were dried with MgSO$_4$, and evaporated. The crude product was purified by column chromatography (mobile phase hexanes:ethyl acetate 3:2. After column chromatography, the collected fractions were concentrated in vacuo and dried in desiccator with P$_2$O$_5$ to give light beige powder. Yield: 2.00 g, 66%. M. p.: 130-134° C. (cryst. from ethyl acetate). HPLC R$_t$=6.0 min (90% CH$_3$OH+10% buffer), R$_t$=8.6 min (80% CH$_3$OH+20% buffer). UV (80% CH$_3$OH+20% buffer) $\lambda_{max}$ 276 nm, $\lambda_{min}$ 240 nm. MS ESI+(CV 10) m/z (rel. %): 426 [M+H]$^+$ (100). $^1$H NMR (300 MHz, DMSO-d$_6$): δ 1.56 (1H, m, THP H5'), 1.64 (2H, mm, THP H4', 5'), 1.81 (1H, dd, J=12.9, 2.4, THP H3'), 1.99 (1H, d, J=11.8, THP H4'), 3.09 (1H, qq, J=11.8, 3.3, THP H3'), 3.64 (1H, tt, J=11.3, 2.9, THP H6'), 4.05 (1H, d, J=11.3, THP H6'), 4.65 (2H, bs, NH—CH$_2$-Fur, 5.54 (1H, dd, J=11.3, 2.2, THP H2'), 6.21 (1H, d, J=2.9, Fur H3'), 6.35 (1H, m, Fur H4'), 7.53 (1H, m, Fur H5'), 8.17 (1H, s, H2), 8.42 (1H, bs, N$^6$H). $^{13}$C-NMR (300 MHz, DMSO-d$_6$): δ 22.67 (THP C4'), 24.39 (THP C5'), 28.07 (THP C3'), 36.41 (NH—CH$_2$-Fur, 68.01 (THP C6'), 85.77 (THP C2'), 101.75 (C8), 106.57 (Fur C3'), 110.34 (Fur C4'), 122.07 (C5), 141.72 (Fur C5'), 150.16 (C4), 152.03 (C2), 152.67 (Fur C2'), 152.80 (C6).

8-Chloro-6-(3-methylbut-2-en-1-ylamino)-9-(tetrahydropyran-2-yl)-9H-purine

The compound was prepared from 6-(3-methylbut-2-en-1-ylamino)-9-(tetrahydropyran-2-yl)-9H-purine (Ex 2.2) applying the procedure described in literature (Nolsøe et al., *Synth. Commun.* 1998, 28, 4303; Gunji, *Helv. Chim. Acta* 2000, 83, 1331). 2.08 g (7.2 mmol) of (2.2) was under argon dissolved in 30 ml dry tetrahydrofuran and cooled to −78° C. The solution was treated dropwise over 30 min with 22 ml (44 mmol) of lithium diisopropylamide solution. The reaction mixture was then stirred at −78° C. for 1 h. After this time, a solution of 3.43 g (14.5 mmol) hexachloroethane in 15.0 ml of dry tetrahydrofuran was added dropwise over 20 min, and the mixture further stirred for 1 h. Without loading the bottle with argon, 30 ml of 18% NH$_4$Cl solution was added dropwise. The cooling bath was removed and the mixture left to get room temperature. The layers were separated. The organic layer was washed with 40 ml brine and water (2×25 ml), dried with Na$_2$SO$_4$, and evaporated. The crude product was purified by column chromatography (mobile phase hexanes:ethyl acetate 3:2, on TLC chromatogram R$_f$=0.14). After column chromatography, the collected fractions were concentrated in vacuo. Light beige crystals. Yield: 1.53 g, 66%. M. p.: 118-120° C. (cryst. from hexanes: ethyl acetate 3:2). HPLC R$_t$=14.5 min (80% CH$_3$OH+20% buffer). MS ESI+(CV 10) m/z (rel. %): 322 [M+H]$^+$ (100), 324 [M+H]$^+$ (31); (CV 35) m/z (rel. %): 238 [C$_{10}$H$_{12}$ClN$_5$+H]$^+$ (100), 240 [C$_{10}$H$_{12}$ClN$_5$+H]$^+$ (31), 182 [C6H5ClN$_{5}$]$^+$ (17), 170 [C5H4ClN$_{5}$]$^+$ (17), 322 [M+H]$^+$ (12). $^1$H NMR (300 MHz, DMSO-d$_6$): δ 1.55 (3H, mm, THP, H4', 5'), 1.66 (3H, s, —CH$_3$), 1.68 (3H, s, —CH$_3$), 1.84 (1H, d, J=13.0 Hz, THP H3'), 1.97 (1H, d, J=11.0 Hz, THP H4'), 2.89 (1H, qq, J=12.4, 3.4 Hz, THP H3'), 3.65 (1H, tt, J=11.3, 3.6 Hz THP H6'), 4.01 (1H, m, THP H6'), 4.04 (2H, bs, —NH—CH$_2$—), 5.26 (1H, t, J=6.6 Hz, —CH$_2$—CH=), 5.62 (1H, d, J=11.7 Hz, THP H2'), 8.07 (1H, bs, N$^6$H), 8.22 (1H, s, H2). $^{13}$C NMR (300 MHz, DMSO-d$_6$): δ 17.74 (—CH$_3$), 22.49 (THP C4'), 24.36 (THP C5'), 25.30 (—CH$_3$), 27.98 (THP C3'), 37.56 (—NH—CH$_2$—), 68.00 (THP C6'), 82.94 (THP C2'), 117.72 (C5), 121.72 (—CH=), 133.30 (=C<), 135.74 (C8), 149.41 (C4), 152.77 (C2), 153.00 (C6).

8-Bromo-6-(3-methylbut-2-en-1-ylamino)-9-(tetrahydropyran-2-yl)-9H-purine

The compound was prepared from 6-(3-methylbut-2-en-1-ylamino)-9-(tetrahydropyran-2-yl)-9H-purine (Ex 2.2) applying the procedure described in literature (Nolsøe et al., *Synth. Commun.* 1998, 28, 4303; Gunji, *Helv. Chim. Acta* 2000, 83, 1331). 3.00 g (10.4 mmol) of (2.2) was under argon dissolved in 30 ml dry tetrahydrofuran and cooled to −78° C. The solution was treated dropwise over 40 min with 31 ml (62 mmol) of lithium diisopropylamide solution. The reaction mixture was then stirred at −78° C. for 1 h. After this time, a solution of 8.50 g (25.6 mmol) tetrabromomethane in 8.0 ml was added dropwise over 20 min, and the mixture farther stirred for 1 h. Without loading the bottle with argon, 50 ml of 20% $NH_4Cl$ solution was added dropwise. The cooling bath was removed and the mixture left to get room temperature. The layers were separated. The organic layer was washed with 50 ml brine and water (2×50 ml), dried with $Na_2SO_4$, and evaporated. The crude product was purified by column chromatography (mobile phase hexanes:ethyl acetate 3:2, on TLC chromatogram $R_f$=0.17). After column chromatography, the collected fractions were concentrated in vacuo into app. volume 50 ml and let to crystallize in refrigerator over night. Light beige crystals were filtered off, washed with hexanes and dried. Yield: 2.28 g, 60%. M. p.: 125-128° C. HPLC $R_t$=14.2 min (80% $CH_3OH$+20% buffer). UV (70% $CH_3OH$+30% buffer) $\lambda_{max}$ 274 nm, $\lambda_{min}$ 235 nm. MS ESI+(CV 20) m/z (rel. %): 368 $[M+H]^+$ (100), 366 $[M+H]^+$ (98), 282 $[C_{10}H_{11}BrN_5+H]^+$ (30), 284 $[C_{10}H_{11}BrN_5+H]^+$ (28). $^1$H NMR (300 MHz, DMSO-$d_6$): δ 1.55 (3H, mm, THP, H4', 5'), 1.65 (3H, s, —$CH_3$), 1.68 (3H, s, —$CH_3$), 1.82 (1H, d, J=12.8 Hz, THP H3'), 1.97 (1H, m, THP H4'), 2.99 (1H, qq, J=12.1, 4.0 Hz, THP H3'), 3.63 (1H, tt, J=10.8, 3.6 Hz THP H6'), 4.01 (1H, m, THP H6'), 4.05 (2H, bs, —NH—$CH_2$—), 5.26 (1H, t, J=6.4 Hz, —$CH_2$—CH=), 5.59 (1H, d, J=10.9 Hz, THP H2'), 8.08 (1H, bs, $N^6$H), 8.20 (1H, s, H2). $^{13}$C NMR (300 MHz, DMSO-$d_6$): δ 17.74 (—$CH_3$), 22.56 (THP C4'), 24.36 (THP C5'), 25.30 (—$CH_3$), 27.96 (THP C3'), 37.56 (—NH—$CH_2$—), 68.01 (THP C6'), 84.02 (THP C2'), 119.43 (C5), 121.73 (—CH=), 125.36 (C8), 133.27 (=C<), 149.80 (C4), 152.58 (C2), 153.00 (C6).

(E)-8-Chloro-6-(4-hydroxy-3-methylbut-2-en-1-ylamino)-9-(tetrahydropyran-2-yl)-9H-purine (E)-6-(4-hydroxy-3-methylbut-2-en-1-ylamino)-9-(tetrahydropyran-2-yl)-9H-purine (Ex 2.3) (0.93 g, 3.1 mmol) was dissolved under argon in dry tetrahydrofuran (15 ml). The solution was treated dropwise with commercially available 1.8 M lithium diisopropylamide solution (15 ml, 30 mmol). The reaction mixture was stirred at −78° C. for 1.5 h. After this time, solution of hexachloroethane (2.14 mL, 9.0 mmol) in dry tetrahydrofuran (6 ml) was added dropwise over 12 min to the reaction mixture, which was then stirred for 1 h. Then, 20% $NH_4Cl$ (20 ml) was added dropwise. After spontaneous warming to room temperature, the layers were separated. The aqueous layer was extracted with ethyl acetate (3×10 mL). Collected organic layers were dried with $Na_2SO_4$, and evaporated. The crude product was purified by column chromatography (silica gel; mobile phase chloroform:acetone, 95:5. Beige crystals. Yield: 0.51 g, 49%. M. p.: 130-134° C. (crystallized from 2-propanol). HPLC $R_t$=15.3 min (60% $CH_3OH$+40% buffer), MS ESI+(CV 10) m/z (rel. %): 338 $[M+H]^+$ (100), 340 $[M+H]^+$ (33); (CV 20) m/z (rel. %): 254 $[C_{10}H_{12}ClN_5O+H]^+$ (100), 256 $[C_{10}H_{12}ClN_5O+H]^+$ (45), 338 $[M+H]^+$ (86), 340 $[M+H]^+$ (44). $^1$H NMR (300 MHz, DMSO-$d_6$): δ 1.55 (1H, m, THP, H5'), 1.60 (1H, m, THP, H5'), 1.66 (3H, s, —$CH_3$), 1.70 (1H, m, THP, H4'), 1.84 (1H, dd, J=12.8, 2.2 Hz, THP H3'), 1.98 (1H, d, J=12.3 Hz THP H4'), 2.89 (1H, qq, J=12.1, 3.6 Hz, THP H3'), 3.63 (1H, tt, J=11.3, 3.6 Hz THP H6'), 3.78 (2H, d, J=5.7 Hz, —$CH_2$—OH), 4.03 (1H, d, J=11.3 Hz THP H6'), 4.10 (2H, bs, —NH—$CH_2$—), 4.72 (1H, t, J=5.7 Hz, OH), 5.50 (1H, tt, J=6.7, 1.7 Hz, —$CH_2$—CH=), 5.63 (1H, dd, J=11.3, 2.2 Hz, THP H2'), 8.04 (1H, bs, $N^6$H), 8.23 (1H, s, H2). $^{13}$C NMR (300 MHz, DMSO-$d_6$): δ 13.56 (—$CH_3$), 22.52 (THP C4'), 24.39 (THP C5'), 28.04 (—$CH_2$—OH), 28.04 (THP C3'), 37.25 (—NH—$CH_2$—), 65.75 (—$CH_2$—OH), 68.03 (THP C6'), 82.99 (THP C2'), 117.80 (C5), 120.32 (—CH=), 135.79 (C8), 137.39 (=C<), 149.49 (C4), 152.78 (C2), 153.12 (C6).

(E)-8-Bromo-6-(4-hydroxy-3-methylbut-2-en-1-ylamino)-9-(tetrahydropyran-2-yl)-9H-purine (E)-6-(4-hydroxy-3-methylbut-2-en-1-ylamino)-9-(tetrahydropyran-2-yl)-9H-purine (Ex 2.3) (2.44 g, 8.0 mmol) was dissolved under argon in dry tetrahydrofuran (55 ml). The solution was treated dropwise over 1 h with commercially available 1.8 M lithium diisopropylamide solution (45 ml, 90 mmol). The reaction mixture was stirred at −78° C. for 1.0 h. After this time, solution of tetrabromomethane (8.01 g, 24.2 mmol) in dry tetrahydrofuran (20 ml) was added dropwise over 35 min to the reaction mixture, which was then stirred for 1 h. Then, 20% $NH_4Cl$ (70 ml) was added dropwise. After spontaneous warming to room temperature, the layers were separated. The aqueous layer was extracted with diethyl ether (1×70 ml). Collected organic layers were washed with brine (2×50 ml), dried with $Na_2SO_4$, and evaporated. The crude product was purified by column chromatography (silica gel; mobile phase chloroform:ethyl acetate 1:3, on TLC chromatogram $R_f$=0.11. Light beige crystals. Yield: 1.19 g, 45%. M. p.: 138-142° C. (crystallized from ethyl acetate). HPLC $R_t$=15.5 min (60% $CH_3OH$+40% buffer). UV (60% $CH_3OH$+40% buffer) $\lambda_{max}$ 274 nm, $\lambda_{min}$ 235 nm. MS ESI+(CV 18) m/z (rel. %): 382 $[M+H]^+$ (100), 384 $[M+H]^+$ (92); 406 $[M+Na]^+$ (60), 404 $[M+Na]^+$ (57); (CV 37) m/z (rel. %): 406 $[M+Na]^+$ (100), 404 $[M+Na]^+$ (96), 332 $[C_{10}H_{12}BrN_5O+Na]^+$ (88), 320 $[C_{10}H_{12}BrN_5O+Na]^+$ (85), 300 $[C_{10}H_{12}BrN_5O+H]^+$ (84), 298 $[C_{10}H_{12}BrN_5O+H]^+$ (82), 382 $[M+H]^+$ (36), 384 $[M+H]^+$ (35). $^1$H NMR (300 MHz, DMSO-$d_6$): δ 1.55 (1H, m, THP, H5'), 1.60 (1H, m, THP, H5'), 1.66 (3H, s, —$CH_3$), 1.70 (1H, m, THP, H4'), 1.84 (1H, dd, J=12.8, 2.2 Hz, THP H3'), 1.98 (1H, d, J=12.3 Hz THP H4'), 2.89 (1H, qq, J=12.1, 3.6 Hz, THP H3'), 3.63 (1H, tt, J=11.3, 3.6 Hz THP H6'), 3.78 (2H, d, J=5.7 Hz, —$CH_2$—OH), 4.03 (1H, d, J=11.3 Hz THP H6'), 4.10 (2H, bs, —NH—$CH_2$—), 4.72 (1H, t, J=5.7 Hz, OH), 5.50 (1H, tt, J=6.7, 1.7 Hz, —$CH_2$—CH=), 5.63 (1H, dd, J=11.3, 2.2 Hz, THP H2'), 8.04 (1H, bs, $N^6$H), 8.23 (1H, s, H2). $^{13}$C NMR (300 MHz, DMSO-$d_6$): δ 13.56 (—$CH_3$), 22.52 (THP C4'), 24.39 (THP C5'), 28.04 (—$CH_2$—OH), 28.04 (THP C3'), 37.25 (—NH—$CH_2$—), 65.75 (—$CH_2$—OH), 68.03 (THP C6'), 82.99 (THP C2'), 117.80 (C5), 120.32 (—CH=), 135.79 (C8), 137.39 (=C<), 149.49 (C4), 152.78 (C2), 153.12 (C6).

8-Bromo-6-benzylamino-9-(tetrahydropyran-2-yl)-9H-purine

The compound was prepared from 6-benzylamino-9-(tetrahydropyran-2-yl)-9H-purine (Ex 2.5) applying the procedure described in literature (Nolsøe et al., *Synth. Commun.* 1998, 28, 4303; Gunji, *Helv. Chim. Acta* 2000, 83, 1331). 2.14 g (6.9 mmol) of (2.1) was under argon dissolved in 25 ml dry tetrahydrofuran and cooled to −78° C. The solution was treated dropwise over 30 min with 21 ml (42 mmol) of lithium diisopropylamide solution. The reaction mixture was then stirred at −78° C. for 1 h. After this time, a solution of 4.58 g (13.8 mmol) tetrabromomethane in 10 ml of dry tetrahydrofuran was added dropwise over 20 min, and the mixture further stirred for 1 h. Without loading the bottle with argon, 44 ml of 20% NH$_4$Cl solution was added dropwise. The cooling bath was removed and the mixture left to get room temperature. The layers were separated. The organic layer was washed with 15 ml of water (3×30 ml), dried with Na$_2$SO$_4$, and evaporated. The crude product was purified by column chromatography (mobile phase hexanes:ethyl acetate 3:2, on TLC chromatogram R$_f$=0.17). After column chromatography, the collected fractions were partly concentrated in vacuo let to crystallize in refrigerator over night. Light beige crystals were filtered off, washed with hexanes and dried. Yield: 2.05 g, 76%. M. p.: 120-124° C. HPLC R$_t$=16.6 min (75% CH$_3$OH+25% buffer). UV (75% CH$_3$OH+25% buffer) $\lambda_{max}$ 274 nm, $\lambda_{min}$ 235 nm. MS ESI+ (CV 10) m/z (rel. %): 390 [M+H]$^+$ (100), 388 [M+H]$^+$ (84). $^1$H NMR (300 MHz, DMSO-d$_6$): δ 1.55 (1H, m, THP H5'), 1.66 (3H, mm, THP H4', 5'), 1.84 (1H, d, J=12.8, THP H3'), 1.98 (1H, d, J=8.8, THP H4'), 3.00 (1H, qq, J=12.6, 4.9, THP H3'), 3.69 (1H, m, THP H6'), 4.03 (1H, d, J=11.8, THP H6'), 4.67 (2H, bs, NH—CH$_2$-Ph), 5.61 (1H, d, J=9.8, THP H2'), 7.21 (1H, m, Ph H3'), 7.29 (4H, m, Ph), 8.20 (1H, s, H2), 8.59 (1H, bs, N$^6$H).

8-Iodo-6-benzylamino-9-(tetrahydropyran-2-yl)-9H-purine

The compound was prepared from 6-benzylamino-9-(tetrahydropyran-2-yl)-9H-purine (Ex 2.5) applying the procedure described in literature (Nolsøe et al., *Synth. Commun.* 1998, 28, 4303; Gunji, *Helv. Chim. Acta* 2000, 83, 1331). 6-Benzylamino-9-(tetrahydropyran-2-yl)-9H-purine (0.30 g; 0.97 mmol) was under argon dissolved in dry tetrahydrofuran (3 ml) and cooled to −78° C. The solution was treated dropwise with 1.5 ml (42 mmol) of lithium diisopropylamide solution. The reaction mixture was then stirred at −78° C. for 70 min. After this time, a solution of 0.98 g (3.9 mmol) iodine in 1.5 ml of dry tetrahydrofuran was added dropwise, and the mixture further stirred for 1 h. The reaction was quenched, without loading the bottle with argon, with 10 ml of solution of Na$_2$S$_2$O$_3$.5H$_2$O (1.4 g, 5.7 mmol) added dropwise. The cooling bath was removed and the mixture left to get room temperature. The layers were separated. The organic layer was diluted with 6 ml of diethyl ether and washed twice with 5 ml of water. Combined organic layers were dried with Na$_2$SO$_4$, and evaporated. The crude product was purified by column chromatography (mobile phase hexanes:ethyl acetate 3:2, on TLC chromatogram R$_f$=0.18). After column chromatography, the collected fractions were concentrated in vacuo and residue crystallized from ethyl ether to give white crystals. Yield: 134 mg, 32%. M. p.: 153-155° C. HPLC R$_t$=15.7 min (75% CH$_3$OH+ 25% buffer). UV (75% CH$_3$OH+25% buffer) $\lambda_{max}$ 278 nm, $\lambda_{min}$ 239 nm. MS ESI+(CV 13) m/z (rel. %): 436 [M+H]$^+$ (100); (CV 30) m/z (rel. %): 352 [C$_{12}$H$_{10}$N$_5$I+H]$^+$ (100). 436 [M+H]$^+$ (55). $^1$H NMR (300 MHz, DMSO-d$_6$): δ 1.57 (2H, m, THP H5'), 1.64 (1H, qq, J=12.4, 3.4, THP H4'), 1.81 (1H, d, J=12.4, THP H3'), 1.99 (1H, d, J=12.4, THP H4'), 3.09 (1H, qq, J=12.4, 3.4, THP H3'), 3.64 (1H, tt, J=11.1, 3.4, THP H6'), 4.05 (1H, d, J=11.1, THP H6'), 4.67 (2H, bs, NH—CH$_2$-Ph), 5.54 (1H, dd, J=11.1, 2.3, THP H2'), 7.20 (1H, tt, J=6.8, 2.3, Ph H4'), 7.28 (2H, tt, J=6.8, 2.3, Ph H3', H5'), 7.29 (2H, dd, J=6.8, 2.3, Ph H2', H6'), 8.13 (1H, s, H2), 8.50 (1H, bs, N$^6$H). $^{13}$C-NMR (300 MHz, DMSO-d$_6$): δ 22.67 (THP C4'), 24.39 (THP C5'), 28.06 (THP C3'), 42.87 (NH—CH$_2$-Ph), 68.00 (THP C6'), 85.76 (THP C2'), 101.56 (C8), 122.00 (C5), 126.52 (Ph C4'), 128.03 (Ph C2', C6'), 128.10 (Ph C3', C5'), 490.98 (C4), 152.01 (C2), 152.98 (C6).

TABLE 1

Compounds of this invention prepared according to Example 3 (R6—substituent in purine position 6, R8—substituent in purine position 8, R9 = Cyc—substituent in purine position 9)

| No. | R6 | R8 | R9 | % C | % H | % N | ESI-MS [M$^+$H$^+$] |
|---|---|---|---|---|---|---|---|
| 1 | furfurylamino | Cl | 2-tetrahydropyranyl | 54.0/53.9 | 4.8/4.7 | 21.0/21.5 | 334.8 |
| 2 | benzylamino | Cl | 2-tetrahydropyranyl | 59.4/59.5 | 5.3/5.2 | 20.4/20.8 | 344.8 |
| 3 | (3-methylbut-2-en-1-yl)amino | Cl | 2-tetrahydropyranyl | 56.0/56.1 | 6.3/6.5 | 21.8/21.5 | 322.8 |
| 4 | (Z)-(4-hydroxy-3-methylbut-2-en-1-yl)amino | Cl | 2-tetrahydropyranyl | 53.3/52.9 | 6.0/6.2 | 20.7/21.0 | 338.8 |
| 5 | (E)-(4-hydroxy-3-methylbut-2-en-1-yl)amino | Cl | 2-tetrahydropyranyl | 53.3/52.7 | 6.0/6.3 | 20.7/21.1 | 338.8 |
| 6 | allylamino | Cl | 2-tetrahydropyranyl | 53.2/53.8 | 5.5/5.4 | 23.8/23.6 | 294.8 |
| 7 | 3-fluorobenzylamino | Cl | 2-tetrahydropyranyl | 56.4/56.0 | 4.7/4.9 | 19.3/19.7 | 362.8 |
| 8 | 3-methoxylbenzylamino | Cl | 2-tetrahydropyranyl | 57.8/58.0 | 5.4/5.3 | 18.7/18.5 | 374.9 |
| 9 | 3-hydroxylbenzylamino | Cl | 2-tetrahydropyranyl | 56.8/57.5 | 5.0/5.2 | 19.5/19.1 | 360.8 |
| 10 | 3.4-dihydroxybenzylamino | Cl | 2-tetrahydropyranyl | 54.3/54.5 | 4.8/4.9 | 18.6/18.4 | 376.9 |
| 11 | 3.4-difluorobenzylamino | Cl | 2-tetrahydropyranyl | 53.8/54.0 | 4.3/4.3 | 18.4/18.2 | 380.8 |
| 12 | 3.4-dimethoxybenzylamino | Cl | 2-tetrahydropyranyl | 56.5/56.8 | 5.5/5.4 | 17.3/17.0 | 404.9 |
| 13 | 4-hydroxybenzylamino | Cl | 2-tetrahydropyranyl | 56.8/56.9 | 5.0/5.0 | 19.5/19.6 | 360.8 |
| 14 | 4-hydroxy-3,5-dimethoxybenzylamino | Cl | 2-tetrahydropyranyl | 54.4/54.6 | 5.3/5.2 | 16.7/16.9 | 420.9 |
| 15 | anilino | Cl | 2-tetrahydropyranyl | 58.3/58.1 | 4.9/5.1 | 21.2/21.3 | 330.8 |
| 16 | 4-hydroxyanilino | Cl | 2-tetrahydropyranyl | 55.6/55.3 | 4.7/4.9 | 20.3/20.3 | 346.8 |
| 17 | 3-methoxyanilino | Cl | 2-tetrahydropyranyl | 56.8/56.7 | 5.0/5.1 | 19.5/19.4 | 360.8 |
| 18 | 3-fluoroanilino | Cl | 2-tetrahydropyranyl | 55.3/55.5 | 4.4/4.5 | 20.1/19.9 | 348.8 |
| 19 | 3-chloroanilino | Cl | 2-tetrahydropyranyl | 52.8/53.0 | 4.2/4.2 | 19.2/19.0 | 365.2 |
| 20 | 3-methylanilino | Cl | 2-tetrahydropyranyl | 59.4/59.3 | 5.3/5.4 | 20.4/20.5 | 344.8 |
| 21 | furfurylamino | Br | 2-tetrahydropyranyl | 47.6/47.4 | 4.3/4.4 | 18.5/18.4 | 379.2 |
| 22 | benzylamino | Br | 2-tetrahydropyranyl | 52.6/52.8 | 4.7/4.5 | 18.0/18.1 | 389.3 |
| 23 | (3-methylbut-2-en-1-yl)amino | Br | 2-tetrahydropyranyl | 49.2/49.4 | 5.5/5.4 | 19.1/19.2 | 367.2 |
| 24 | (E)-(4-hydroxy-3-methylbut-2-en-1-yl)amino | Br | 2-tetrahydropyranyl | 47.1/47.2 | 5.3/5.2 | 18.3/18.1 | 383.3 |
| 25 | (Z)-(4-hydroxy-3-methylbut-2-en-1-yl)amino | Br | 2-tetrahydropyranyl | 47.1/47.0 | 5.3/5.3 | 18.3/18.3 | 383.3 |
| 26 | 3-fluorobenzylamino | Br | 2-tetrahydropyranyl | 50.3/50.6 | 4.2/4.1 | 17.2/17.5 | 407.2 |
| 27 | 3,4-difluorobenzylamino | Br | 2-tetrahydropyranyl | 48.1/47.8 | 3.8/3.7 | 16.5/16.3 | 425.3 |
| 28 | 3-methoxybenzylamino | Br | 2-tetrahydropyranyl | 51.7/51.8 | 4.8/5.0 | 16.7/16.8 | 419.3 |
| 29 | 3-hydroxylbenzylamino | Br | 2-tetrahydropyranyl | 50.5/50.2 | 4.5/4.5 | 17.3/17.1 | 405.3 |
| 30 | 3-chlorobenzylamino | Br | 2-tetrahydropyranyl | 48.3/48.5 | 4.1/4.0 | 16.6/16.8 | 423.7 |

TABLE 1-continued

Compounds of this invention prepared according to Example 3 (R6—substituent in purine position 6, R8—substituent in purine position 8, R9 = Cyc—substituent in purine position 9)

| No. | R6 | R8 | R9 | % C | % H | % N | ESI-MS [M+H+] |
|---|---|---|---|---|---|---|---|
| | | | | \multicolumn{3}{c}{CHN analyses calculated/found} | |
| 31 | 4-chlorobenzylamino | Br | 2-tetrahydropyranyl | 48.3/48.5 | 4.1/3.9 | 16.6/16.9 | 423.7 |
| 32 | 2-bromobenzylamino | Br | 2-tetrahydropyranyl | 43.7/43.4 | 3.7/3.9 | 15.0/14.9 | 468.2 |
| 33 | 3-jodobenzylamino | Br | 2-tetrahydropyranyl | 39.7/40.0 | 3.3/3.3 | 13.6/13.7 | 515.2 |
| 34 | 3-methylbenzylamino | Br | 2-tetrahydropyranyl | 53.7/53.6 | 5.0/5.1 | 17.4/17.6 | 403.3 |
| 35 | 2-methoxybenzylamino | Br | 2-tetrahydropyranyl | 51.7/51.7 | 4.8/5.0 | 16.7/16.8 | 419.3 |
| 36 | 4-methoxylbenzylamino | Br | 2-tetrahydropyranyl | 51.7/51.6 | 4.8/4.9 | 16.7/16.7 | 419.3 |
| 37 | 4-hydroxybenzylamino | Br | 2-tetrahydropyranyl | 50.5/50.3 | 4.5/4.6 | 17.3/17.2 | 405.3 |
| 38 | 3.4-dichlorobenzylamino | Br | 2-tetrahydropyranyl | 44.7/44.5 | 3.5/3.2 | 15.3/15.6 | 458.2 |
| 39 | 3.4-dihydroxybenzylamino | Br | 2-tetrahydropyranyl | 48.6/48.4 | 4.3/4.1 | 16.7/17.1 | 421.3 |
| 40 | 2-hydroxy-3-methoxybenzylamino | Br | 2-tetrahydropyranyl | 49.8/50.1 | 4.6/4.5 | 16.1/16.0 | 435.3 |
| 41 | 3.4-dimethoxybenzylamino | Br | 2-tetrahydropyranyl | 50.9/50.8 | 5.0/5.2 | 15.6/15.4 | 449.3 |
| 42 | anilino | Br | 2-tetrahydropyranyl | 51.4/51.4 | 4.3/4.2 | 18.7/18.5 | 375.2 |
| 43 | 3-methoxyanilino | Br | 2-tetrahydropyranyl | 50.5/50.5 | 4.5/4.5 | 17.3/17.5 | 405.3 |
| 44 | 4-hydroxyanilino | Br | 2-tetrahydropyranyl | 49.3/49.5 | 4.1/4.1 | 18.0/18.0 | 391.2 |
| 45 | furfurylamino | I | 2-tetrahydropyranyl | 42.4/42.3 | 3.8/3.6 | 16.5/16.2 | 426.2 |
| 46 | benzylamino | I | 2-tetrahydropyranyl | 46.9/46.9 | 4.2/4.1 | 16.1/15.7 | 436.3 |
| 47 | (3-methylbut-2-en-1-yl)amino | I | 2-tetrahydropyranyl | 43.6/43.5 | 4.9/4.9 | 17.0/17.4 | 414.3 |
| 48 | (E)-(4-hydroxy-3-methylbut-2-en-1-yl)amino | I | 2-tetrahydropyranyl | 42.0/42.1 | 4.7/4.6 | 16.3/16.2 | 430.3 |
| 49 | (Z)-(4-hydroxy-3-methylbut-2-en-1-yl)amino | I | 2-tetrahydropyranyl | 42.0/42.1 | 4.7/4.8 | 16.3/16.5 | 430.3 |
| 50 | 3-fluorobenzylamino | I | 2-tetrahydropyranyl | 45.1/45.3 | 3.8/3.5 | 15.5/15.7 | 454.3 |
| 51 | 3-chlorobenzylamino | I | 2-tetrahydropyranyl | 43.5/43.8 | 3.7/3.8 | 14.9/15.1 | 470.7 |
| 52 | 3-methoxylbenzylamino | I | 2-tetrahydropyranyl | 46.5/46.4 | 4.3/4.5 | 15.1/15.0 | 466.3 |
| 53 | 3-hydroxybenzylamino | I | 2-tetrahydropyranyl | 45.3/45.1 | 4.0/4.1 | 15.5/15.3 | 452.3 |
| 54 | 3.4-dihydroxybenzylamino | I | 2-tetrahydropyranyl | 43.7/43.8 | 3.9/3.7 | 15.0/14.8 | 468.3 |
| 55 | 3.4-difluorobenzylamino | I | 2-tetrahydropyranyl | 43.3/43.6 | 3.4/3.5 | 14.9/14.7 | 472.3 |
| 56 | 3.4-dimethoxybenzylamino | I | 2-tetrahydropyranyl | 46.1/46.4 | 4.5/4.7 | 14.1/14.3 | 496.3 |
| 57 | 4-hydroxybenzylamino | I | 2-tetrahydropyranyl | 45.3/45.2 | 4.0/4.1 | 15.5/15.6 | 452.3 |
| 58 | 2-hydroxy-3-methoxybenzylamino | I | 2-tetrahydropyranyl | 44.9/45.0 | 4.2/4.0 | 14.6/14.2 | 482.3 |
| 59 | anilino | I | 2-tetrahydropyranyl | 45.6/45.8 | 3.8/3.9 | 16.6/16.3 | 422.2 |
| 60 | 4-hydroxyanilino | I | 2-tetrahydropyranyl | 44.0/44.3 | 3.7/3.8 | 16.0/16.2 | 438.2 |
| 61 | 3-methoxyanilino | I | 2-tetrahydropyranyl | 45.3/45.1 | 4.0/3.9 | 15.5/15.8 | 452.3 |
| 62 | 3-methylanilino | I | 2-tetrahydropyranyl | 46.9/46.8 | 4.2/4.0 | 16.1/16.0 | 436.3 |
| 63 | furfurylamino | Cl | 2-tetrahydrofuranyl | 52.6/52.9 | 4.4/4.6 | 21.9/22.1 | 320.8 |
| 64 | (E)-(4-hydroxy-3-methylbut-2-en-1-yl)amino | Cl | 2-tetrahydrofuranyl | 51.9/52.2 | 5.6/5.4 | 21.6/21.5 | 324.8 |
| 65 | (3-methylbut-2-en-1-yl)amino | Cl | 2-tetrahydrofuranyl | 54.6/54.8 | 5.9/5.7 | 22.8/22.9 | 308.8 |
| 66 | 3.4-dihydroxybenzylamino | Cl | 2-tetrahydrofuranyl | 53.1/53.5 | 4.5/4.6 | 19.4/19.2 | 362.8 |
| 67 | 3.4-difluorobenzylamino | Cl | 2-tetrahydrofuranyl | 52.5/52.8 | 3.9/3.8 | 19.2/19.0 | 366.8 |
| 68 | 3.4-dimethoxybenzylamino | Cl | 2-tetrahydrofuranyl | 55.5/55.2 | 5.2/5.3 | 18.0/17.6 | 340.8 |
| 69 | 3-methoxylbenzylamino | Cl | 2-tetrahydrofuranyl | 56.8/56.7 | 5.0/5.1 | 19.5/19.7 | 360.8 |
| 70 | 3-hydroxybenzylamino | Cl | 2-tetrahydrofuranyl | 55.6/55.4 | 4.7/4.8 | 20.3/20.1 | 346.8 |
| 71 | 3-fluorobenzylamino | Cl | 2-tetrahydrofuranyl | 55.3/55.6 | 4.4/4.4 | 20.1/19.8 | 348.8 |
| 72 | furfurylamino | Br | 2-tetrahydrofuranyl | 46.2/46.0 | 3.9/4.0 | 19.2/18.9 | 365.2 |
| 73 | benzylamino | Br | 2-tetrahydrofuranyl | 51.4/51.3 | 4.3/4.1 | 18.7/18.5 | 375.2 |
| 74 | (Z)-(4-hydroxy-3-methylbut-2-en-1-yl)amino | Br | 2-tetrahydrofuranyl | 45.7/45.7 | 4.9/4.5 | 19.0/19.2 | 369.2 |
| 75 | (3-methylbut-2-en-1-yl)amino | Br | 2-tetrahydrofuranyl | 47.7/47.9 | 5.2/5.2 | 19.9/19.8 | 353.2 |
| 76 | 3-methoxylbenzylamino | I | 2-tetrahydrofuranyl | 44.0/44.1 | 3.7/3.8 | 16.0/16.1 | 438.2 |
| 77 | 4-hydroxybenzylamino | I | 2-tetrahydrofuranyl | 44.0/43.8 | 3.7/3.9 | 16.0/16.0 | 438.2 |
| 78 | anilino | I | 2-tetrahydrofuranyl | 44.2/44.1 | 3.5/3.6 | 17.2/17.5 | 408.2 |
| 79 | 3-hydroxyanilino | I | 2-tetrahydrofuranyl | 42.6/42.5 | 3.3/3.1 | 16.6/17.0 | 424.2 |

Example 4

Syntheses of 6-alkylamino-8-substituted-9-(tetrahydropyran-2-yl)-9H-purines

6-Furfurylamino-8-dimethylamino-9-(tetrahydropyran-2-yl)-9H-purine

8-Chloro-6-furfurylamino-9-(tetrahydropyran-2-yl)-9H-purine (Ex 3.1) (229 mg, 0.69 mmol) was dissolved in 50% solution of dimethylamine in methanol (3 ml). The solution was stirred at room temperature over night and evaporated. The residue was dissolved in chloroform (6 ml), extracted with water (2×7.5 ml), dried with $Na_2SO_4$, and evaporated. After crystallization from ethyl acetate (6 ml) were obtained yellowish crystals. Yield: 195 mg (83%). M. p.: 174-176° C. TLC $R_f$=0.29 (chloroform:acetone 4:1). MS ESI+(CV 10) m/z (rel. %): 343 [M+H]+ (100); (CV 24) m/z (rel. %): 259 $[C_{12}H_{14}N_6O+H]^+$ (100). 343 [M+H]+ (89). $^1$H (500 MHz, DMSO-$d_6$): δ 1.47-1.61 (4H, m), 1.89-1.94 (1H, m), 2.85 (6H, s), 2.99-3.08 (1H, m), 3.58 (1H, dt, J=11.3 Hz, J=2.45 Hz), 3.99 (1H, bd, J=11.31 Hz), 4.63 (2H, bs), 5.29 (1H, dd, J=11.30 Hz, J=2.14 Hz), 6.16 (1H, dd, J=3.06 Hz, J=0.61 Hz), 6.30 (1H, dd, J=3.06 Hz, J=1.83 Hz), 7.47 (1H, dd, J=1.83 Hz, J=0.61 Hz), 7.56 (1H, t, J=6.11 Hz), 8.06 (1H, s). $^{13}$C (125 MHz, DMSO-$d_6$): 23.5, 25.0, 28.0, 37.2, 42.8, 68.4, 83.3, 107.0, 110.9, 117.4, 142.2, 150.5, 150.8, 152.7, 153.9, 155.9.

8-(2-Aminoethylamino)-6-furfurylamino-9-(tetrahydropyran-2-yl)-9H-purine 0.40 g (1.05 mmol) 8-Bromo-6-furfurylamino-9-(tetrahydropyran-2-yl)-9H-purine (3.2) was dissolved in 1,2-diaminoethane (3.0 ml) and heated at 50° C. for 35 min, then left over night at room temperature. The reaction mixture was evaporated and the residue purified by column chromatography (silica gel; gradient elution, starting with mobile phase chloroform:methanol:NH$_4$OH 95:5:0.5, ending with mobile phase chloroform:methanol:NH$_4$OH 9:1:0.1). After column chromatography, the collected fractions were concentrated in vacuo and dried in dessiccator with P$_2$O$_5$. Yellowish viscous substance. Yield: 0.36 g, 77%. MS ESI+ (CV 20) m/z (rel. %): 358 [M+H]$^+$ (100), (CV 45) m/z (rel. %): 274 [C$_{12}$H$_{15}$N$_7$O+H]$^+$ (100), 358 [M+H]$^+$ (37). $^1$H NMR (300 MHz, CDCl$_3$): δ 1.65-1.83 (4H, m, THP), 1.94-2.15 (2H, m, THP), 2.99 (1H, q, J=6.2 Hz, THP), 3.43-3.60 (3H, m, —NH—CH$_2$—CH$_2$—), 3.77-3.68 (1H, m, —NH—CH$_2$—CH$_2$—), 4.20 (1H, d, J=11.2 Hz, THP), 4.75-4.88 (3H, m, THP, —NH—CH$_2$-Fur, 5.72 (1H, d, J=9.7 Hz, THP), 5.83 (1H, m, Fur), 6.29 (2H, d, J=9.7 Hz, Fur), 7.38 (1H, s, —NH—CH$_2$-Fur, 8.19 (1H, s, H2). $^{13}$C NMR (300 MHz, CDCl$_2$): δ 22.04, 24.63, 29.22, 37.26, 40.70, 44.76, 68.82, 82.04, 106.68, 109.86, 116.89, 141.51, 148.11, 149.15, 150.65, 151.32, 152.04.

6-Furfurylamino-8-(2-hydroxyethylamino)-9-(tetrahydropyran-2-yl)-9H-purine 0.30 g (0.9 mmol) 8-Chloro-6-furfurylamino-9-(tetrahydropyran-2-yl)-9H-purine (3.1) was dissolved in ethanolamine (2.0 ml) and heated at 80° C. for 75 min. The reaction mixture was evaporated and the residue purified by column chromatography (silica gel; mobile phase chloroform:methanol:NH$_4$OH 95:5:0.5). The product was dried in dessiccator with P$_2$O$_5$. Yellowish foam. Yield: 0.18 g, 56%. HPLC R$_f$=12.5 min (60% CH$_3$OH+40% buffer). UV (60% CH$_3$OH+40% buffer) λ$_{max}$ 283 nm, λ$_{min}$ 243 nm. MS ESI+ (CV 10) m/z (rel. %): 359 [M+H]$^+$ (100), 275 [C$_{12}$H$_{14}$N$_6$O$_2$+H]$^+$ (8); (CV 40) m/z (rel. %): 275 [C$_{12}$H$_{14}$N$_6$O$_2$+H]$^+$ (100). 359 [M+H]$^+$ (19). $^1$H (500 MHz, DMSO-d$_6$): δ 1.47-1.51 (1H, m), 1.54-1.63 (3H, m), 1.86-1.94 (1H, m), 2.47-2.54 (1H, m), 3.37-3.41 (2H, m), 3.56-3.57 (2H, bs), 3.60-3.65 (1H, m), 3.96-3.99 (1H, bd, J=10.39 Hz), 4.61-4.62 (2H, d), 4.75 (1H, bs), 5.49 (1H, dd, J=10.80 Hz, J=2.32 Hz), 6.14-6.15 (1H, bd, J=3.06 Hz), 6.28-6.32 (2H, m), 7.15-7.18 (1H, t), 7.46-7.47 (1H, m), 7.94 (1H, s). $^{13}$C (125 MHz, DMSO-d$_6$): δ 23.1, 24.9, 28.9, 37.3, 45.3, 60.2, 68.5, 81.7, 106.8, 110.9, 117.6, 142.0, 149.1, 149.5, 151.3, 151.8, 154.2.

6-Furfurylamino-8-(3-hydroxypropylamino)-9-(tetrahydropyran-2-yl)-9H-purine 0.28 g (0.8 mmol) 8-Chloro-6-furfurylamino-9-(tetrahydropyran-2-yl)-9H-purine (3.1) was dissolved in 3-amino-1-propanol (2.0 ml) and heated at 60° C. for 6 h. The reaction mixture was evaporated and the residue purified by column chromatography (silica gel; mobile phase chloroform:acetone 85:15, on TLC chromatogram R$_f$=0.14). The product was dried in dessiccator with P$_2$O$_5$. Yellowish foam. Yield: 0.28 g, 90%. HPLC R$_f$=11.6 min (65% CH$_3$OH+35% buffer). UV (65% CH$_3$OH+35% buffer) λ$_{max}$ 283 nm, λ$_{min}$ 244 nm. MS ESI+(CV 20) m/z (rel. %): 373 [M+H]$^+$ (100), 289 [C$_{13}$H$_{16}$N$_6$O$_2$+H]$^+$ (14). (CV 30) m/z (rel. %): 289 [C$_{13}$H$_{16}$N$_6$O$_2$+H]$^+$ (100), 373 [M+H]$^+$ (82). $^1$H NMR (300 MHz, CDCl$_3$): δ 1.51 (1H, m, THP H5'), 1.64 (3H, mm, THP H3', 4', 5'), 1.77 (2H, dui, J=6.2, —NH—CH$_2$—CH$_2$—), 1.93 (1H, m, THP H4'), 2.56 (1H, qq, J=11.8, 4.2, THP H3'), 3.45 (2H, J=t, 6.0, —NH—CH$_2$—CH$_2$—CH$_2$—), 3.53 (2H, t, J=5.9, —NH—CH$_2$—CH$_2$—CH$_2$—OH), 3.65 (1H, tt, J=11.3, 3.3, THP H5'), 4.01 (1H, d, J=11.3, THP H6'), 4.67 (2H, d, 6.2, —NH—CH$_2$-Fur, 4.68 (1H, bs, —OH), 5.52 (1H, dd, J=11.2, 2.0, THP H2'), 6.19 (1H, d, J=3.2, Fur H3'), 6.34 (1H, m, Fur H4'), 6.50 (1H, t, J=5.5, HN8), 7.24 (1H, t, J=6.2, HN6), 7.51 (1H, m, Fur H5'), 7.99 (1H, s, H2). $^{13}$C-NMR (300 MHz, DMSO-d$_6$): δ 22.57 (THP C4'), 24.31 (THP C5'), 28.32 (THP C3'), 36.81 (NH—CH$_2$-Fur, 31.93 (—NH—CH$_2$—CH$_2$—CH$_2$—), 39.98 (—NH—CH$_2$—CH$_2$—CH$_2$—), 58.94 (—CH$_2$—CH$_2$—CH$_2$—NH$_2$), 67.94 (THP C6'), 81.12 (THP C2'), 106.34 (Fur C3'), 110.35 (Fur C4'), 117.12 (C5), 141.54 (Fur C5'), 148.48 (C2), 148.99 (C4), 150.70 (C6), 151.23 (C8), 153.70 (Fur C2').

8-Allylamino-6-furfurylamino-9-(tetrahydropyran-2-yl)-9H-purine 0.21 g (0.64 mmol) 8-Chloro-6-furfurylamino-9-(tetrahydropyran-2-yl)-9H-purine (3.1) was dissolved in allylamine (2.0 ml) and heated at 60° C. for 10 h. The reaction mixture was evaporated. The residue was then evaporated 3 times with methanol (3 ml) and 3 times with chloroform (3 ml). The product was purified by column chromatography (silica gel; mobile phase chloroform:acetone 9:1). The product was dried in dessiccator with P$_2$O$_5$. Rust-coloured viscous liquid. Yield: 0.13 g, 58%. HPLC (flow rate 0.6 ml/min) R$_f$=23.5 min (60% CH$_3$OH+40% buffer). MS ESI+(CV 10) m/z (rel. %): 355 [M+H]$^+$ (100), 709 [2M+H]$^+$ (21), (CV 20) m/z (rel. %): 355 [M+H]$^+$ (100), 271 [C$_{13}$H$_{14}$N$_6$O+H]$^+$ (24), $^1$H NMR (300 MHz, CDCl$_3$): δ 1.51 (1H, m, THP H5'), 1.65 (3H, mm, THP H3', 4', 5'), 1.94 (1H, d, J=11.8, THP H4'), 2.63 (1H, qq, J=11.8, 4.2, THP H3'), 3.69 (1H, m, THP H6'), 4.01 (1H, m, THP H6'), 4.02 (2H, t, J=5.5, —CH$_2$—CH=CH$_2$), 4.67 (2H, d, J=6.2, —NH—CH$_2$-Fur, 5.09 (1H, dd, J=10.3, 1.5, —CH$_2$—CH=CH$_2$), 5.21 (1H, dd, J=17.2, 1.8, —CH$_2$—CH=CH$_2$), 5.53 (1H, dd, J=11.2, 2.0, THP H2'), 5.99 (1H, m, —CH$_2$—CH=CH$_2$), 6.19 (1H, d, J=3.2, Fur H3'), 6.34 (1H, m, Fur H4'), 6.59 (1H, t, J=5.9, HN8), 7.20 (1H, t, J=6.2, HN6), 7.51 (1H, m, Fur H5'), 7.99 (1H, s, H2). $^{13}$C-NMR (300 MHz, DMSO-d$_6$): δ 22.57 (THP C4'), 24.28 (THP C5'), 28.29 (THP C3'), 36.76 (NH—CH$_2$-Fur, 44.35 (—CH$_2$—CH=CH$_2$), 67.89 (THP C6'), 81.17 (THP C2'), 106.30 (Fur C3'), 110.27 (Fur C4'), 115, 01 (—CH$_2$—CH=CH$_2$), 117.09 (C5), 135.78 (—CH$_2$—CH=CH$_2$), 141.46 (Fur C5'), 148.51 (C2), 149.15 (C8), 150.77 (C6), 150.87 (C4), 153.64 (Fur C2').

6-Furfurylamino-8-methoxy-9-(tetrahydropyran-2-yl)-9H-purine

Potassium tert-butoxide (107 mg, 0.53 mmol) was added to a solution of 8-chloro-6-furfurylamino-9-(tetrahydropyran-2-yl)-9H-purine (264 mg, 0.79 mmol) (3.1) in dry methanol (7 ml) and the solution was heated at 60° C. for 10 h. After filtration, the mixture was evaporated and purified by column chromatography (silica gel, mobile phase chloroform:acetone 9:1). Product was crystallized from ethyl acetate.

Yield: 201 mg, 73%. White crystals, m. p.: 137-139° C. MS ESI+(CV 25) m/z (rel. %): 246 [C$_{11}$H$_{11}$N$_5$O$_2$+H]$^+$ (100), 330 [M+H]$^+$ (91). $^1$H NMR (300 MHz, CDCl$_3$): δ 1.52 (1H, m, THP H5'), 1.60 (2H, mm, THP H4', 5'), 1.75 (1H, d, J=11.8, THP H3'), 1.94 (1H, d, J=11.8, THP H4'), 2.75 (1H, qq, J=11.8, 4.2, THP H3'), 3.59 (1H, tt, J=11.3, 3.6, THP H6'), 3.98 (1H, d, J=11.3, THP H6'), 4.11 (3H, s, —OCH$_3$), 4.69 (2H, d, J=6.2, —NH—CH$_2$-Fur, 5.46 (1H, dd, J=11.2, 2.0, THP H2'), 6.21 (1H, d, J=3.2, Fur H3'), 6.34 (1H, m, Fur H4'), 7.52 (1H, m, Fur H5'), 7.68 (1H, t, J=6.2, HN6), 8.31 (1H, s, H2). $^{13}$C-NMR (300 MHz, DMSO-d$_6$): δ 22.67 (THP C4'), 24.47 (THP C5'), 27.94 (THP C3'), 36.72 (NH—CH$_2$-Fur, 57.08 (—OCH$_3$), 67.72 (THP C6'), 80.79 (THP C2'), 106.39 (Fur C3'), 110.30 (Fur C4'), 114.78 (C5), 141.58 (Fur C5'), 148.81 (C8), 150.58 (C2), 152.09 (C6), 153.23 (Fur C2'), 154.16 (C4).

6-Furfurylamino-8-propyloxy-9-(tetrahydropyran-2-yl)-9H-purine

8-Bromo-6-furfurylamino-9-(tetrahydropyran-2-yl)-9H-purine (303 mg, 0.80 mmol) (3.2) was dissolved in propanol (5 ml). The solution of 0.41 g (10.25 mmol) NaOH in water (13 ml) was added. The reaction mixture was heated under vigorous stirring at 60° C. over night. The reaction mixture was evaporated. The residue was dissolved in ethyl acetate (10 ml), washed with water (3×10 ml), dried with MgSO$_4$, filtered off and evaporated. The crude product was purified by column chromatography (silica gel; mobile phase hexanes:ethyl acetate 3:2, on TLC chromatogram R$_f$=0.14. After column chromatography, the collected fractions were concentrated in vacuo. The product was dried in dessiccator with P$_2$O$_5$. Yellow viscous liquid. Yield: 187 mg, 65%. HPLC R$_t$=15.9 min (75% CH$_3$OH+25% buffer). UV (75% CH$_3$OH+25% buffer) λ$_{max}$ 257 nm, λ$_{min}$ 235 nm. MS ESI+ (CV 10) 358 [M+H]$^+$ (100), (CV 25) m/z (rel. %): 330 [M+H](100), 274 [C$_{13}$H$_{15}$N$_5$O$_2$+H]$^+$ (97). $^1$H NMR (300 MHz, CDCl$_3$): δ 1.00 (3H, t, J=11.8, —CH$_2$CH$_2$CH$_3$), 1.56 (3H, m, THP H4', H5'), 1.80 (3H, m, THP H3', —CH$_2$CH$_2$CH$_3$), 1.96 (1H, d, J=11.9, THP H4'), 2.75 (1H, qq, J=12.0, 3.5, THP H3'), 3.59 (1H, tt, J=11.5, 2.4, THP H6'), 3.98 (1H, d, J=11.0, THP H6'), 4.46 (2H, q, J=4.1, —CH$_2$CH$_2$CH$_3$), 4.69 (2H, d, J=5.7, —NH—CH$_2$-Fur, 5.47 (1H, dd, J=11.1, 1.7, THP H2'), 6.20 (1H, d, J=2.9, Fur H3'), 6.34 (1H, t, J=2.3, Fur H4'), 7.52 (1H, s, Fur H5'), 7.59 (1H, t, J=6.0, HN6), 8.31 (1H, s, H2). $^{13}$C-NMR (300 MHz, DMSO-d$_6$): δ 10.06 (—CH$_2$CH$_2$CH$_3$), 21.61 (—CH$_2$CH$_2$CH$_3$), 22.71 (THP C4'), 24.22 (THP C5'), 27.97 (THP C3'), 36.90 (NH—CH$_2$-Fur, 67.72 (THP C6'), 71.34 (—CH$_2$CH$_2$CH$_3$), 80.74 (THP C2'), 106.38 (Fur C3'), 110.28 (Fur C4'), 114.82 (C5), 141.56 (Fur C5'), 148.81 (C8), 150.48 (C2), 152.02 (C6), 153.25 (Fur C2'), 153.27 (C4).

8-Benzyloxy-6-furfurylamino-9-(tetrahydropyran-2-yl)-9H-purine

Sodium (25 mg, 1.1 mmol) was dissolved in dry benzyl alcohol (3 ml). 8-Bromo-6-furfurylamino-9-(tetrahydropyran-2-yl)-9H-purine (206 mg, 0.54 mmol) (3.2) was added to the sodium benzyl alcoholate. The reaction mixture was heated at 65° C. over night. After cooling, the mixture was diluted with ethyl ether (8 ml). The precipitate was filtered off and the filtrate purified by column chromatography (silica gel; mobile phase hexanes:ethyl acetate 1:1, on TLC chromatogram R$_f$=0.09. After column chromatography, the collected fractions were concentrated in vacuo. The product was precipitated from hexanes, crystallized from methanol and dried in dessiccator with P$_2$O$_5$. White crystals. Yield: 43 mg, 20%. M. p.: 132-135° C. HPLC R$_t$=13.8 min (80% CH$_3$OH+20% buffer), R$_t$=21.3 min (75% CH$_3$OH+25% buffer). UV (75% CH$_3$OH+25% buffer) λ$_{max}$ 268 nm, λ$_{min}$ 236 nm. MS ESI+(CV 10) m/z (rel. %): 406 [M+H]$^+$ (100), 322 [C$_{17}$H$_{15}$N$_5$O$_2$+H]$^+$ (17), (CV 40) m/z (rel. %): 322 [C$_{17}$H$_{15}$N$_5$O$_2$+H]$^+$ (100), 254 [C$_{13}$H$_{12}$N$_5$O]$^+$ (27), 406 [M+H]$^+$ (24). $^1$H NMR (300 MHz, CDCl$_3$): δ 1.57 (2H, s, THP H5'), 1.56 (1H, mm, THP H4'), 1.77 (1H, d, J=13.1, THP H3'), 1.94 (1H, d, J=11.9, THP H4'), 2.76 (1H, qq, J=12.1, 3.3, THP H3'), 3.59 (1H, m, THP H6'), 4.00 (1H, d, J=11.3, THP H6'), 4.71 (2H, d, J=6.2, —NH—CH$_2$-Fur, 5.50 (1H, d, J=10.7, THP H2'), 5.57 (2H, d, J=1.4, O—CH$_2$-Ph), 6.21 (1H, m, Fur H3'), 6.34 (1H, s, Fur H4'), 7.41 (3H, m, HBn), 7.52 (3H, m, Fur H5', HBn), 7.69 (1H, t, J=5.6, HN6), 8.15 (1H, s, H2). $^{13}$C-NMR (300 MHz, DMSO-d$_6$): δ 22.63 (THP C4'), 24.51 (THP C5'), 28.00 (THP C3'), 36.90 (NH—CH$_2$-Fur, 71.02 (—OCH$_2$-Ph), 67.72 (THP C6'), 80.84 (THP C2'), 106.44 (Fur C3'), 110.30 (Fur C4'), 114.82 (C5), 127.79 (Ph), 128.23 (Ph), 128.44 (Ph), 135.61 (Ph), 141.60 (Fur C5'), 148.81 (C8), 150.66 (C2), 152.13 (C6), 153.20 (Fur C2'), 154.16 (C4).

6-Furfurylamino-8-methylsulfanyl-9-(tetrahydropyran-2-yl)-9H-purine

Sodium methanthiolate (0.28 g, 4.00 mmol) was added to a solution of 8-bromo-6-furfurylamino-9-(tetrahydropyran-2-yl)-9H-purine (0.76 g, 2.01 mmol) (3.2) in 2-propanol (8 ml) and the solution was heated at 45° C. for 2.5 h. The mixture was evaporated and diluted with water (6 ml) and ethyl acetate (7 ml). After extraction, the water layer was washed with ethyl acetate (1×7 ml). Collected organic layers were dried with Na$_2$SO$_2$, filtered and evaporated. The crude crystalline product (0.67 g, 96%) was crystallized from 2-propanol (9 ml) and ethanol (8 ml). Light yellow-brownish crystals, m. p.: 153-156° C. HPLC R$_t$=10.3 min (80% CH$_3$OH+20% buffer). UV (80% CH$_3$OH+20% buffer) λ$_{max}$ 285 nm, λ$_{min}$ 250 nm. MS ESI+(CV 10) m/z (rel. %): 716 [2M+Na]$^+$ (100), 346 [M+H]$^+$ (97), (CV 25) m/z (rel. %): 716 [2M+Na]$^+$ (100), 346 [M+H]$^+$ (82), 262 [C$_{11}$H$_{11}$N$_5$OS+H]$^+$ (24), $^1$H NMR (300 MHz, CDCl$_3$): δ 1.54 (1H, m, THP H5'), 1.61 (1H, m, THP H4'), 1.75 (1H, dd, J=11.8, 4.2, THP H3'), 1.95 (1H, d, J=11.8, THP H4'), 2.69 (3H, d, J=0.7, —SCH$_3$), 2.71 (1H, qq, J=11.8, 4.2, THP H3'), 3.64 (1H, tt, J=11.3, 3.6, THP H6'), 4.03 (1H, d, J=11.3, THP H6'), 4.73 (2H, bs, —NH—CH$_2$-Fur, 5.59 (1H, dd, J=11.2, 2.0, THP H2'), 6.23 (1H, dd, J=3.1, 0.7, Fur H3'), 6.35 (1H, m, Fur H4'), 7.53 (1H, m, Fur H5'), 7.94 (1H, t, J=6.2, HN6), 8.16 (1H, s, H2). $^{13}$C-NMR (300 MHz, DMSO-d$_6$): δ 14.25 (—SCH$_3$) 22.41 (THP C4'), 24.40 (THP C5'), 28.45 (THP C3'), 36.47 (NH—CH$_2$-Fur, 67.98 (THP C6'), 82.38 (THP C2'), 106.57 (Fur C3'), 110.33 (Fur C4'), 118.96 (C5), 141.96 (Fur C5'), 149.01 (C8), 150.88 (C4), 151.23 (C2), 152.28 (C6), 152.69 (Fur C2').

8-Dimethylamino-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (3.5) (206 mg, 0.56 mmol) was dissolved in 50% solution of dimethylamine in methanol. The solution was left at room temperature over night, evaporated and purified by column chromatography (silica gel, mobile phase chloroform:acetone 95:5). Yellowish crystals. Yield: 169 mg, 91%. M. p.: 76-79° C. HPLC (flow rate 0.6 ml/min) R$_t$=34.7 min (60% CH$_3$OH+40% buffer). UV (60% CH$_3$OH+40% buffer) λ$_{max}$ 281 nm, λ$_{min}$ 245 nm. MS ESI+ (CV 10) m/z (rel. %): 247 [C$_{12}$H$_{18}$N$_6$+H]$^+$ (100), 331 [M+H]$^+$ (90); (CV 20) m/z (rel. %): 247 [C$_{12}$H$_{18}$N$_6$+H]$^+$ (100), 331 [M+H]$^+$ (37). $^1$H NMR (300 MHz, DMSO-d$_6$): δ 1.58 (3H, mm, THP, H4', 5'), 1.65 (3H, s, =C—CH$_3$), 1.67 (1H, d, J=11.8, THP H3'), 1.69 (3H, s, =C—CH$_3$), 1.94 (1H, m, THP H4'), 2.88 (6H, s, —N—(CH$_3$)$_2$), 3.09 (1H, m, THP H3'), 3.61 (1H, tt, J=11.3, 3.6 Hz THP H6'), 4.03 (1H, m, THP H6'), 4.05 (2H, t, J=6.2, —NH—CH$_2$—CH=), 5.28

(1H, t, J=6.2, —CH$_2$—CH=), 5.32 (1H, dd, J=11.2, 2.0, THP H2'), 7.15 (1H, t, J=6.2, N$^6$H), 8.07 (1H, s, H2). $^{13}$C NMR (300 MHz, DMSO-d$_6$): δ 17.74 (=C—CH$_3$), 22.86 (THP C4'), 24.46 (THP C5'), 25.30 (=C—CH$_3$), 27.43 (THP C3'), 37.78 (—NH—CH$_2$—), 42.21 (—N—(CH$_3$)$_2$), 67.78 (THP C6'), 82.68 (THP C2'), 116.61 (C5), 122.56 (—CH=), 132.69 (=C<), 149.56 (C8), 150.40 (C2), 152.37 (C6), 155.02 (C4).

8-(2-Aminoethylamino)-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (296 mg, 0.81 mmol) (3.5) was dissolved in 2.0 ml of 1,2-diaminoethane and heated at 60° C. under argon for 5 h. The reaction mixture was evaporated and the residue purified by column chromatography (silica gel, mobile phase CHCl$_3$:CH$_3$OH:NH$_4$OH 95:5:0.5, on TLC chromatogram R$_f$=0.19). The product was dried in dessiccator with P$_2$O$_5$ to give white foam. Yield: 260 mg, 93%. HPLC R$_t$=12.8 min (50% CH$_3$OH+50% buffer). UV (50% CH$_3$OH+50% buffer) λ$_{max}$ 282 nm, λ$_{min}$ 241 nm. MS ESI+ (CV 20) m/z (rel. %): 346 [M+H]$^+$ (100), 262 [C$_{12}$H$_{18}$N$_7$+H]$^+$ (12); (CV 30) m/z (rel. %): 262 [C$_{12}$H$_{18}$N$_7$+H]$^+$ (100), 346 [M+H]$^+$ (59). $^1$H NMR (300 MHz, DMSO-d$_6$): δ 1.52 (1H, m, THP H5'), 1.63 (1H, m, THP H4'), 1.64 (1H, m, THP H5'), 1.66 (3H, s, —CH$_3$), 1.67 (1H, m, THP H3'), 1.69 (3H, s, —CH$_3$), 1.93 (1H, m, THP H4'), 2.59 (1H, qq, J=11.7, 4.0 Hz, THP H3'), 2.84 (1H, tt, J=6.2, 2.2 Hz, —CH$_2$CH$_2$NH$_2$), 3.42 (3H, m, —CH$_2$CH$_2$NH$_2$), 3.52 (2H, m, —CH$_2$CH$_2$NH$_2$), 3.66 (1H, t, J=11.7 Hz, THP H6'), 4.02 (1H, m, THP H6'), 4.4 (2H, s (br), —NH—CH$_2$—CH=), 5.28 (1H, t, J=6.8, —NH—CH$_2$—CH=), 5.51 (1H, d, J=11.7 Hz, THP H2'), 6.48 (1H, t, J=6.0 Hz, —NH—CH$_2$—CH$_2$—), 6.81 (1H, t, J=6.0 Hz, —NH—CH$_2$—CH=), 7.97 (1H, s, H2). $^{13}$C NMR (300 MHz, DMSO-d$_6$): δ 17.77 (—CH$_3$), 22.58 (THP C4'), 24.38 (THP C5'), 25.38 (—CH$_3$), 28.32 (THP C3'), 37.88 (—NH—CH$_2$—CH=), 40.57 (—CH$_2$CH$_2$NH$_2$), 44.37 (—NH—CH$_2$CH$_2$—), 67.90 (THP C6'), 81.18 (THP C2'), 116.86 (C5), 122.87 (—CH=), 132.60 (—CH$_2$CH=C), 148.50 (C8), 148.77 (C2), 150.88 (C4), 151.07 (C6).

8-(3-Aminopropylamino)-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (331 mg, 0.90 mmol) (3.5) was dissolved in 4.0 ml of 2-propanol, 1.4 ml (16.7 mmol) of 1,3-diaminopropane and 0.15 ml (1.1 mmol) triethylamine was added and the solution heated under argon at 65° C. for 16 h. After cooling, the reaction mixture was left in refrigerator for 3 h. White crystals of salts were filtered off. The filtrate was evaporated in vacuo and the residue purified by column chromatography (silica gel, mobile phase CHCl$_3$:CH$_3$OH:NH$_4$OH 9:1:0.1, on TLC chromatogram R$_f$=0.21). The product was dried in dessiccator with P$_2$O$_5$ to give yellowish viscous liquid. Yield: 252 mg, 78%. HPLC R$_t$=14.0 min (50% CH$_3$OH+50% buffer). UV (50% CH$_3$OH+50% buffer) λ$_{max}$ 283 nm, λ$_{min}$ 243 nm. MS ESI+ (CV 15) m/z (rel. %): 360 [M+H]$^+$ (100), 276 [C$_{13}$H$_{20}$N$_7$+H]$^+$ (13); (CV 45) m/z (rel. %): 276 [C$_{13}$H$_{20}$N$_7$+H]$^+$ (100), 208 [C$_5$H$_{14}$N$_7$]$^+$ (45), 360 [M+H]$^+$ (28). $^1$H NMR (300 MHz, DMSO-d$_6$): δ 1.49 (1H, m, THP H5'), 1.64 (5H, m, THP H3', H4', H5', —CH$_2$CH$_2$NH$_2$), 1.65 (3H, s, —CH$_3$), 1.68 (3H, s, —CH$_3$), 1.93 (1H, m, THP H4'), 2.57 (1H, qq, J=12.0, 4.4, THP H3'), 2.64 (2H, t, J=6.3, —CH$_2$CH$_2$CH$_2$NH$_2$), 3.42 (2H, q, J=6.3, —CH$_2$CH$_2$CH$_2$NH$_2$), 3.64 (1H, t, J=10.6, THP H6'), 4.03 (3H, m, THP H6', —NH—CH$_2$—CH=), 5.29 (1H, t, J=6.5, —NH—CH$_2$—CH=), 5.49 (1H, d, J=9.8, THP H2'), 6.65 (1H, bs, N$^8$H—), 6.77 (1H, t, J=5.7, —N$^6$H), 7.95 (1H, s, H2). $^{13}$C NMR (300 MHz, DMSO-d$_6$): δ 17.71 (—CH$_3$), 22.56 (THP C4'), 24.27 (THP C5'), 25.33 (—CH$_3$), 28.22 (THP C3'), 32.23 (—CH$_2$CH$_2$CH$_2$NH$_2$), 37.82 (—NH—CH$_2$—CH=), 39.51 (—CH$_2$CH$_2$NH$_2$), 40.55 (—NH—CH$_2$CH$_2$—), 67.83 (THP C6'), 81.01 (THP C2'), 116.96 (C5), 122.95 (—CH=), 132.37 (—CH$_2$CH=C<), 148.48 (C8), 148.50 (C2), 150.93 (C4), 150.93 (C6).

8-(4-Aminobutylamino)-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (331 mg, 0.90 mmol) (3.5) was dissolved in 4.0 ml of 2-propanol, 0.9 ml (9.0 mmol) of 1,4-diaminobutane and 0.15 ml (1.1 mmol) triethylamine was added and the solution heated under argon at 65° C. for 2 days. The reaction mixture was evaporated in vacuo and dried in dessiccator with P$_2$O$_5$. Crystalline residue was dissolved in 5 ml of future mobile phase. Crystals were filtered off and product from the filtrate purified by column chromatography (mobile phase CHCl$_3$:CH$_3$OH:NH$_4$OH 9:1:0.1). The product was dried in dessiccator with P$_2$O$_5$ to give yellowish viscous liquid. Yield: 264 mg, 78%. HPLC R$_t$=18.2 min (50% CH$_3$OH+50% buffer), R$_t$=8.3 min (60% CH$_3$OH+40% buffer).

UV (50% CH$_3$OH+50% buffer) λ$_{max}$ 283 nm, λ$_{min}$ 243 nm. MS ESI+(CV 15) m/z (rel. %): 374 [M+H]$^+$ (100), 290 [C$_{14}$H$_{22}$N$_7$+H]$^+$ (71); (CV 45) m/z (rel. %): 290 [C$_{14}$H$_{22}$N$_7$+H]$^+$, (100), 374 [M+H]$^+$ (36), 222 [C$_9$H$_{16}$N$_7$]$^+$ (13). $^1$H NMR (300 MHz, DMSO-d$_6$): δ 1.39 (2H, p, J=7.5, —NHCH$_2$CH$_2$CH$_2$—), 1.50 (1H, d, J=7.5, THP H5'), 1.64 (5H, m, THP H3', H4', H5', —NHCH$_2$CH$_2$CH$_2$), 1.65 (3H, s, —CH$_3$), 1.68 (3H, s, —CH$_3$), 1.93 (1H, m, THP H4'), 2.56 (3H, t, J=6.8, THP H3', —NHCH$_2$CH$_2$CH$_2$), 3.34 (2H, t, J=9.0, —CH$_2$CH$_2$CH$_2$—NH$_2$), 3.65 (1H, t, J=10.5, THP H6'), 4.03 (3H, m, THP H6', —NH—CH$_2$—CH=), 5.29 (1H, t, J=6.8, —NH—CH$_2$—CH=), 5.48 (1H, d, J=10.5 Hz, THP H2'), 6.40 (1H, t, J=6.8, —NHCH$_2$CH$_2$), 6.77 (1H, t, J=5.6, —NH—CH$_2$—CH=), 7.95 (1H, s, H2). $^{13}$C NMR (300 MHz, DMSO-d$_6$): δ 17.71 (—CH$_3$), 22.66 (THP C4'), 24.27 (THP C5'), 25.33 (—CH$_3$), 26.54 (Bu), 28.24 (THP C3'), 30.64 (Bu), 37.82 (—NH—CH$_2$—CH=), 41.40 (Bu), 42.19 (Bu), 67.83 (THP C6'), 81.06 (THP C2'), 117.03 (C5), 122.95 (—CH=), 132.37 (—CH$_2$CH=C<), 148.49 (C8), 148.67 (C2), 150.89 (C4), 151.00 (C6).

8-(6-Aminohexylamino)-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (321 mg, 0.88 mmol) (Example 3) was dissolved in 4.0 ml of 2-propanol and 1.0 g (8.7 mmol) of 1,6-diaminohexane was added. The solution was heated under argon at 65° C. for 4 days. The reaction mixture was evaporated in vacuo and dried in dessiccator with P$_2$O$_5$. Crystalline residue was dissolved in 4 ml of future mobile phase. Crystals were filtered off and product from the filtrate separated by column chromatography (mobile phase CHCl$_3$:CH$_3$OH:NH$_4$OH 9:1:0.1). The product was dried in dessiccator with P$_2$O$_5$ to give light yellowish glassy substance. Yield: 289 mg, 82%. HPLC R$_t$=11.8 min (60% CH$_3$OH+40% buffer). UV (60% CH$_3$OH+40% buffer) λ$_{max}$ 285 nm, λ$_{min}$ 244 nm. MS ESI+(CV 15) m/z (rel. %): 402 [M+H]$^+$ (100), 318 [C$_{16}$H$_{26}$N$_7$+H]$^+$ (36); (CV 35) m/z (rel. %): 250 [C$_{11}$H$_{20}$N$_7$]$^+$ (100), 318 [C$_{16}$H$_{26}$N$_7$+H]$^+$, (90), 402 [M+H]$^+$ (26). $^1$H NMR (300 MHz, DMSO-d$_6$): δ 1.32 (6H, p, J=7.5, Hex), 1.50 (1H, d, J=7.3, THP H5'), 1.64 (5H, m, THP H3', H4', H5', Hex), 1.65 (3H, s, —CH$_3$), 1.68 (3H, s, —CH$_3$), 1.93 (1H, m, THP H4'), 2.50 (2H, q, J=1.8, Hex), 2.60 (1H, m, THP H3'), 3.34 (2H, q, J=7.1, Hex), 3.65 (1H, t, J=11.0 Hz, THP H6'), 3.99 (2H, bs, —NH—CH$_2$—CH=), 4.05 (1H, d, J=7.1, THP H6'), 5.29 (1H, t, J=6.3, —NH—CH$_2$—CH=), 5.49 (1H, d, J=10.4, THP H2'), 6.30 (1H, t, J=5.6, —N$^8$H), 6.81 (1H, t, J=5.9, —NH—CH$_2$—CH=), 7.95 (1H, s, H2). $^{13}$C NMR (300 MHz, DMSO-d$_6$): δ 17.70 (—CH$_3$), 22.57 (THP C4'), 24.32 (THP C5'), 25.32 (—CH$_3$), 28.24 (THP C3'), 26.11 (Hex), 26.32 (Hex), 28.95 (Hex), 33.23 (Hex), 37.84 (—NH—CH$_2$—CH=), 41.52 (Hex), 42.14 (Hex), 67.83 (THP C6'), 81.05 (THP C2'), 117.02 (C5), 122.95 (—CH=), 132.36 (—CH$_2$CH=C<), 148.50 (C8), 148.67 (C2), 150.87 (C4), 150.96 (C6).

8-(2-Hydroxyethylamino)-6-(3-methylbut-2-en-1-ylamino)-9-(tetrahydropyran-2-yl)-9H-purine 8-Bromo-6-(3-methylbut-2-en-1-ylamino)-9-(tetrahydropyran-2-yl)-9H-purine (246 mg, 0.67 mmol) (Example 3) was dissolved in ethanolamine (2.0 ml). The reaction mixture was heated at 80° C. for 1.5 h, evaporated and the residue purified by column chromatography (silica gel; mobile phase chloroform:methanol 95:5). The product was dried in dessiccator with P$_2$O$_5$. Light yellow viscous substance. Yield: 180 mg, 76%. HPLC (flow rate 0.6 ml/min) R$_t$=14.4 min (60% CH$_3$OH+40% buffer). UV (60% CH$_3$OH+40% buffer) λ$_{max}$ 284 nm. MS ESI+(CV 20) m/z (rel. %): 347 [M+H]$^+$ (100), 263 [C$_{12}$H$_{19}$N$_6$O+H]$^+$ (26); (CV 35) m/z (rel. %): 347 [M+H]$^+$ (100), 263 [C$_{12}$H$_{19}$N$_6$O+H]$^+$ (100). $^1$H (500 MHz, DMSO-d$_6$): 1.46-1.49 (1H, m), 1.56-1.63 (9H, m), 1.87-1.88 (1H, m), 2.45-2.50 (m, 1H), 3.36-3.40 (2H, m), 3.55-3.62 (3H, m), 3.96-3.99 (3H, m), 5.23-5.28 (1H, m), 5.48 (1H, dd, J=10.70 Hz, J=1.83 Hz), 6.26 (1H, t, J=5.50 Hz), 6.71 (1H, d, J=6.11 Hz), 7.92 (1H, s). $^{13}$C (125 MHz, DMSO-d$_6$): 18.3, 23.0, 24.9, 25.9, 28.9, 38.4, 45.3, 60.2, 68.3, 68.5, 81.8, 117.4, 123.4, 133.1, 149.3, 151.6, 151.7.

8-Amino-6-(3-methylbut-2-en-1-ylamino)-chloro-9-(tetrahydropyran-2-yl)-9H-purine 8-Amino-6-chloro-9-(tetrahydropyran-2-yl)-9H-purine (72 mg, 0.28 mmol) (Ex. 4.16.1) and 3-methylbut-2-en-1-amine hydrochloride (60 mg, 0.55 mmol) were dissolved in 1-propanol (5 ml) and diisopropylethylamine (194 μl, 1.13 mmol). The mixture was heated at 110° C. for 90 h. The mixture was evaporated and the residue mixed with intended mobile phase (ethyl acetate:acetone:NH$_4$OH 9:1:0.1). The arisen solid was filtered off, the filtrate evaporated and the residue purified by column chromatography (silica gel; mobile phase ethyl acetate:acetone:NH$_4$OH 9:1:0.1). White solid. Yield: 21 mg, 24%. HPLC R$_t$=12.3 min (70% CH$_3$OH+30% buffer). UV (70% CH$_3$OH+30% buffer) λ$_{max}$ 280 nm, λ$_{min}$ 239 nm. MS ESI+(CV 20) m/z (rel. %): 303 [M+H]$^+$ (100), 219 [C$_{10}$H$_{14}$N$_6$+H]$^+$ (13); (CV 40) m/z (rel. %): 219 [C$_{10}$H$_{14}$N$_6$+H]$^+$ (100), 303 [M+H]$^+$ (77), 163 [C$_6$H7N$_6$]+(12). $^1$H NMR (300 MHz, DMSO-d$_6$): δ 1.49 (1H, d, J=7.6, THP H5'), 1.64 (3H, m, THP H3', H4', H5'), 1.64 (3H, s, —CH$_3$), 1.66 (3H, s, —CH$_3$), 1.93 (1H, m, THP H4'), 2.64 (1H, d, J=11.4, THP H3'), 3.65 (1H, t, J=10.5 Hz, THP H6'), 3.98 (1H, s, THP H6'), 4.03 (2H, d, J=5.6, —NH—CH$_2$—CH=), 5.27 (1H, t, J=7.6, —NH—CH$_2$—CH=), 5.48 (1H, d, J=10.5, THP H2'), 6.31 (2H, s, —N$^8$H2), 6.71 (1H, t, J=5.7, —NH—CH$_2$—CH=), 7.95 (1H, s, H2). $^{13}$C NMR (300 MHz, DMSO-d$_6$): δ 17.77 (—CH$_3$), 22.60 (THP C4'), 24.30 (THP C5'), 25.31 (—CH$_3$), 28.21 (THP C3'), 37.96 (—NH—CH$_2$—CH=), 67.77 (THP C6'), 81.18 (THP C2'), 116.99 (C5), 122.92 (—CH=), 132.39 (—CH$_2$CH=C), 148.43 (C8), 148.43 (C2), 150.95 (C4), 151.02 (C6).

8-Methoxy-6-(3-methylbut-2-en-1-ylamino)-9-(tetrahydropyran-2-yl)-9H-purine

Potassium tert-butoxide (103 mg; 0.92 mmol) was dissolved in dry methanol (2.0 ml). 8-Bromo-6-(3-methylbut-2-en-1-ylamino)-9-(tetrahydropyran-2-yl)-9H-purine (3.5) (248 mg, 0.68 mmol) was added to the solution. The reaction mixture was heated at 45° C. for 13 h. After cooling, the mixture was placed in a refrigerator over night, filtered and evaporated. The residue was purified by column chromatography (silica gel; mobile phase chloroform:acetone 9:1, on TLC chromatogram R$_f$=0.14). The product was dried in dessiccator with P$_2$O$_5$. Light yellow viscous substance. Yield: 170 mg, 79%. HPLC R$_t$=10.8 min (80% CH$_3$OH+ 20% buffer). MS ESI+(CV 12) m/z (rel. %): 318 [M+H]$^+$ (100); (CV 25) m/z (rel. %): 234 [C$_{11}$H$_{15}$N$_5$O+H]$^+$ (100). 318 [M+H]$^+$ (76).

8-(3-Aminopropyloxy)-6-(3-methylbut-2-en-1-ylamino)-9-(tetrahydropyran-2-yl)-9H-purine Sodium hydride in mineral oil (34%) (67 mg, 0.95 mmol) had been dissolving, under argon, in a mixture of 3-amino-1-propanol (66 μl, 0.86 mmol) and dimethylformamide (5 ml) for 1.5 h. Then 8-chloro-6-(3-methylbut-2-en-1-ylamino)-9-(tetrahydropyran-2-yl)-9H-purine (3.4) (214 mg, 0.66 mmol) was added. The reaction mixture was stirred under argon at room temperature for 4 days, evaporated and the residue purified by column chromatography (silica gel; gradient elution, starting with chloroform as a mobile phase, ending with mobile phase chloroform:methanol:NH$_4$OH 9:1:0.1). The product was dried in dessiccator with P$_2$O$_5$. Yellow viscous substance.

Yield: 156 mg, 65%. HPLC R$_t$=7.7 min (60% CH$_3$OH+ 40% buffer). UV (60% CH$_3$OH+40% buffer) λ$_{max}$ 268 nm, λ$_{min}$ 233 nm. MS ESI+(CV 18) m/z (rel. %): 361 [M+H]$^+$ (100); 277 [C$_{13}$H$_{20}$N$_6$O+H]$^+$ (15). (CV 29) m/z (rel. %): 277 [C$_{13}$H$_{20}$N$_6$O+H]$^+$ (100), 361 [M+H]$^+$ (96); 220 [C$_{10}$H$_{13}$N$_5$O+H]$^+$ (38). $^1$H NMR (300 MHz, DMSO-d$_6$): δ 1.52 (1H, m, THP H5'), 1.64 (2H, m, THP H4', H5'), 1.65 (3H, s, —CH$_3$), 1.68 (3H, s, —CH$_3$), 1.75 (1H, m, THP H3'), 1.85 (2H, t, J=6.5, —OCH$_2$CH$_2$CH$_2$NH$_2$), 1.94 (1H, m, THP H4'), 2.70 (2H, t, J=6.6, —OCH$_2$CH$_2$CH$_2$NH$_2$), 2.73 (1H, m, THP H3'), 3.56 (1H, m, THP H6'), 3.97 (1H, d, J=11.3, THP H6), 4.05 (2H, bs, —NH—CH$_2$—CH=), 4.53 (2H, q, J=5.4, —OCH$_2$CH$_2$CH$_2$NH$_2$), 5.28 (1H, t, J=6.5, —NH—CH$_2$—CH=), 5.44 (1H, d, J=9.5, THP H2'), 7.26 (1H, t, J=5.7, —N$^6$H), 8.10 (1H, s, H2).

$^{13}$C NMR (300 MHz, DMSO-d$_6$): δ 17.71 (—CH$_3$), 22.72 (THP C4'), 24.53 (THP C5'), 25.30 (—CH$_3$), 27.98 (THP C3'), 32.03 (—OCH$_2$CH$_2$CH$_2$NH$_2$), 38.00 (—NH—CH$_2$—CH=), 67.71 (THP C6'), 68.06 (—OCH$_2$CH$_2$CH$_2$NH$_2$), 80.68 (THP C2'), 114.62 (C5), 122.50 (—CH=), 132.72 (—CH$_2$CH=C<), 150.61 (C8), 150.61 (C2), 152.17 (C4), 153.48 (C6).

(E)-8-Dimethylamino-6-(4-hydroxy-3-methylbut-2-en-1-ylamino)-9-(tetrahydropyran-2-yl)-9H-purine (E)-8-Chloro-6-(4-hydroxy-3-methylbut-2-en-1-ylamino)-9-(tetrahydropyran-2-yl)-9H-purine (3.6) (234 mg, 0.69 mmol) was dissolved in 50% solution of dimethylamine in methanol (2.5 ml). The solution was left at room temperature for 2 days, evaporated and extracted in ethyl acetate (3 ml):water (3 ml). Water layer reextracted with ethyl acetate (2×3 ml). Collected ethyl acetate layers were dried with $MgSO_4$ and evaporated. The product was dried in dessiccator with $P_2O_5$. White crystals. Yield: 217 mg, 90%. M. p.: 110-114° C. HPLC $R_t$=13.8 min (60% $CH_3OH$+40% buffer). UV (60% $CH_3OH$+40% buffer) $\lambda_{max}$ 281 nm, $\lambda_{min}$ 245 nm. MS ESI+(methanol) (CV 25) m/z (rel. %): 347 [M+H]$^+$ (100), 715 [2M+Na]$^+$ (71), 263 $[C_{12}H_{18}N_6O+H]^+$ (15); (CV 40) m/z (rel. %): 369 [M+Na]$^+$ (100), 347 [M+H]$^+$ (88), 263 $[C_{12}H_{18}N_6O+H]^+$ (88), 715 [2M+Na]$^+$ (53). $^1$H NMR (300 MHz, DMSO-$d_6$): δ 1.49 (1H, m, THP, H5'), 1.56 (1H, m, THP, H4'), 1.61 (1H, m, THP, H3'), 1.66 (3H, s, =C—$CH_3$), 1.67 (1H, m, THP H3'), 1.93 (1H, m, THP H4'), 2.88 (6H, s, —N—$(CH_3)_2$), 3.09 (1H, qq, J=12.1, 3.6, THP H3'), 3.61 (1H, tt, J=11.3, 3.6, THP H6'), 3.78 (2H, d, J=5.7, —$CH_2$—OH), 4.03 (1H, d, J=11.3, THP H6'), 4.11 (2H, t, J=5.7, —NH—$CH_2$—CH=), 4.71 (1H, t, J=5.7, —OH), 5.32 (1H, dd, J=11.3, 2.2, THP H2'), 5.50 (1H, tt, J=6.7, 1.7, —$CH_2$—CH=), 7.20 (1H, t, J=5.7, N$^6$H), 8.08 (1H, s, H2). $^{13}$C NMR (300 MHz, DMSO-$d_6$): δ 13.57 (=C—$CH_3$), 22.90 (THP C4'), 24.49 (THP C5'), 27.47 (THP C3'), 37.42 (—NH—$CH_2$—), 42.23 (—N—$(CH_3)_2$), 65.88 (—$CH_2$—OH), 67.84 (THP C6'), 82.74 (THP C2'), 116.68 (C5), 121.17 (—CH=), 132.91 (=C<), 149.57 (C4), 150.44 (C2), 152.44 (C6), 155.10 (C8).

(E)-6-(4-Hydroxy-3-methylbut-2-en-1-ylamino)-8-methoxy-9-(tetrahydropyran-2-yl)-9H-purine (E)-8-Chloro-6-(4-hydroxy-3-methylbut-2-en-1-ylamino)-9-(tetrahydropyran-2-yl)-9H-purine (3.6) (190 mg, 0.56 mmol) was dissolved in methanol (1.6 ml) and 30% aqueous NaOH (1.6 ml) was added. The mixture was heated at 60° C. under vigorous stirring for 0.5 h. Then, the mixture was evaporated, dissolved in ethyl acetate (5 ml) and washed with water. After drying and concentration in vacuo, the crude product was purified by column chromatography (silica gel, mobile phase chloroform:acetone 9:1, on TLC chromatogram $R_f$=0.10). The product was dried in dessiccator with $P_2O_5$. White crystals. Yield: 83 mg, 44%. M. p.: 126-130° C. MS ESI+(CV 10) m/z (rel. %): 334 [M+H]$^+$ (100); (CV 30) m/z (rel. %): 250 $[C_{11}H_{15}N_5O_2+H]^+$ (100), 334 [M+H]$^+$ (40).

(E)-8-Benzyloxy-6-(4-hydroxy-3-methylbut-2-en-1-ylamino)-9-(tetrahydropyran-2-yl)-9H-purine Sodium (120 mg, 5.2 mmol) was dissolved in dry benzyl alcohol (5 ml). (E)-8-Bromo-6-(4-hydroxy-3-methylbut-2-en-1-ylamino)-9-(tetrahydropyran-2-yl)-9H-purine (3.6) (192 mg, 0.50 mmol) was added to the sodium benzyl alcoholate. The reaction mixture was heated at 65° C. for 2 days. After cooling, the mixture was evaporated diluted with chloroform:acetone 75:25 (5 ml). The precipitate was filtered off and the filtrate purified by column chromatography (silica gel; mobile phase chloroform:acetone 75:25, on TLC chromatogram $R_f$=0.14). After column chromatography, the collected fractions were concentrated in vacuo. The product was dried in dessiccator with $P_2O_5$. Yellowish viscous substance. Yield: 20 mg, 10%. HPLC $R_t$=9.3 min (80% $CH_3OH$+20% buffer), $R_t$=18.9 min (70% $CH_3OH$+30% buffer). UV (70% $CH_3OH$+30% buffer) $\lambda_{max}$ 268 nm, $\lambda_{min}$ 233 nm. MS ESI+(CV 20) m/z (rel. %): 410 [M+H]$^+$ (100); (CV 40) m/z (rel. %): 326 $[C_{17}H_{19}N_5O_2+H]^+$ (100), 406 [M+H]$^+$ (49). $^1$H (500 MHz, DMSO-$d_6$): δ 1.46-1.48 (2H, m), 1.54-1.60 (1H, m), 1.61 (3H, s). 1.70-1.75 (1H, m), 1.82-1.90 (1H, m), 2.71 (1H, dq, J=11.31 Hz, J=3.97 Hz), 3.51-3.56 (1H, m), 3.73 (2H, s), 3.92-3.94 (1H, m), 4.08 (2H, bs), 4.66 (1H, bs), 5.43-5.53 (4H, m), 7.26-7.40 (4H, m), 7.48 (2H, d, J=7.03 Hz), 8.07 (1H, s). $^{13}$C (125 MHz, DMSO-$d_6$): δ 14.8, 23.2, 25.1, 28.6, 38.0, 66.4, 68.1, 68.3, 71.5, 81.4, 115.2, 121.6, 128.3, 128.8, 129.0, 136.2, 137.5, 151.4, 152.9, 153.8.

6-Benzylamino-8-benzyloxy-9-(tetrahydropyran-2-yl)-9H-purine

Sodium (40 mg, 1.7 mmol) was dissolved in dry benzyl alcohol (0.1.0 ml). 8-Bromo-6-benzylamino-9-(tetrahydropyran-2-yl)-9H-purine (3.8) (387 mg, 1.00 mmol) was dissolved in dimethylformamide (3.0 ml) and the solution added dropwise to the sodium benzyl alcoholate solution. The reaction mixture was heated at room temperature under argon atmosphere for 4.5 h. Then, the mixture was neutralized with 2 drops of glacial acetic acid and evaporated. The crude product, in form of white solid, was triturated with ethyl acetate (10 ml), heated in a boiling water bath and filtered. The filtrate was left in a refrigerator for 2 days. The crystals were filtered off and dried in dessiccator with $P_2O_5$. White crystals. Yield: 267 mg, 64%. M. p.: 149-151° C. HPLC $R_t$=13.0 min (85% $CH_3OH$+15% buffer). UV (85% $CH_3OH$+15% buffer) $\lambda_{max}$ 269 nm, $\lambda_{min}$ 234 nm. MS ESI+ (CV 20) m/z (rel. %): 416 [M+H]$^+$ (100); (CV 50) m/z (rel. %): 332 $[C_{17}H_{17}N_5O+H]^+$ (100), 416 [M+H]$^+$ (13). $^1$H NMR (300 MHz, DMSO-$d_6$): δ 1.51 (2H, m, THP H5'), 1.65 (1H, m, THP H4'), 1.77 (1H, d, J=13.1, THP H3'), 1.93 (1H, d, J=12.3, THP H4'), 2.76 (1H, qq, J=12.1, 3.6, THP H3'), 3.58 (1H, m, H6'), 4.05 (1H, d, J=11.3, THP H6'), 4.72 (2H, d, J=1.7, NH—$CH_2$-Ph), 5.50 (1H, dd, J=11.1, 1.7, THP H2'), 5.58 (2H, d, J=11.3, O—$CH_2$-Ph), 7.19 (1H, m, J=6.8, 2.3, Ph H4'), 7.35 (7H, m, Ph), 7.52 (2H, m, Ph), 8.11 (1H, s, H2), 7.82 (1H, bs, N$^6$H). $^{13}$C-NMR (300 MHz, DMSO-$d_6$): δ 22.64 (THP C4'), 24.52 (THP C5'), 28.01 (THP C3'), 43.18 (NH—$CH_2$-Ph), 67.72 (THP C6'), 71.01 (O$CH_2$Ph), 80.84 (THP C2'), 114.56 (C5), 126.41 (Ph C4'), 127.09 (2x) (Ph), 127.78 (2x) (Ph), 128.04 (2x) (Ph), 128.22 (Ph), 128.43 (2x) (Ph), 135.62 (Ph), 140.37 (Ph), 150.76 (2x) (Pur), 152.39 (Pur), 153.41 (Pur).

8-(4-Aminobutylamino)-6-benzylamino)-9-(tetrahydropyran-2-yl)-9H-purine

8-Bromo-6-benzylamino-9-(tetrahydropyran-2-yl)-9H-purine (3.8) (400 mg, 1.03 mmol), 1,4-diaminobutane (1.0 ml, 9.95 mmol) and diisopropylethylamine (0.18 ml, 1.03 mmol) in 2-propanol (5.5 ml) were heated at 80° C. over night and evaporated. The residue was dissolved in a mixture of chloroform (4 ml) and methanol (1 ml), filtered and the filtrate was purified by column chromatography (silica gel; mobile phase chloroform:methanol:$NH_4OH$ 85:15:1.5, on TLC chromatogram $R_f$=0.18). After column chromatography, the collected fractions were concentrated in vacuo. The product was dried in dessiccator with $P_2O_5$. Yellowish viscous substance. Yield: 373 mg, 92%. HPLC $R_t$=13.0 min (60% $CH_3OH$+40% buffer), $R_t$=18.6 min (50% $CH_3OH$+50% buffer), UV (60% $CH_3OH$+40% buffer) $\lambda_{max}$ 285 nm, $\lambda_{min}$ 244 nm. $^1$H NMR (300 MHz, DMSO-d$_6$): δ 1.40 (2H, p, J=7.2, Bu), 1.50 (1H, d, J=7.3, THP H5'), 1.63 (5H, m, THP H3' H4' H5', Bu), 1.93 (1H, bs, THP H4'), 2.56 (2H, t, J=6.8, Bu), 2.57 (1H, qq, covered, THP H3'), 3.35 (2H, m, Bu), 3.65 (1H, t, J=10.6, THP H6'), 4.01 (1H, d, J=10.8, THP H6'), 4.68 (2H, d, J=5.5, NH—CH$_2$-Ph), 5.50 (1H, d, J=9.9, THP H2'), 6.43 (1H, bs, N$^8$H), 7.18 (1H, t, J=6.9, N$^6$H), 7.32 (5H, m, Ph), 7.94 (1H, s, H2). $^{13}$C-NMR (300 MHz, DMSO-d$_6$): δ 22.57 (THP C4'), 24.32 (THP C5'), 26.53 (Bu), 28.25 (THP C3'), 41.34 (Bu), 42.22 (Bu), 43.16 (NH—CH$_2$-Ph), 67.84 (THP C6'), 81.11 (THP C2'), 117.02 (C5), 126.29 (Ph C4'), 127.13 (2x) (Ph), 127.96 (2x) (Ph), 140.85 (Ph), 148.45 (Pur), 148.92 (Pur), 150.96 (Pur), 151.05 (Pur).

TABLE 2

Compounds of this invention prepared according to Example 4

| | Substituent | | | CHN analyses calculated/found | | | ESI-MS |
|---|---|---|---|---|---|---|---|
| No. | R6 | R8 | R9 | % C | % H | % N | [M$^+$H$^+$] |
| 80 | furfurylamino | (CH$_3$)$_2$N | 2-tetrahydropyranyl | 59.6/59.5 | 6.5/6.4 | 24.5/24.7 | 343.4 |
| 81 | benzylamino | (CH$_3$)$_2$N | 2-tetrahydropyranyl | 64.8/64.9 | 6.9/6.7 | 23.9/24.1 | 353.4 |
| 82 | (Z)-(4-hydroxy-3-methylbut-2-en-1-yl)amino | (CH$_3$)$_2$N | 2-tetrahydropyranyl | 58.9/58.6 | 7.6/7.8 | 24.3/24.2 | 347.4 |
| 83 | (4-hydroxy-3-methylbutyl)amino | (CH$_3$)$_2$N | 2-tetrahydropyranyl | 58.6/58.7 | 8.1/8.2 | 24.1/24.4 | 349.5 |
| 84 | 2-fluorobenzylamino | (CH$_3$)$_2$N | 2-tetrahydropyranyl | 61.6/61.8 | 6.3/6.5 | 22.7/22.5 | 371.4 |
| 85 | 3-fluorobenzylamino | (CH$_3$)$_2$N | 2-tetrahydropyranyl | 61.6/61.7 | 6.3/6.4 | 22.7/22.6 | 371.4 |
| 86 | 3-chlorobenzylamino | (CH$_3$)$_2$N | 2-tetrahydropyranyl | 59.0/59.0 | 6.0/5.8 | 21.7/21.5 | 387.9 |
| 87 | 3-bromobenzylamino | (CH$_3$)$_2$N | 2-tetrahydropyranyl | 52.9/52.7 | 5.4/5.2 | 19.5/19.0 | 432.3 |
| 88 | 3-iodobenzylamino | (CH$_3$)$_2$N | 2-tetrahydropyranyl | 47.7/47.9 | 4.9/5.1 | 17.6/17.4 | 479.3 |
| 89 | 4-methylbenzylamino | (CH$_3$)$_2$N | 2-tetrahydropyranyl | 65.6/66.0 | 7.2/7.1 | 22.9/23.4 | 367.5 |
| 90 | 2-methoxybenzylamino | (CH$_3$)$_2$N | 2-tetrahydropyranyl | 62.8/63.0 | 6.9/7.0 | 22.0/22.2 | 383.5 |
| 91 | 3-methoxybenzylamino | (CH$_3$)$_2$N | 2-tetrahydropyranyl | 62.8/62.8 | 6.9/6.9 | 22.0/21.9 | 383.5 |
| 92 | 2,3-dichlorobenzylamino | (CH$_3$)$_2$N | 2-tetrahydropyranyl | 54.2/54.1 | 5.3/5.5 | 20.0/20.4 | 422.3 |
| 93 | 2-hydroxy-3-methoxybenzylamino | (CH$_3$)$_2$N | 2-tetrahydropyranyl | 60.3/60.1 | 6.6/6.5 | 21.1/21.3 | 399.5 |
| 94 | 3,4-dimethoxybenzylamino | (CH$_3$)$_2$N | 2-tetrahydropyranyl | 61.2/61.5 | 6.8/6.9 | 20.4/20.1 | 413.5 |
| 95 | anilino | (CH$_3$)$_2$N | 2-tetrahydropyranyl | 63.9/64.2 | 6.6/.6.9 | 24.8/24.7 | 339.4 |
| 96 | 3-fluoroanilino | (CH$_3$)$_2$N | 2-tetrahydropyranyl | 60.6/60.8 | 5.9/9.1 | 23.6/23.8 | 357.4 |
| 97 | 2-chloroanilino | (CH$_3$)$_2$N | 2-tetrahydropyranyl | 58.0/58.2 | 5.7/5.4 | 22.5/22.3 | 373.9 |
| 98 | 3-methoxyanilino | (CH$_3$)$_2$N | 2-tetrahydropyranyl | 61.9/62.3 | 6.6/6.5 | 22.8/22.7 | 369.4 |
| 99 | 3-methylanilino | (CH$_3$)$_2$N | 2-tetrahydropyranyl | 64.8/65.2 | 6.9/7.0 | 23.9/24.1 | 353.4 |
| 100 | furfurylamino | CH$_2$=CHCH$_2$NH | 2-tetrahydropyranyl | 61.0/61.6 | 6.3/6.5 | 23.7/23.9 | 355.4 |
| 101 | benzylamino | CH$_2$=CHCH$_2$NH | 2-tetrahydropyranyl | 65.9/65.8 | 6.6/6.5 | 23.1/23.4 | 365.5 |
| 102 | furfurylamino | NH$_2$ | 2-tetrahydropyranyl | 57.3/57.7 | 5.8/5.7 | 26.7/26.8 | 315.4 |
| 103 | benzylamino | NH$_2$ | 2-tetrahydropyranyl | 63.0/63.2 | 6.2/6.2 | 25.9/26.1 | 325.4 |
| 104 | (Z)-(4-hydroxy-3-methylbut-2-en-1-yl)amino | NH$_2$ | 2-tetrahydropyranyl | 56.6/56.8 | 7.0/7.1 | 26.4/26.6 | 319.4 |
| 105 | (E)-(4-hydroxy-3-methylbut-2-en-1-yl)amino | NH$_2$ | 2-tetrahydropyranyl | 56.6/56.1 | 7.0/7.2 | 26.4/26.5 | 319.4 |
| 106 | (4-hydroxy-3-methylbutyl) amino | NH$_2$ | 2-tetrahydropyranyl | 56.2/55.7 | 7.6/7.5 | 26.2/26.1 | 321.4 |
| 107 | (3-methylbut-2-en-1-yl)amino | NH$_2$ | 2-tetrahydropyranyl | 59.2/59.7 | 8.0/7.8 | 27.6/27.5 | 305.4 |
| 108 | 3-fluorobenzylamino | NH$_2$ | 2-tetrahydropyranyl | 59.6/60.1 | 5.6/5.4 | 24.6/24.6 | 343.4 |
| 109 | 2-chlorobenzylamino | NH$_2$ | 2-tetrahydropyranyl | 56.9/57.3 | 5.3/5.1 | 23.4/23.5 | 359.8 |
| 110 | 2-bromobenzylamino | NH$_2$ | 2-tetrahydropyranyl | 50.6/50.4 | 4.8/4.9 | 20.8/21.1 | 404.3 |
| 111 | 3-methoxybenzylamino | NH$_2$ | 2-tetrahydropyranyl | 61.0/61.2 | 6.3/6.4 | 23.7/24.0 | 355.4 |
| 112 | 3-aminobenzylamino | NH$_2$ | 2-tetrahydropyranyl | 60.2/60.0 | 6.2/6.5 | 28.9/28.7 | 340.4 |
| 113 | 3-hydroxybenzylamino | NH$_2$ | 2-tetrahydropyranyl | 60.0/60.1 | 5.9/6.1 | 24.7/24.6 | 341.4 |
| 114 | 4-hydroxybenzylamino | NH$_2$ | 2-tetrahydropyranyl | 60.0/60.3 | 5.9/5.7 | 24.7/24.7 | 341.4 |
| 115 | 2,3-dihydroxybenzylamino | NH$_2$ | 2-tetrahydropyranyl | 57.3/57.7 | 5.7/5.7 | 23.6/23.5 | 357.4 |
| 116 | 3,4-dihydroxybenzylamino | NH$_2$ | 2-tetrahydropyranyl | 57.3/57.9 | 5.7/5.8 | 23.6/23.7 | 357.4 |
| 117 | 3-hydroxy-4-methoxybenzylamino | NH$_2$ | 2-tetrahydropyranyl | 58.4/58.0 | 6.0/5.9 | 22.7/22.6 | 371.4 |
| 118 | anilino | NH$_2$ | 2-tetrahydropyranyl | 61.9/70.3 | 5.9/5.8 | 27.1/27.4 | 311.4 |
| 119 | 3-fluoroanilino | NH$_2$ | 2-tetrahydropyranyl | 58.5/58.9 | 5.2/5.3 | 25.6/25.8 | 329.4 |
| 120 | 3-hydroxyanilino | NH$_2$ | 2-tetrahydropyranyl | 58.9/58.5 | 5.6/5.7 | 25.8/25.7 | 327.4 |
| 121 | 3-aminoanilino | NH$_2$ | 2-tetrahydropyranyl | 59.1/59.7 | 5.9/6.1 | 23.1/22.7 | 326.4 |
| 122 | 3,4-dihydroxyanilino | NH$_2$ | 2-tetrahydropyranyl | 56.1/56.6 | 5.3/5.0 | 24.6/24.8 | 343.4 |
| 123 | 3-methoxyanilino | NH$_2$ | 2-tetrahydropyranyl | 60.0/59.3 | 5.9/5.8 | 24.7/24.7 | 341.4 |
| 124 | furfurylamino | CH$_3$O | 2-tetrahydropyranyl | 58.4/58.8 | 5.8/5.8 | 21.3/21.4 | 330.4 |
| 125 | benzylamino | CH$_3$O | 2-tetrahydropyranyl | 63.7/63.5 | 6.2/6.4 | 20.6/20.8 | 340.4 |
| 126 | (E)-(4-hydroxy-3-methylbut-2-en-1-yl)amino | CH$_3$O | 2-tetrahydropyranyl | 57.6/57.4 | 7.0/7.2 | 21.0/21.2 | 334.4 |
| 127 | (3-methylbut-2-en-1-yl)amino | CH$_3$O | 2-tetrahydropyranyl | 60.6/61.0 | 7.3/7.2 | 22.1/22.2 | 318.4 |
| 128 | 3-methoxybenzylamino | CH$_3$O | 2-tetrahydropyranyl | 61.8/61.6 | 6.3/6.3 | 19.0/19.2 | 370.4 |
| 129 | 3-hydroxybenzylamino | CH$_3$O | 2-tetrahydropyranyl | 60.8/60.5 | 6.0/6.2 | 19.7/19.9 | 356.4 |
| 130 | 3-fluorobenzylamino | CH$_3$O | 2-tetrahydropyranyl | 60.5/60.1 | 5.6/5.7 | 19.6/19.8 | 358.4 |
| 131 | 4-hydroxybenzylamino | CH$_3$O | 2-tetrahydropyranyl | 60.8/61.3 | 6.0/5.9 | 19.7/19.9 | 356.4 |
| 132 | 3-methoxyanilino | CH$_3$O | 2-tetrahydropyranyl | 60.8/61.2 | 6.0/6.2 | 19.7/20.0 | 356.4 |
| 133 | furfurylamino | C$_3$H$_7$O | 2-tetrahydropyranyl | 60.5/61.0 | 6.5/6.4 | 19.6/19.7 | 358.4 |
| 134 | benzylamino | C$_3$H$_7$O | 2-tetrahydropyranyl | 65.4/65.2 | 6.9/6.8 | 19.1/19.0 | 368.5 |
| 135 | furfurylamino | C$_6$H$_5$—CH$_2$O | 2-tetrahydropyranyl | 65.2/65.4 | 5.7/5.9 | 17.3/17.5 | 406.5 |
| 136 | benzylamino | C$_6$H$_5$—CH$_2$O | 2-tetrahydropyranyl | 69.4/69.3 | 6.1/6.0 | 16.9/16.7 | 416.5 |
| 137 | (E)-(4-hydroxy-3-methylbut-2-en-1-yl)amino | C$_6$H$_5$—CH$_2$O | 2-tetrahydropyranyl | 64.5/64.6 | 6.7/6.8 | 17.1/17.2 | 410.5 |
| 138 | 3-hydroxybenzylamino | C$_6$H$_5$—CH$_2$O | 2-tetrahydropyranyl | 66.8/66.5 | 5.8/5.9 | 16.2/16.3 | 432.5 |
| 139 | 3-methoxyanilino | C$_6$H$_5$—CH$_2$O | 2-tetrahydropyranyl | 66.8/66.6 | 5.8/5.8 | 16.2/16.4 | 432.5 |
| 140 | furfurylamino | SH | 2-tetrahydropyranyl | 54.4/54.6 | 5.2/5.4 | 21.1/21.3 | 332.4 |
| 141 | benzylamino | SH | 2-tetrahydropyranyl | 59.8/60.1 | 5.6/5.4 | 20.5/20.8 | 342.4 |
| 142 | 3-methoxybenzylamino | SH | 2-tetrahydropyranyl | 58.2/58.7 | 5.7/5.5 | 18.9/18.7 | 372.5 |

TABLE 2-continued

Compounds of this invention prepared according to Example 4

| | Substituent | | | CHN analyses calculated/found | | | ESI-MS |
|---|---|---|---|---|---|---|---|
| No. | R6 | R8 | R9 | % C | % H | % N | [M+H+] |
| 143 | anilino | SH | 2-tetrahydropyranyl | 58.7/58.5 | 5.2/5.3 | 21.4/21.5 | 328.4 |
| 144 | 4-methoxyanilino | SH | 2-tetrahydropyranyl | 57.1/57.2 | 5.4/5.5 | 19.6/19.8 | 358.4 |
| 145 | furfurylamino | CH$_3$S | 2-tetrahydropyranyl | 55.6/55.6 | 5.5/5.5 | 20.3/20.3 | 346.4 |
| 146 | (E)-(4-hydroxy-3-methylbut-2-en-1-yl)amino | CH$_3$S | 2-tetrahydropyranyl | 55.0/55.3 | 6.6/6.4 | 20.0/20.2 | 350.5 |
| 147 | (3-methylbut-2-en-1-yl)amino | CH$_3$S | 2-tetrahydropyranyl | 57.6/57.3 | 7.0/7.2 | 21.0/20.8 | 334.5 |
| 148 | benzylamino | CH$_3$S | 2-tetrahydropyranyl | 60.8/60.9 | 6.0/6.4 | 19.7/19.6 | 356.5 |
| 149 | 3-hydroxybenzylamino | CH$_3$S | 2-tetrahydropyranyl | 58.2/58.4 | 5.7/5.8 | 18.9/19.0 | 372.5 |
| 150 | 3-methoxybenzylamino | CH$_3$S | 2-tetrahydropyranyl | 59.2/59.0 | 6.0/6.2 | 18.2/17.9 | 386.5 |
| 151 | 3-fluorobenzylamino | CH$_3$S | 2-tetrahydropyranyl | 57.9/58.1 | 5.4/5.5 | 18.8/18.5 | 374.5 |
| 152 | furfurylamino | CH$_3$SO$_2$ | 2-tetrahydropyranyl | 50.9/50.5 | 5.1/5.0 | 18.6/18.8 | 378.4 |
| 153 | benzylamino | CH$_3$SO$_2$ | 2-tetrahydropyranyl | 55.8/55.7 | 5.5/5.3 | 18.1/17.9 | 388.5 |
| 154 | anilino | CH$_3$SO$_2$ | 2-tetrahydropyranyl | 54.7/54.9 | 5.1/5.3 | 18.8/18.8 | 374.4 |
| 155 | 3-fluoroanilino | CH$_3$SO$_2$ | 2-tetrahydropyranyl | 52.2/52.4 | 4.6/4.8 | 17.9/18.2 | 392.4 |
| 156 | 3-methoxyanilino | CH$_3$SO$_2$ | 2-tetrahydropyranyl | 53.6/54.0 | 5.3/5.5 | 17.4/17.8 | 404.5 |
| 157 | furfurylamino | NH$_2$(CH$_2$)$_3$S | 2-tetrahydropyranyl | 55.7/55.8 | 6.2/6.6 | 21.6/21.5 | 389.5 |
| 158 | benzylamino | NH$_2$(CH$_2$)$_3$S | 2-tetrahydropyranyl | 60.3/60.2 | 6.6/6.9 | 21.1/21.0 | 399.5 |
| 159 | furfurylamino | OH | 2-tetrahydropyranyl | 57.1/57.3 | 5.4/5.4 | 22.2/21.8 | 316.3 |
| 160 | benzylamino | OH | 2-tetrahydropyranyl | 62.8/62.7 | 5.9/6.2 | 21.5/21.3 | 326.4 |
| 161 | (E)-(4-hydroxy-3-methylbut-2-en-1-yl)amino | OH | 2-tetrahydropyranyl | 56.4/56.1 | 6.6/6.7 | 21.9/22.2 | 320.4 |
| 162 | 3-hydroxybenzylamino | OH | 2-tetrahydropyranyl | 59.8/60.0 | 5.6/5.3 | 20.5/20.9 | 342.4 |
| 163 | 3-methoxybenzylamino | OH | 2-tetrahydropyranyl | 60.8/60.9 | 6.0/5.8 | 19.7/19.9 | 356.4 |
| 164 | anilino | OH | 2-tetrahydropyranyl | 61.7/61.5 | 5.5/5.7 | 22.5/22.1 | 312.4 |
| 165 | 3-hydroxyanilino | OH | 2-tetrahydropyranyl | 58.7/58.6 | 5.2/5.4 | 21.4/21.3 | 328.4 |
| 166 | furfurylamino | H$_2$NCH$_2$ | 2-tetrahydropyranyl | 58.5/58.4 | 6.1/6.4 | 25.6/25.4 | 329.4 |
| 167 | furfurylamino | CH$_3$OCO | 2-tetrahydropyranyl | 57.1/57.1 | 5.4/5.6 | 19.6/19.8 | 358.4 |
| 168 | benzylamino | CH$_3$OCO | 2-tetrahydropyranyl | 62.1/62.3 | 5.8/5.6 | 19.1/18.6 | 368.4 |
| 169 | furfurylamino | CH$_3$CH$_2$OCO | 2-tetrahydropyranyl | 58.2/58.5 | 5.7/5.3 | 18.9/18.7 | 372.4 |
| 170 | furfurylamino | NH$_2$(CH$_2$)$_2$NH | 2-tetrahydropyranyl | 57.1/57.2 | 6.5/6.2 | 27.4/27.2 | 358.4 |
| 171 | benzylamino | NH$_2$(CH$_2$)$_2$NH | 2-tetrahydropyranyl | 62.1/62.3 | 6.9/7.2 | 26.7/26.4 | 368.5 |
| 172 | (3-methylbut-2-en-1-yl)amino | NH$_2$(CH$_2$)$_2$NH | 2-tetrahydropyranyl | 59.1/59.3 | 7.9/8.1 | 28.4/28.2 | 346.5 |
| 173 | (E)-(4-hydroxy-3-methylbut-2-en-1-yl)amino | NH$_2$(CH$_2$)$_2$NH | 2-tetrahydropyranyl | 56.5/56.5 | 7.5/7.7 | 27.1/27.2 | 362.5 |
| 174 | 4-hydroxybenzylamino | NH$_2$(CH$_2$)$_2$NH | 2-tetrahydropyranyl | 59.5/60.0 | 6.6/6.6 | 25.6/25.2 | 384.5 |
| 175 | anilino | NH$_2$(CH$_2$)$_2$NH | 2-tetrahydropyranyl | 61.2/61.6 | 6.6/6.5 | 27.7/27.8 | 354.4 |
| 176 | furfurylamino | NH$_2$(CH$_2$)$_3$NH | 2-tetrahydropyranyl | 58.2/58.0 | 6.8/6.7 | 26.4/26.3 | 372.5 |
| 177 | (E)-(4-hydroxy-3-methylbut-2-en-1-yl)amino | NH$_2$(CH$_2$)$_3$NH | 2 tetrahydropyranyl | 57.6/57.2 | 7.8/7.5 | 26.1/25.8 | 376.5 |
| 178 | furfurylamino | NH$_2$(CH$_2$)$_4$NH | 2-tetrahydropyranyl | 59.2/59.0 | 7.1/7.3 | 25.4/25.4 | 386.5 |
| 179 | furfurylamino | NH$_2$(CH$_2$)$_3$O | 2-tetrahydropyranyl | 58.1/58.4 | 6.5/6.4 | 22.6/22.9 | 373.4 |
| 180 | (3-methylbut-2-en-1-yl)amino | NH$_2$(CH$_2$)$_3$O | 2-tetrahydropyranyl | 60.0/60.5 | 7.8/8.0 | 23.3/23.4 | 361.5 |
| 181 | furfurylamino | HO(CH$_2$)$_2$NH | 2-tetrahydropyranyl | 57.0/57.3 | 6.2/6.3 | 23.5/23.7 | 359.4 |
| 182 | benzylamino | HO(CH$_2$)$_2$NH | 2-tetrahydropyranyl | 61.9/62.1 | 6.6/6.6 | 22.8/22.5 | 369.4 |
| 183 | (E)-(4-hydroxy-3-methylbut-2-en-1-yl)amino | HO(CH$_2$)$_2$NH | 2-tetrahydropyranyl | 56.3/56.3 | 7.2/7.1 | 23.2/23.3 | 363.4 |
| 184 | (3-methylbut-2-en-1-yl)amino | HO(CH$_2$)$_2$NH | 2-tetrahydropyranyl | 58.9/58.8 | 7.6/7.2 | 24.3/24.5 | 347.4 |
| 185 | furfurylamino | HO(CH$_2$)$_3$NH | 2-tetrahydropyranyl | 58.1/58.4 | 6.5/6.9 | 22.6/22.4 | 373.4 |
| 186 | (E)-(4-hydroxy-3-methylbut-2-en-1-yl)amino | HO(CH$_2$)$_3$NH | 2-tetrahydropyranyl | 57.4/57.9 | 7.5/7.4 | 22.3/22.6 | 377.5 |
| 187 | (3-methylbut-2-en-1-yl)amino | HO(CH$_2$)$_3$NH | 2-tetrahydropyranyl | 60.0/59.8 | 7.8/7.6 | 23.3/23.3 | 361.5 |

TABLE 3

Compounds of this invention prepared according to Example 4

| | Substituent | | | CHN analyses calculated/found | | | ESI-MS |
|---|---|---|---|---|---|---|---|
| No | R6 | R8 | R9 | % C | % H/ | % N | [M+H+] |
| 188 | furfurylamino | (CH$_3$)$_2$N | 2-tetrahydrofuranyl | 58.5/58.3 | 6.1/6.1 | 25.6/25.4 | 329.4 |
| 189 | (Z)-(4-hydroxy-3-methylbut-2-en-1-yl)amino | (CH$_3$)$_2$N | 2-tetrahydrofuranyl | 57.8/58.4 | 7.3/7.4 | 25.3/25.0 | 333.4 |
| 190 | (E)-(4-hydroxy-3-methylbut-2-en-1-yl)amino | (CH$_3$)$_2$N | 2-tetrahydrofuranyl | 57.8/58.2 | 7.3/7.4 | 25.3/25.3 | 333.4 |
| 191 | 4-chlorobenzylamino | (CH$_3$)$_2$N | 2-tetrahydrofuranyl | 58.0/58.2 | 5.7/5.9 | 22.5/22.6 | 373.9 |
| 192 | 3-methoxylbenzylamino | (CH$_3$)$_2$N | 2-tetrahydrofuranyl | 61.9/61.8 | 6.6/6.4 | 22.8/23.0 | 369.4 |
| 193 | 2-hydroxy-3-methoxybenzylamino | (CH$_3$)$_2$N | 2-tetrahydrofuranyl | 59.4/59.5 | 6.3/6.4 | 21.9/22.2 | 385.4 |
| 194 | anilino | (CH$_3$)$_2$N | 2-tetrahydrofuranyl | 63.0/63.2 | 6.2/6.2 | 25.9/26.1 | 330.4 |
| 195 | 3-methoxyanilino | (CH$_3$)$_2$N | 2-tetrahydrofuranyl | 61.0/61.6 | 6.3/6.1 | 23.7/23.6 | 355.4 |
| 196 | furfurylamino | CH$_2$=CHCH$_2$NH | 2-tetrahydrofuranyl | 60.0/60.5 | 5.9/6.0 | 24.7/24.5 | 341.4 |
| 197 | furfurylamino | NH$_2$ | 2-tetrahydrofuranyl | 56.0/56.2 | 5.4/5.7 | 28.0/28.4 | 301.3 |
| 198 | benzylamino | NH$_2$ | 2-tetrahydrofuranyl | 61.9/62.3 | 5.9/6.2 | 27.1/26.5 | 311.4 |
| 199 | (Z)-(4-hydroxy-3-methylbut-2-en-1-yl)amino | NH$_2$ | 2-tetrahydrofuranyl | 55.3/55.1 | 6.6/6.8 | 27.6/27.8 | 305.4 |
| 200 | (E)-(4-hydroxy-3-methylbut-2-en-1-yl)amino | NH$_2$ | 2-tetrahydrofuranyl | 55.3/55.5 | 6.6/6.5 | 27.6/27.9 | 305.4 |
| 201 | 4-hydroxybenzylamino | NH$_2$ | 2-tetrahydrofuranyl | 58.9/58.4 | 5.6/5.4 | 25.8/25.1 | 327.4 |
| 202 | 3,4-dihydroxybenzylamino | NH$_2$ | 2-tetrahydrofuranyl | 56.1/56.4 | 5.3/5.2 | 24.6/24.4 | 343.4 |

TABLE 3-continued

Compounds of this invention prepared according to Example 4

| No | Substituent R6 | R8 | R9 | CHN analyses calculated/found % C | % H/ | % N | ESI-MS [M+H+] |
|---|---|---|---|---|---|---|---|
| 203 | 4-hydroxy-3,5-dimethoxybenzylamino | NH$_2$ | 2-tetrahydrofuranyl | 56.0/56.0 | 5.7/5.8 | 21.8/21.3 | 387.4 |
| 204 | anilino | NH$_2$ | 2-tetrahydrofuranyl | 60.8/60.7 | 5.4/5.6 | 28.4/28.6 | 297.3 |
| 205 | 3-hydroxyanilino | NH$_2$ | 2-tetrahydrofuranyl | 57.7/57.9 | 5.2/5.0 | 26.3/26.4 | 313.3 |
| 206 | furfurylamino | CH$_3$O | 2-tetrahydrofuranyl | 57.1/57.3 | 5.4/5.8 | 22.2/22.5 | 316.3 |
| 207 | (3-methylbut-2-en-1-yl)amino | CH$_3$O | 2-tetrahydrofuranyl | 59.4/59.2 | 7.0/6.8 | 23.1/23.4 | 304.4 |
| 208 | (E)-(4-hydroxy-3-methylbut-2-en-1-yl)amino | CH$_3$O | 2-tetrahydrofuranyl | 56.4/56.7 | 6.6/6.7 | 21.9/22.1 | 320.4 |
| 209 | 3-methoxylbenzylamino | CH$_3$O | 2-tetrahydrofuranyl | 60.8/60.7 | 6.0/6.3 | 19.7/19.9 | 356.4 |
| 210 | anilino | CH$_3$O | 2-tetrahydrofuranyl | 61.7/61.9 | 5.5/5.9 | 22.5/22.1 | 312.4 |
| 211 | furfurylamino | C$_6$H$_5$—CH$_2$O | 2-tetrahydrofuranyl | 64.4/64.5 | 5.4/5.1 | 17.9/17.8 | 392.4 |
| 212 | furfurylamino | SH | 2-tetrahydrofuranyl | 53.0/53.1 | 4.8/4.9 | 22.1/22.1 | 318.4 |
| 213 | benzylamino | SH | 2-tetrahydrofuranyl | 58.7/58.9 | 5.2/5.5 | 21.4/21.5 | 328.4 |
| 214 | (3-methylbut-2-en-1-yl)amino | SH | 2-tetrahydrofuranyl | 55.1/54.7 | 6.3/6.4 | 22.9/23.3 | 306.4 |
| 215 | 4-methoxyanilino | SH | 2-tetrahydrofuranyl | 56.0/55.4 | 5.0/5.1 | 20.4/20.8 | 344.4 |
| 216 | furfurylamino | CH$_3$S | 2-tetrahydrofuranyl | 54.4/54.5 | 5.2/5.6 | 21.1/21.6 | 332.4 |
| 217 | benzylamino | CH$_3$S | 2-tetrahydrofuranyl | 59.8/60.1 | 5.6/5.5 | 20.5/20.4 | 342.4 |
| 218 | (3-methylbut-2-en-1-yl)amino | CH$_3$S | 2-tetrahydrofuranyl | 56.4/56.6 | 6.6/6.7 | 21.9/22.0 | 320.4 |
| 219 | furfurylamino | CH$_3$SO$_2$ | 2-tetrahydrofuranyl | 49.6/49.1 | 4.7/4.8 | 19.3/19.1 | 364.4 |
| 220 | furfurylamino | NH$_2$(CH$_2$)$_3$S | 2-tetrahydrofuranyl | 54.5/54.1 | 5.9/6.1 | 22.4/22.3 | 375.5 |
| 221 | furfurylamino | OH | 2-tetrahydrofuranyl | 55.8/55.7 | 5.0/5.2 | 23.2/23.0 | 302.3 |
| 222 | benzylamino | OH | 2-tetrahydrofuranyl | 61.7/62.0 | 5.5/5.4 | 22.5/22.7 | 312.4 |
| 223 | (E)-(4-hydroxy-3-methylbut-2-en-1-yl)amino | OH | 2-tetrahydrofuranyl | 55.1/55.4 | 6.3/6.3 | 22.9/22.6 | 306.3 |
| 224 | 4-hydroxybenzylamino | OH | 2-tetrahydrofuranyl | 58.7/58.9 | 5.2/5.1 | 21.4/21.2 | 328.4 |
| 225 | anilino | OH | 2-tetrahydrofuranyl | 60.6/60.3 | 5.1/5.0 | 23.6/23.7 | 298.3 |
| 226 | 3-methoxyanilino | OH | 2-tetrahydrofuranyl | 58.7/58.1 | 5.2/5.3 | 21.4/21.5 | 328.4 |
| 227 | furfurylamino | H$_2$NCH$_2$ | 2-tetrahydrofuranyl | 57.3/57.0 | 5.8/5.9 | 26.7/26.4 | 315.4 |
| 228 | benzylamino | H$_2$NCH$_2$ | 2-tetrahydrofuranyl | 63.0/63.1 | 6.2/6.4 | 25.9/25.7 | 325.4 |
| 229 | 3-methoxyanilino | H$_2$NCH$_2$ | 2-tetrahydrofuranyl | 58.7/58.7 | 5.2/5.7 | 21.4/21.6 | 328.4 |
| 230 | furfurylamino | CH$_3$OCO | 2-tetrahydrofuranyl | 59.8/59.9 | 5.6/5.4 | 20.5/20.2 | 342.4 |
| 231 | benzylamino | CH$_3$CH$_2$OCO | 2-tetrahydrofuranyl | 65.7/95.2 | 6.3/6.1 | 19.2/19.0 | 366.4 |
| 232 | 4-hydroxylbenzylamino | CH$_3$CH$_2$OCO | 2-tetrahydrofuranyl | 63.0/62.5 | 6.1/6.1 | 18.4/18.1 | 382.4 |
| 233 | furfurylamino | NH$_2$(CH$_2$)$_2$NH | 2-tetrahydrofuranyl | 56.0/56.2 | 6.2/6.3 | 28.6/28.4 | 344.4 |
| 234 | benzylamino | NH$_2$(CH$_2$)$_2$NH | 2-tetrahydrofuranyl | 61.2/61.1 | 6.6/6.8 | 27.7/27.8 | 354.4 |
| 235 | (3-methylbut-2-en-1-yl)amino | NH$_2$(CH$_2$)$_2$NH | 2-tetrahydrofuranyl | 58.0/58.3 | 7.6/7.5 | 29.6/29.5 | 332.4 |
| 236 | (E)-(4-hydroxy-3-methylbut-2-en-1-yl)amino | NH$_2$(CH$_2$)$_2$NH | 2-tetrahydrofuranyl | 55.3/55.7 | 7.3/7.1 | 28.2/28.4 | 348.4 |
| 237 | 3-hydroxybenzylamino | NH$_2$(CH$_2$)$_2$NH | 2-tetrahydrofuranyl | 58.5/58.4 | 6.3/6.4 | 26.5/26.3 | 370.4 |
| 238 | furfurylamino | NH$_2$(CH$_2$)$_3$NH | 2-tetrahydrofuranyl | 57.1/57.1 | 6.5/6.9 | 27.4/27.3 | 358.4 |
| 239 | (E)-(4-hydroxy-3-methylbut-2-en-1-yl)amino | NH$_2$(CH$_2$)$_3$NH | 2-tetrahydrofuranyl | 56.5/56.4 | 7.5/7.9 | 27.1/27.0 | 362.5 |
| 240 | furfurylamino | NH$_2$(CH$_2$)$_6$NH | 2-tetrahydrofuranyl | 60.1/60.3 | 7.3/7.1 | 24.5/24.0 | 400.5 |
| 241 | furfurylamino | NH$_2$(CH$_2$)$_3$O | 2-tetrahydrofuranyl | 57.0/57.5 | 6.2/6.2 | 23.5/23.8 | 359.4 |
| 242 | (E)-(4-hydroxy-3-methylbut-2-en-1-yl)amino | NH$_2$(CH$_2$)$_3$O | 2-tetrahydrofuranyl | 56.3/56.6 | 7.2/7.0 | 23.2/23.7 | 363.4 |
| 243 | furfurylamino | HO(CH$_2$)$_2$NH | 2-tetrahydrofuranyl | 55.8/55.7 | 5.9/6.0 | 24.4/24.3 | 345.4 |
| 244 | (E)-(4-hydroxy-3-methylbut-2-en-1-yl)amino | HO(CH$_2$)$_2$NH | 2-tetrahydrofuranyl | 55.1/55.0 | 6.9/6.7 | 24.1/24.3 | 349.4 |
| 245 | (3-methylbut-2-en-1-yl)amino | HO(CH$_2$)$_2$NH | 2-tetrahydrofuranyl | 57.8/57.9 | 7.3/7.1 | 25.3/25.0 | 333.4 |
| 246 | furfurylamino | HO(CH$_2$)$_3$NH | 2-tetrahydrofuranyl | 57.0/56.6 | 6.2/6.5 | 23.5/23.5 | 359.4 |
| 247 | (E)-(4-hydroxy-3-methylbut-2-en-1-yl)amino | HO(CH$_2$)$_3$NH | 2-tetrahydrofuranyl | 56.3/56.0 | 7.2/7.1 | 23.2/23.1 | 363.4 |

Example 5

Radical Scavenging Activity Determined by ORAC

The ability of compounds to scavenge free radicals in vitro was determined by Oxygen Radical Absorbance Capacity (ORAC) method. Fluorescein (100 μL, 500 mM) and 25 μL of compound solution were added into each working well in a 96-well microplate preincubated at 37° C. Thereafter, 25 μL of 250 mM AAPH was quickly added, microplate was shaken for 5 s and the fluorescence (Ex. 485 nm, Em. 510 nm) was read every 3 min over 90 min by using microplate reader Infinite 200 (TECAN, Switzerland). The net area under the curve was used to express antioxidant activity relative to trolox which was used as a standard. Compounds with ORAC value higher than 1 are more effective than trolox, the hydrophilic equivalent of vitamin E, on an equimolar basis.

TABLE 4

The ability of compounds to scavenge free radicals in ORAC assay

| Compound | ORAC (compound/trolox ratio) |
|---|---|
| KTHP* | 0.6 ± 0.1* |
| 46 | 1.4 ± 0.0 |
| 145 | 1.3 ± 0.1 |
| 80 | 2.2 ± 0.1 |
| 102 | 4.5 ± 0.1 |
| 82 | 8.5 ± 0.4 |
| 107 | 24.4 ± 1.5 |
| 172 | 28.3 ± 1.6 |
| 124 | 30.1 ± 3.1 |
| 100 | 32.4 ± 3.2 |
| 185 | 48.3 ± 2.3 |
| 181 | 78.1 ± 3.9 |
| 170 | 181.3 ± 5.2 |

*Mean ± SD (n = 3)
*KTHP—kinetin-9-tetrahydropyranyl as a reference compound.

Example 6

Protection of Membrane Lipid Peroxidation

A typical symptom associated with senescence as a direct consequence of increased reactive oxygen species is lipid peroxidation. Therefore the levels of MDA, a decomposition product of lipid peroxidation, were measured in detached wheat leaves that were exposed to the prepared novel derivatives and kinetin for four days in the dark as described in Example 8. MDA levels were measured using a thiobarbituric acid (TBA) method. In detail, 100 mg of fresh plant material was homogenized by high speed shaking in a ball mill (MM301, Retsch, Germany) with 1 mL of 80% methanol. The crude extract was centrifuged at 10,000×g for 5 min, and 100 μL aliquot of supernatant was vortexed with 100 μL of 0.5% (w/v) TBA containing 0.1% (w/v) trichloroacetic acid, and the resulting solution was then incubated for 30 min at 95° C. The samples were quickly cooled on ice and recentrifuged for 5 min at 1000×g. The absorbance of supernatant was measured at 532 nm with background subtraction at 600 nm and the amount of MDA-TBA complex was calculated from the coefficient of absorbance 155 $mM^{-1}cm^{-1}$. Novel derivatives significantly reduced peroxidation of membrane lipids compared to untreated control (Table 5—the values express content of MDA, the decomposition product of membrane lipids). The compounds of this invention dramatically reduced the level of membrane lipid peroxidation during the dark senescence in the detached wheat leaves as you can see from the results in the table 5.

The newly prepared derivatives of the general formula I thus had protective function against the negative action the reactive oxygen species that are highly accumulated in tissues during leaf senescence.

TABLE 5

The effect of novel compounds on lipid membrane peroxidation during the senescence of detached leaves of *Triticum aestivum* cv. Hereward in dark conditions.

| Compound No. | MDA (nmol/g FW) |
|---|---|
| Control | 18.9 (±2.2) |
| 1 | 12.8 (±1.0) |
| 4 | 13.2 (±1.5) |
| 5 | 13.2 (±1.5) |
| 9 | 12.4 (±1.3) |
| 10 | 12.8 (±1.1) |
| 13 | 11.9 (±1.3) |
| 14 | 12.2 (±1.4) |
| 16 | 11.6 (±1.0) |
| 21 | 12.1 (±1.2) |
| 24 | 11.4 (±0.9) |
| 25 | 11.7 (±1.1) |
| 29 | 12.3 (±1.4) |
| 39 | 11.6 (±1.2) |
| 44 | 10.7 (±0.8) |
| 46 | 10.9 (±1.0) |
| 80 | 11.3 (±0.9) |
| 82 | 10.8 (±1.0) |
| 100 | 10.2 (±1.1) |
| 102 | 10.4 (±0.9) |
| 107 | 10.5 (±0.5) |
| 124 | 10.3 (±0.7) |
| 145 | 9.6 (±0.8) |
| 172 | 10.8 (±0.9) |
| 170 | 10.4 (±0.7) |
| 181 | 9.5 (±0.5) |
| 185 | 10.2 (±1.1) |
| 189 | 10.8 (±0.9) |
| 197 | 9.2 (±0.6) |
| 201 | 8.7 (±0.7) |
| 206 | 10.5 (±0.4) |
| 221 | 10.2 (±0.5) |
| 224 | 9.3 (±0.8) |
| 233 | 9.8 (±0.7) |
| 238 | 9.4 (±0.7) |
| 241 | 9.6 (±0.8) |
| 245 | 9.5 (±0.6) |

Example 7

Growth Curves for 6-furfurylamino-8-amino-9-(tetrahydropyran-2-yl)-9H-purine (compound 102) and 6-furfurylamino-8-(2-hydroxyethylamino)-9-(tetrahydropyran-2-yl)-9H-purine (Compound 243)

Figure 2:
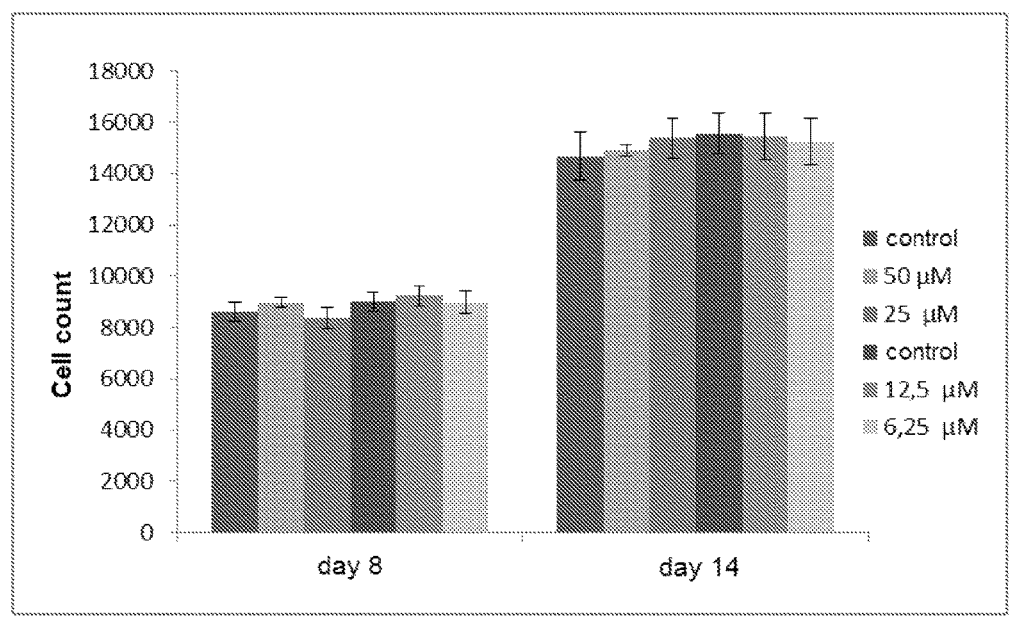
FIG. 2. Shows growth curves of 6-furfurylamino-8-(2-hydroxyethylamino)-9-(tetrahydropyran-2-yl)-9H-purine (compound 243).

The experiments were realised with human diploid fibroblasts BJ v 24-well cultivation plates. The cells were seeded into individual wells (10.000 cell per well) and incubated in DMEM medium with 10% FBS. Do jednotlivých jamek bylo vyseto přibližně 10000 buněk v médiu DMEM s 10% FBS. The tested compound was added after 24 hours to final concentration between 6.25 and 50 μM. Each concentration was tested in 4 replicates. DMSO vehikulum was tested as nontoxic control. To obtain better results of variability at least 8 wells were ket as controls (columns A and D). Cultivation medium with tested compound or DMSO was exchanged twice a week. Seventh or eight day and then 14 day old cella were harvested, trypsinised and cunted on Coulter Z2 instrument. The tested compounds in the concentration range tested and in relation to length of cultivation didn't affect the growth parameters of cells negatively (FIG. 2).

Example 8

Senescence Inhibition by Novel Compounds Tested on Winter Wheat Leaf Segments Seeds of winter wheat, *Triticum aestivum* cv. Hereward, were washed under running water for 24 hours and then sown on vermiculite soaked with Knop's solution. They were placed in the grown chamber at 25° C. with a 16/8 hours light period at 50 mmol·$m^{-2}$·$s^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 ml of a cytokinin solution each. The entire plate was inserted into a plastic box lined with paper tissues soaked in distilled water to prevent leaf sections from drying out. After 96 hours incubation in the dark at 25° C., the leaves were removed and chlorophyll extracted by heating at 80 C for 10 min in 5 ml of 80% ethanol (v/v). The sample volume was then restored to 5 ml by the addition of 80% ethanol (v/v). The absorbance of the extract was recorded at 665 nm. In addition, chlorophyll extracts from fresh leaves and leaf tips incubated in deionized water were measured. From the obtained data, the concentration with highest activity was selected for each compound tested. Relative activity of the compound at this concentration was calculated (see Table 6 below). The activity obtained for $10^{-4}$ M kinetin (Kin) was set as 100%. The values shown are means of five replicates and the whole experiment was repeated twice.

The compounds to be tested were dissolved in dimethylsulfoxide (DMSO) and the solution brought up to $10^{-3}$ M with distilled water. This stock was further diluted in distilled water to concentrations ranging from $10^{-8}$ M to $10^{-4}$ M. The final concentration of DMSO did not exceed 0.2% and therefore did not affect biological activity in the assay system used. As summarized in Table 6 below, the presence of C-8 substitutent was beneficial and led to increase of antisenescent properties.

TABLE 6

The effect of compounds in $10^{-4}$ mol/L concentration on retention of chlorophyll in excised wheat leaf tips

| Compound | Activity (%) (s.d.) |
|---|---|
| kinetin | 100 |
| 1 | 105 (±3) |
| 5 | 118 (±5) |
| 7 | 110 (±2) |
| 8 | 125 (±6) |
| 9 | 115 (±4) |
| 10 | 132 (±7) |
| 11 | 127 (±5) |
| 12 | 140 (±7) |
| 21 | 108 (±3) |
| 24 | 123 (±6) |
| 26 | 117 (±5) |
| 27 | 124 (±4) |
| 28 | 126 (±7) |
| 29 | 117 (±2) |
| 39 | 128 (±3) |
| 41 | 133 (±7) |
| 45 | 112 (±4) |

| Compound | Activity (%) |
|---|---|
| 48 | 120 (±4) |
| 50 | 121 (±4) |
| 52 | 120 (±3) |
| 53 | 125 (±6) |
| 54 | 138 (±7) |
| 55 | 133 (±5) |
| 56 | 141 (±8) |
| 63 | 110 (±2) |
| 64 | 123 (±4) |
| 66 | 132 (±5) |
| 67 | 128 (±6) |
| 68 | 142 (±5) |
| 69 | 115 (±4) |
| 70 | 126 (±1) |
| 71 | 119 (±3) |
| 72 | 106 (±2) |
| 74 | 127 (±5) |
| 76 | 112 (±3) |

* Activity of kinetin set at 100%; Standard deviations are of the mean for 10 replicate determinations.

Example 9

Inhibition of Human Cell Aging by Novel Compounds

In this example, human diploid fibroblasts (HDF cells of various passage levels: passage 25—designated HDF25; passage 45—designated HDF45; passage 80—designated HDF80) were stained for beta-galactosidase activity. The medium used for the cell cultivation was removed the cells were washed twice in PNS, and fixed in 2-3 ml of fixing solution comprised of a 2% formaldehyde and 0.2% glutaraldehyde in PBS. The cells were incubated at room temperature for 5 minutes, and then washed twice with PBS. The cells were subsequently incubated at 37° C. (without $CO_2$) for 1 to 16 hours in 2-3 ml of the solution comprising potassium ferricyanide (5 mM), potassium ferrocyanide (5 mM), $MgCl_2$ (2 mM), X-gal (5-bromo-4-chloro-3-indolyl-beta-D-galactopyranoside) (1 mg/ml), in citric/phosphate buffer, pH 6.0) Following this incubation period, the cell samples were observed in order to detect the presence of blue cells, indicating that X-gal had been cleaved (positively senescent cells). In this experiment, senescent cells, but no other cells were stained blue due to the action of beta-galactosidase on the substrate.

TABLE 7

The effect of novel compounds on the number of senescent cells in the culture of human fibroblasts

| | SENESCENT CELLS (%) | | |
|---|---|---|---|
| Compound | HDF25 | HDF45 | HDF80 |
| BAP | 5 | 9 | 45 |
| kinetin | 3 | 5 | 38 |
| KTHP | 3 | 4 | 26 |
| 21 | 3 | 5 | 20 |
| 24 | 3 | 5 | 21 |
| 26 | 2 | 5 | 19 |
| 27 | 2 | 4 | 21 |
| 39 | 3 | 4 | 20 |
| 41 | 2 | 6 | 21 |
| 45 | 3 | 5 | 20 |
| 48 | 2 | 4 | 21 |
| 50 | 3 | 4 | 19 |
| 52 | 2 | 6 | 21 |
| 53 | 2 | 5 | 21 |
| 54 | 3 | 5 | 20 |
| 55 | 3 | 4 | 18 |
| 56 | 3 | 5 | 21 |
| 63 | 2 | 4 | 19 |
| 64 | 3 | 4 | 8 |
| 66 | 2 | 4 | 16 |
| 67 | 4 | 6 | 18 |
| 68 | 2 | 5 | 19 |
| 69 | 3 | 4 | 14 |
| 70 | 2 | 5 | 18 |
| 71 | 3 | 6 | 19 |
| 72 | 3 | 4 | 17 |
| 74 | 3 | 5 | 21 |
| 76 | 3 | 4 | 15 |

*BAP = 6-benzylaminopurine;
kinetin = 6-furfurylaminopurine;
KTHP—kinetin-9-tetrahydropyranyl As shown in Table 7, with an increasing number of passages, the staining became darker. For the oldest cells, there were only blue cells ranging from bright blue to almost opaque colour. The 6,8-disubstituted-9-(heterocyclyl)purines were very effective in comparison to BAP and kinetin ("classical cytokinin", known in the prior art) in retaining much lower level of senescent cells after 80 passages. In the case of long-standing cultivation the cells treated with the compounds of the invention were able to live for a 30% longer period than the control cells.

Example 10

Effects of New Derivatives on the Lifespan of *C. elegans*

*C. elegans* is a standard model of aging. Its relevance for human aging is generally accepted based primarily on molecular similarity in aging mechanisms and evolutionary conservation of several pathways related to health- and life-span including insulin/IGF-I signaling. (Olsen et. al 2006, doi: 10.1196/annals.1354.015) It is used for drug screening campaigns (reviewed e.g. in Kaletta et al. 2006, doi: 10.1038/nrd2031) including those searching for compounds with cytoprotective activity. Compounds with a life-span extending effect in C. elegans and known health benefits in human include resveratrol, ECG and curcumin (Liao et, al 2011, doi: 10.1016/j.mad.2011.07.008; Wood et al. 2004, doi: 10.1038/nature02789; Abbas et al. 2009, doi: 10.1055/s-0028-1088378). The strain used in this experiment was fem-1(hc17). When grown at 25° C. all animals develop into females which prevents further reproduction and contamination of experiment with progeny. Age-synchronized adults (obtained by sodium hypochlorite treatment) were maintained in liquid S-complete medium. Amphotericin B (0.1 ug/ml) was added to medium to prevent fungal contamination. E. coli strain OP50 (6 mg/ml) was added as a food source. At 4th day of adulthood, worms (53 worms in average per experimental condition) were treated with the test compounds and pipetted into 96-well plate. DMSO vehiculum was used as a negative control and 6-benzylaminopurine (BAP) as a control known in a prior art. Plates were sealed by adhesive PCR foil to prevent evaporation of the medium and the seal was changed once a week to ensure the worms have enough oxygen. Living worms (i.e those moving when exposed to intensive light) were counted in a microscope every 2-3 days until the worms reached 22nd day of adulthood. The effects of the compounds on worm life-span were evaluated in software OASIS (Yang et al 2011, doi: 10.1371/journal.pone.002352).

Results: 100 microM 8-amino-kinetin (82) and 8-bromo-isopentenyladenine (4) extended life-span of C. elegans in comparison with DMSO vehiculum (Bonferroni corrected p<0.05)—FIG. X shows survival curves including the one for equimolar comparator 6-benzylaminopurine. Corresponding restricted means were 15.31, 15.7, 12.98, 12.95 respectively.

Example 11

Effect of the Novel Compounds on Plant Cell Division

Cytokinin-dependent tobacco callus Nicotiana tabacum L. cv. Wisconsin 38 was maintained at 25° C. in darkness on modified MS medium, containing 4 µmol/l nicotinic acid, 2.4 µmol/l pyridoxine hydrochloride, 1.2 µmol/l thiamine, 26.6 µmol/l glycine, 1.37 µmol/l glutamine, 1.8 µmol/l myo-inositol, 30 g/l of sucrose, 8 g/l of agar, 5.37 µmol/l NAA and 0.5 µmol/l BAP. Subcultivation was carried out every three weeks. Fourteen days before the bioassay, the callus tissue was transferred to the media without BAP. Biological activity was determined from the increase in fresh callus weight after four weeks of cultivation. Five replicates were prepared for each cytokinin concentration and the entire test was repeated twice. From the obtained data, the concentration with highest activity was selected for each compound tested. Relative activity at this concentration was calculated (see Table 17 below). The activity obtained for $10^{-6}$ M kinetin (Kin) was set as 100%.

The cytokinins to be tested were dissolved in dimethylsulfoxide (DMSO) and the solution brought up to $10^{-3}$M with distilled water. This stock was further diluted in the respective media used for the biotest to concentrations ranging from $10^{-8}$ M to $10^{-4}$ M. The final concentration of DMSO did not exceed 0.2% and therefore did not affect biological activity in the assay system used.

As summarized in Table 8, the compounds of this invention increases the cell division promoting activity and in contrast to cytokinins, which show sharp concentration optimum, most of the new compounds have markedly extended range of the optimal concentration (over two to three orders of magnitude). As shown in FIG. 1, new derivatives of purine derivatives thus loose their cytotoxic effects when applied in higher concentrations.

TABLE 8

The effect on growth of cytokinin-dependent tobacco callus Nicotiana tabacum L. cv. Wisconsins 38

| Compound | Concentration with highest activity (mol/l) | Activity (%); (s.d.) |
|---|---|---|
| Kinetin | $10^{-6}$ | 100 |
| 3 | $10^{-6}$-$10^{-4}$ | 118 (±6) |
| 5 | $10^{-6}$-$10^{-4}$ | 124 (±6) |
| 7 | $10^{-6}$-$10^{-4}$ | 114 (±5) |
| 8 | $10^{-6}$-$10^{-4}$ | 119 (±7) |
| 9 | $10^{-6}$-$10^{-4}$ | 108 (±3) |
| 23 | $10^{-6}$-$10^{-5}$ | 125 (±7) |
| 24 | $10^{-6}$-$10^{-5}$ | 128 (±8) |
| 26 | $10^{-6}$-$10^{-5}$ | 117 (±4) |
| 27 | $10^{-6}$-$10^{-5}$ | 115 (±4) |
| 28 | $10^{-6}$-$10^{-4}$ | 107 (±2) |
| 29 | $10^{-6}$-$10^{-4}$ | 112 (±3) |
| 64 | $10^{-6}$-$10^{-4}$ | 130 (±10) |
| 65 | $10^{-6}$-$10^{-4}$ | 127 (±9) |
| 69 | $10^{-6}$-$10^{-4}$ | 111 (±5) |
| 70 | $10^{-6}$-$10^{-4}$ | 110 (±1) |
| 71 | $10^{-6}$-$10^{-4}$ | 116 (±2) |
| 74 | $10^{-6}$-$10^{-4}$ | 122 (±4) |
| 75 | $10^{-6}$-$10^{-4}$ | 119 (±4) |
| 76 | $10^{-6}$-$10^{-4}$ | 114 (±3) |

| Compound | Concentration with highest activity (mol/l) | Activity (%) |
|---|---|---|
| 124 | $10^{-6}$-$10^{-4}$ | 105 (±2) |
| 125 | $10^{-6}$-$10^{-4}$ | 104 (±2) |
| 126 | $10^{-6}$-$10^{-4}$ | 116 (±6) |
| 127 | $10^{-6}$-$10^{-4}$ | 114 (±6) |
| 128 | $10^{-6}$-$10^{-5}$ | 121 (±5) |
| 129 | $10^{-6}$-$10^{-5}$ | 111 (±4) |
| 130 | $10^{-6}$-$10^{-4}$ | 108 (±3) |
| 145 | $10^{-6}$-$10^{-4}$ | 103 (±5) |
| 146 | $10^{-6}$-$10^{-5}$ | 108 (±5) |
| 147 | $10^{-6}$-$10^{-4}$ | 112 (±2) |
| 149 | $10^{-6}$-$10^{-4}$ | 107 (±1) |
| 150 | $10^{-6}$-$10^{-5}$ | 105 (±2) |
| 151 | $10^{-6}$-$10^{-4}$ | 109 (±5) |
| 206 | $10^{-6}$-$10^{-4}$ | 110 (±3) |
| 207 | $10^{-6}$-$10^{-4}$ | 114 (±3) |
| 208 | $10^{-6}$-$10^{-4}$ | 119 (±7) |
| 209 | $10^{-6}$-$10^{-4}$ | 112 (±4) |
| 216 | $10^{-6}$-$10^{-4}$ | 103 (±4) |
| 218 | $10^{-6}$-$10^{-4}$ | 113 (±5) |

* Activity of kinetin set at 100%.

Example 12

In Vitro Cytotoxic Activity (Metabolisation of Calcein AM)

Because toxic compounds negatively influence metabolic processes of cells, many standard cytotoxicity assays are based on measurement of metabolisation rate of various artificial substrates. Resulting product is then quantified, for example, by means of spectrometry. The assays can be easily modified for use in 96-well plates. For evaluation of cytotoxicity of the 6,8-disubstituted-6,8-disubstituted-9-(heterocyclyl)purines of this invention, a microtiter assay based on quantification of metabolisation of Calcein AM was used. The assay is widely used in drug screening programs and in chemosensitivity testing. In live cells, Calcein AM is enzymatically hydrolysed and accumulation of resulting calcein is manifested by green fluorescence.

The following human cell lines were used for routine screening of the compounds: normal diploid fibroblasts BJ, T-lymphoblastic leukemia cell line CEM, promyelocytic leukemia cell line HL-60, erytroid leukemia cell line K-562, breast carcinoma cell line MCF-7, osteosarcoma cell line HOS and melanoma cell line G-361. The cells were maintained in Nunc/Corning 80 cm² plastic tissue culture flasks and cultured in cell culture medium (DMEM with 5 g/l glucose, 2 mM glutamine, 100 U/ml penicillin, 100 mmg/ml streptomycin, 10% fetal calf serum and sodium bicarbonate). The cell suspensions were prepared and diluted according to the particular cell type and the expected target cell density (2.500-30.000 cells per well based on cell growth characteristics) and pipetted (80 µl) into 96-well plates. Inoculates were allowed a pre-incubation period of 24 hours at 37° C. and 5% $CO_2$ for stabilization. Tested compound was added in total volume of 20 µl of water at time zero. Usually, test compound was evaluated at six 3-fold dilutions. In routine testing, the highest concentration tested was 100 µM, but it could have been adjusted because of limited solubility of a compound. All drug concentrations were tested in triplicates.

Incubations of cells with the test compounds lasted for 72 hours at 37° C., in 5% $CO_2$ atmosphere and 100% humidity. At the end of incubation period Calcein AM in PBS was added into final concentration of 1 µg/ml. After another 1 hour of incubation fluorescence (FD) was measured with the Labsystem FIA Reader Fluoroscan Ascent (UK). Growth inhibition (GI) was estimated using the following equitation: GI=(mean $FD_{drug\ exposed\ wells}$–mean $FD_{blank}$)/(mean $FD_{control\ wells}$–mean $FD_{blank}$)×100%. The $GI_{50}$ value, the drug concentration causing 50% reduction of Calcein AM conversion, was calculated from the obtained dose response curves.

Cytoxicity of compounds was tested on panel of cell lines of different histogenetic and species origin. As shown in Table 9, 6,8-disubstituted-9-(heterocyclyl)purines exceeded maximal concentration tested which suggests that the compounds could be applied at concentrations causing desired effect without negative side effects.

TABLE 9

Cytotoxicity for different cancer cell lines

| Compound | Cell line tested/$IC_{50}$ (µmol/L) | | | | | | Highest concentration tested (µmol/L) |
|---|---|---|---|---|---|---|---|
| | BJ | CEM | K-562 | MCF7 | HOS | G-361 | |
| 3 | >50 | >50 | >50 | >50 | >50 | >50 | 50 |
| 5 | >50 | >50 | >50 | >50 | >50 | >50 | 50 |
| 7 | >100 | >50 | >50 | >100 | >100 | >100 | 100 |
| 8 | >100 | >100 | >100 | >100 | >100 | >100 | 100 |
| 9 | >50 | >50 | >50 | >50 | >50 | >50 | 50 |
| 23 | >50 | >50 | >50 | >50 | >50 | >50 | 50 |
| 24 | >50 | >50 | >50 | >50 | >50 | >50 | 50 |
| 26 | >50 | >50 | >50 | >50 | >50 | >50 | 50 |

TABLE 9-continued

Cytotoxicity for different cancer cell lines

| Compound | Cell line tested/$IC_{50}$ (µmol/L) | | | | | | Highest concentration tested (µmol/L) |
|---|---|---|---|---|---|---|---|
| | BJ | CEM | K-562 | MCF7 | HOS | G-361 | |
| 27 | >50 | >50 | >50 | >50 | >50 | >50 | 50 |
| 28 | >50 | >50 | >50 | >50 | >50 | >50 | 50 |
| 29 | >50 | >50 | >50 | >50 | >50 | >50 | 50 |
| 64 | >50 | >50 | >50 | >50 | >50 | >50 | 50 |
| 65 | >50 | >50 | >50 | >50 | >50 | >50 | 50 |
| 69 | >50 | >50 | >50 | >50 | >50 | >50 | 50 |
| 124 | >50 | >50 | >50 | >50 | >50 | >50 | 50 |
| 125 | >50 | >50 | >50 | >50 | >50 | >50 | 50 |
| 126 | >50 | >50 | >50 | >50 | >50 | >50 | 50 |
| 127 | >50 | >50 | >50 | >50 | >50 | >50 | 50 |
| 128 | >50 | >50 | >50 | >50 | >50 | >50 | 50 |
| 129 | >50 | >50 | >50 | >50 | >50 | >50 | 50 |
| 130 | >50 | >50 | >50 | >50 | >50 | >50 | 50 |
| 145 | >50 | >50 | >50 | >50 | >50 | >50 | 50 |
| 146 | >50 | >50 | >50 | >50 | >50 | >50 | 50 |
| 147 | >50 | >50 | >50 | >50 | >50 | >50 | 50 |
| 149 | >50 | >50 | >50 | >50 | >50 | >50 | 50 |
| 150 | >50 | >50 | >50 | >50 | >50 | >50 | 50 |
| 151 | >50 | >50 | >50 | >50 | >50 | >50 | 50 |
| 206 | >50 | >50 | >50 | >50 | >50 | >50 | 50 |
| 207 | >50 | >50 | >50 | >50 | >50 | >50 | 50 |
| 208 | >50 | >50 | >50 | >50 | >50 | >50 | 50 |
| 209 | >50 | >50 | >50 | >50 | >50 | >50 | 50 |
| 216 | >50 | >50 | >50 | >50 | >50 | >50 | 50 |
| 218 | >50 | >50 | >50 | >50 | >50 | >50 | 50 |

Example 13

In Vitro Cytotoxic Activity (Metabolisation of MTT)

MTT (metabolic tetrazolium toxicity) assay is a standard colorimetric assay for evaluation of cytotoxicity. Mitochondrial dehydrogenase activity converts yellow MTT into violet formazan which is measured by means of spectrometry.

Human diploid fibroblast BJ (passage 18-22) were seeded into 96-well plate (5.000 cells per well). After 6 hours cultivation medium (DMEM with 5 g/l glucose, 2 mM glutamine, 100 U/ml penicillin, 100 mmg/ml streptomycin, 10% fetal calf serum and sodium bicarbonate) was replaced with the cultivation medium containing test compounds in concentration range of 0-200 ☐M. Highest concentration was adjusted if the solubility of the compound was limiting. Every concentration was tested in pentaplicate. MTT was added to the cells after 72 hours incubation (final concentration 0.5 mg/ml) and incubation continued for another 3 hours. MTT was solubilised by DMSO and absorbance at 570 nm was measured. Growth inhibition (GI) was estimated using the following equitation: GI=(mean A drug exposed wells–mean $A_{blank}$/mean $A_{control\ wells}$–mean $A_{blank}$)×100%. The $GI_{20}$ value, the drug concentration causing 20% decrease in mitochondrial dehydrogenase activity, was calculated from the obtained dose response curves. As shown in Table 10, $GI_{20}$ of 6,8-disubstituted-9-(heterocyclyl)purines exceeded maximal concentration tested which suggests that the compounds could be applied at concentrations causing desired effect without negative side effects.

TABLE 10

Cytotoxicity for human diploid fibroblasts

| Compound | $GI_{20}$ (μmol/L) | Maximum tested concentration (μmol/L) |
|---|---|---|
| 3 | >50 | 50 |
| 5 | >100 | 100 |
| 7 | >200 | 200 |
| 8 | >200 | 200 |
| 9 | >100 | 100 |
| 23 | >100 | 100 |
| 24 | >100 | 100 |
| 26 | >100 | 100 |
| 27 | >100 | 100 |
| 28 | >100 | 100 |
| 29 | >100 | 100 |
| 64 | >100 | 100 |
| 65 | >100 | 100 |
| 69 | >100 | 100 |
| 124 | >100 | 100 |
| 125 | >100 | 100 |
| 126 | >100 | 100 |
| 127 | >100 | 100 |
| 128 | >100 | 100 |
| 129 | >100 | 100 |
| 130 | >100 | 100 |
| 145 | >100 | 100 |
| 146 | >100 | 100 |
| 147 | >100 | 100 |
| 149 | >100 | 100 |
| 150 | >100 | 100 |
| 151 | >100 | 100 |
| 206 | >100 | 100 |
| 207 | >100 | 100 |
| 208 | >100 | 100 |
| 209 | >100 | 100 |
| 216 | >100 | 100 |
| 218 | >100 | 100 |

Example 13

Ames Test

A number of tests related to the safety of have been carried out using conventionally accepted protocols and procedures. The results of these studies are summarized herein. Tests were carried out using DMSO as solvent and dose levels of compound 21, 24, 26, 27, 39, 41, 45, 48, 50, 52, 53, 54, 55, 56, 63, 64, 66, 67, 68, 69, 70, 71, 72, 74, 76, 124, 125, 126, 127, 128, 129, 130, 145, 146, 147, 149, 150, 151, 208, 216, 218 a 243 at 2.5, 5.0, 15, 50, 500, 1500, and 5000 μg/plate based upon standard protocol and procedures (Ames et al., Mutation Research, 31, 347-364 (1975); Maron et al., Mutation Research, 113, 173-215 (1983)). Using *Salmonella typhimurium* histidien auxotrophs TA98 and TA100 in the presence and absence of Aroclor-induced rat liver S9, no positive mutagenic responses were observed.

Example 14

Formulations

The growth regulatory formulations usually contain from 0.1 to 99% by weight, especially from 0.1 to 95% by weight, of active ingredient mixture comprising a 6,8-disubstitued purine of this invention, from 1 to 99.9% by weight of a solid or liquid formulation adjuvant, and from 0 to 25% by weight, especially from 0.1 to 25% by weight, of a surfactant. Whereas commercial products are usually formulated as concentrates, the end user will normally employ dilute formulations. The compositions may also comprise further ingredients, such as stabilizers, e.g., vegetable oils or epoxidised vegetable oils (epoxidised coconut, rapeseed oil or soybean oil), antifoams, e.g., silicone oil, preservatives, viscosity regulators, binders, tackifiers, and also fertilisers or other active ingredients. Preferred formulations have especially the following compositions: (%=percent by weight):

| Emulsifiable concentrates | a) | b) | c) | d) |
|---|---|---|---|---|
| active ingredint mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol- of ethylene oxide) | 4% | — | 2% | |
| cyclohexanone | — | — | 10% | 20% |
| aromatic hydrocarbon mixture (C9-C12) | 85% | 78% | 55% | 16% |

Emulsions of any desired concentration can be obtained from such concentrates by dilution with water.

| Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol (MW 400) | 20% | 10% | — | — |
| N-methyl-2-pyrrolidone | — | — | 30% | 10% |
| aromatic. hydrocarbon mixture 9C9-C12) | 75% | 60% | — | — |

The solutions are suitable for use in the form of microdrops.

| Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjutants, giving a suspension concentrate from which suspensions of any desired concentration can be obtained by dilution with water.

Dry Capsules 5000 capsules, each of which contain 0.25 g of one of the 6,8-disubstituted-6,8-disubstituted-9-(heterocyclyl)purines as active ingredient, are prepared as follows:

Composition: Active ingredient: 1250 g; Talc:180 g; Wheat starch:120 g; Magnesium stearate:80 g; Lactose 20 g.

Preparation process: The powdered substances mentioned are pressed through a sieve of mesh width 0.6 mm. Portions of 0.33 g of the mixture are transferred to gelatine capsules with the aid of a capsule-filling machine.

Soft Capsules 5000 soft gelatine capsules, each of which contain 0.05 g of one of the 6,8-disubstituted-6,8-disubstituted-9-(heterocyclyl)purine as active ingredient, are prepared as follows:

Composition: 250 g Active ingredient+2 liters Lauroglycol

Preparation process: The powdered active ingredient is suspended in Lauroglykol® (propylene glycol laurate, Gattefossé S.A., Saint Priest, France) and ground in a wet-pulveriser to a particle size of about 1 to 3 mm. Portions of in each case 0.419 g of the mixture are then transferred to soft gelatine capsules by means of a capsule-filling machine.

Soft Capsules 5000 soft gelatine capsules, each of which contain 0.05 g of one of the 6,8-disubstituted-6,8-disubstituted-9-(heterocyclyl)purine as active ingredient, are prepared as follows:

Composition: 250 g Active ingredient+1 liter PEG 400+1 liter Tween 80

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

Example 15

Gel Formulation

An ointment formulation was tested during a pilot clinical study with 4 volunteers with psoriatic skin disorders. The components are given in grams per 100 g.

| Compound | Content |
| --- | --- |
| 8-Amino-6-furfurylamino-9-tetrahydropyranylpurine | 1.0 g |
| Butylhydroxytoluenum | 0.2 g |
| Butylparaben | 0.2 g |
| Diethyleneglycol monoethyl ether | 10.0 g |
| Silica colloidalis anhydrica | 5.0 g |
| Propylene glycol laurate | 83.6 g |

The gel consistence may be additionally modified by addition of silica colloidalis anhydrica. It is again expected that the transdermal Transcutol P/Lauroglycol FCC system will increase the efficiency of 8-amino-6-furfurylamino-9-tetrahydropyranyl-purine. Silica colloidalis anhydrica will probably slow down the penetration of the active substance.

Example 16

Preparation Procedure of a Skin Ointment

The formulation components are given in grams per 200 g:

| Compound | Content |
| --- | --- |
| 8-Amino-6-furfurylamino-9-tetrahydropyranylpurine | 2.0 g |
| Butylhydroxytoluenum | 0.4 g |
| Butylparaben | 0.4 g |
| Diethyleneglycol monoethyl ether | 20.0 g |
| Glycerol dibehenate | 44.0 g |
| Propylene glycol laurate | 133.2 g |

Recommended Procedure

Phase A: 2 grams of 8-amino-6-furfurylamino-9-tetrahydropyranylpurine were dissolved in 20 g of Transcutol P while stirring continuously at room temperature in a separate glass or stainless-steel container. The dissolution process may be accelerated by heating the solution to a maximal temperature of 40° C.

Phase B: 0.4 grams of Nipanox BHT and 0.4 g of Nipabutyl were dissolved while stirring continuously in 133.2 g of Lauroglycol FCC at a temperature of approximately 70° C. in another separate glass or stainless-steel container. The clear oily solution is heated to a temperature of approximately 80° C. and 44 g of Compritol 888 ATO are melted in it while stirring continuously. The clear oily solution is cooled down to approximately 60 C and during continuous stirring and cooling down is mixed with phase A. The resulting whitish ointment-like substance is divided into approximately 15 gram portions and filled into prearranged plastic containers.

Example 17

Formulation of a Composition for Topical Application to the Skin

A composition for topical application to the skin contains the following ingredients by weight %:

Active ingredient:

| | |
| --- | --- |
| 8-Amino-6-furfurylamino-9-tetrahydropyranylpurine | 0.1% |

Oil phase:

| | |
| --- | --- |
| Cetyl alcohol | 5.0% |
| Glyceryl monostearate | 15.0% |
| Sorbitan monooleate | 0.3% |
| Polysorbate 80 USP | 0.3% |

Aqueous Phase:

| | |
| --- | --- |
| Methylcellulose 100 cps | 1.0% |
| Methyl paraben | 0.25% |
| Propyl paraben | 0.15% |
| Purified water | q.s. to 100% |

Methyl paraben and propyl paraben were dissolved in hot water and subsequently methylcellulose was dispersed in the hot water. The mixture was chilled at 6° C. until the methylcellulose dissolved. The mixture was then heated to 72° C. and added to the oil phase which was heated to 70° C. while stirring continuously. 8-Amino-6-furfurylamino-9-tetrahydropyranylpurine was added at a temperature of 35° C. and the resulting mixture was stirred continuously until dispersed. This composition is applied to the skin on at least a daily basis until the desired skin-ameliorating (anti-aging) effect is reached.

The invention claimed is:

1. A compound of general formula I

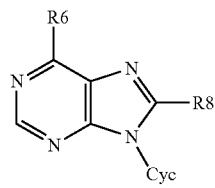

wherein
Cyc is heterocyclyl selected from the group consisting of 2-tetrahydropyranyl and 2-tetrahydrofuranyl;
R6 is —NH—$R_y$,
$R_y$ is selected from the group consisting of:
C$_1$ to C$_8$ linear or branched alkyl, optionally substituted by at least one substituent selected from the group consisting of hydroxy, halogen, C$_1$ to C$_4$ alkoxy,
C$_2$ to C$_8$ linear or branched alkenyl, optionally substituted by at least one substituent selected from the group consisting of hydroxy, halogen, C$_1$ to C$_4$ alkoxy,
C$_3$ to C$_8$ cycloalkyl, optionally substituted by at least one substituent selected from the group consisting of hydroxy, halogen, C$_1$ to C$_4$ alkyl, C$_1$ to C$_4$ alkoxy,
benzyl, optionally substituted by at least one substituent selected from the group consisting of hydroxy, halogen, C$_1$ to C$_4$ alkyl, C$_1$ to C$_4$ alkoxy, amino, nitro,
phenyl, optionally substituted by at least one substituent selected from the group consisting of hydroxy, halogen, C$_1$ to C$_4$ alkyl, C$_1$ to C$_4$ alkoxy, amino, nitro,
furfuryl, optionally substituted by at least one substituent selected from the group consisting of hydroxy, halogen, C$_1$ to C$_4$ alkyl, C$_1$ to C$_4$ alkoxy, amino, nitro,
and
R8 is selected from the group comprising amino, hydroxy, fluorine, bromine, chlorine, acyl, acyloxy, amido, alkoxy, benzyloxy, alkylamino, dialkylamino, alkenylamino, carbamoyl, carboxyl, cyano, hydrazino, —NHOH, NHNH$_2$, —NHCONH$_2$, —NH—C(NH)NH$_2$, nitro, sulphanyl, alkylsulphanyl, sulpho, and alkyloxycarbonyl, whereas alkylamino denotes the group —N($R_e$)$_2$, wherein each $R_e$ is independently selected from hydrogen, alkyl, and alkenyl, each of which can be substituted by amino or hydroxyl substituent.

2. The compound of claim 1, wherein $R_y$ is selected from the group consisting of furfuryl, phenyl, benzyl, 3-methylbut-2-en-1-yl, cyclohexylmethyl, allyl or 3,3-dimethylallyl, wherein each of these substituents can optionally be substituted with one or more substitutents selected from halogen, hydroxy, methoxy, methyl, amino, nitro or combinations thereof.

3. The compound of claim 1, wherein R8 is selected from the group consisting of amino, alkylamino, hydroxy, chloro, fluoro, bromo, amino(C$_1$-C$_5$ alkyl)amino, hydroxy(C$_1$-C$_5$ alkyl)amino, NHOH, NHNH$_2$, carboxyl, nitro, sulphanyl, methylsulphanyl, methoxy.

4. The compound of claim 1, selected from the group comprising 6-furfurylamino-8-(amino, hydroxy, chloro, fluoro, bromo, amino(C1-C5alkyl)amino, hydroxy(C1-C5 alkyl)amino, NHOH, NHNH$_2$, carboxyl, nitro, sulphanyl, methylsulphanyl, methoxy)-9-(2-tetrahydropyranyl or 2-tetrahydrofuranyl)purine, 6-(3-hydroxybenzylamino)-8-(amino, hydroxy, chloro, fluoro, bromo, amino(C1-C5alkyl) amino, hydroxy(C1-C5 alkyl)amino, NHOH, NHNH$_2$, carboxyl, nitro, sulphanyl, methylsulphanyl, methoxy)-9-(2-tetrahydropyranyl or 2-tetrahydrofuranyl)purine, 6-(4-hydroxybenzylamino)-8-(amino, hydroxy, chloro, fluoro, bromo, amino(C1-C5alkyl)amino, hydroxy(C1-C5 alkyl) amino, NHOH, NHNH$_2$, carboxyl, nitro, sulphanyl, methylsulphanyl, methoxy)-9-(2-tetrahydropyranyl or 2-tetrahydrofuranyl)purine, 6-(Z)-(4-hydroxy-3-methylbut-2-en-1-ylamino)-8-(amino, hydroxy, chloro, fluoro, bromo, amino (C1-C5 alkyl)amino, hydroxy(C1-C5 alkyl)amino, NHOH, NHNH$_2$, carboxyl, nitro, sulphanyl, methylsulphanyl, methoxy)-9-(2-tetrahydropyranyl or 2-tetrahydrofuranyl) purine, 6-(E)-(4-hydroxy-3-methylbut-2-en-1-ylamino)-8-(amino, hydroxy, chloro, fluoro, bromo, amino(C1-C5 alkyl) amino, hydroxy(C1-C5 alkyl)amino, NHOH, NHNH$_2$, carboxyl, nitro, sulphanyl, methylsulphanyl, methoxy)-9-(2-tetrahydropyranyl or 2-tetrahydrofuranyl)purine, 6-(4-hydroxy-3-methylbutylamino)-8-(amino, hydroxy, chloro, fluoro, bromo, amino(C1-C5 alkyl)amino, hydroxy(C1-C5alkyl)amino, NHOH, NHNH$_2$, carboxyl, nitro, sulphanyl, methylsulphanyl, methoxy)-9-(2-tetrahydropyranyl or 2-tetrahydrofuranyl)purine or salts and their salts with alkali metals, ammonia and amines, in the form of racemates and optical isomers as well as their additional salts with acids thereof.

5. Pharmaceutical and/or cosmetic composition comprising one or more compounds of the formula I according to claim 1 and at least one auxiliary substance.

6. A method of inhibiting lipid pre-oxidation in plants, mammals or humans comprising the step of applying or administering the compound according to claim 1 to a plant, a mammal or a human in need of such treatment.

7. A method of treatment of a skin condition selected from the group consisting of acne and erythema, or an inflammation, comprising the step of administering the compound according to claim 1 to a mammal in need of such treatment.

8. A method of improving the overall appearance and condition of the skin of a mammal, comprising the step of administering the compound according to claim 1 to a mammal in need of such treatment.

9. A method for ameliorating the adverse effects of aging in mammalian and plant cells, said method comprising administering at least one compound according to claim 1, to the mammalian cells or tissue in an amount effective to ameliorate the adverse effects of aging in the cells.

10. A method of treatment of acne, erythema or redness comprising the step of administering the compound according to claim 1 to a mammal in need of such treatment.

11. A method of suppressing immunostimulation comprising the step of administering the compound according to claim 1 to a mammal in need of such treatment.

* * * * *